(12) United States Patent
McMillan et al.

(10) Patent No.: US 9,554,856 B2
(45) Date of Patent: *Jan. 31, 2017

(54) LOW PROFILE APPARATUS AND METHOD FOR PHOTOTHERAPY

(71) Applicant: Gradiant Research, LLC, Concord, MA (US)

(72) Inventors: Kathleen McMillan, Concord, MA (US); Anurag Gupta, Tucson, AZ (US); James Patrick McGuire, Jr., Pasadena, CA (US)

(73) Assignee: GRADIANT RESEARCH, LLC, Concord, MA (US)

( * ) Notice: Subject to any disclaimer, the term of this patent is extended or adjusted under 35 U.S.C. 154(b) by 59 days.

This patent is subject to a terminal disclaimer.

(21) Appl. No.: 13/965,715

(22) Filed: Aug. 13, 2013

(65) Prior Publication Data
US 2013/0345687 A1 Dec. 26, 2013

Related U.S. Application Data

(60) Division of application No. 12/952,946, filed on Nov. 23, 2010, now abandoned, which is a
(Continued)

(51) Int. Cl.
*A61N 5/067* (2006.01)
*A61B 18/22* (2006.01)

(52) U.S. Cl.
CPC .................................... *A61B 18/22* (2013.01)

(58) Field of Classification Search
CPC ...... A61N 5/06; A61N 5/0613; A61N 5/0616; A61N 5/062; A61N 2005/065; A61N 2005/067; A61N 2005/0642; A61N 2005/0643; A61N 2005/0644; A61N 2005/0664; A61N 2005/0665; A61N 2005/0666; A61B 18/18; A61B 18/20; A61B 18/222; A61B 2018/201; A61B 2018/0215; A61B 2018/202; A61B 2018/2255; A61B 2018/2261; A61B 2018/2272; A61B 2018/2277
(Continued)

(56) References Cited

U.S. PATENT DOCUMENTS

| 4,638,436 A | 1/1987 | Badger et al. |
| 5,328,488 A | 7/1994 | Daikuzono |

(Continued)

FOREIGN PATENT DOCUMENTS

| CN | 1053540 A | 8/1991 |
| CN | 1665453 A | 9/2005 |

(Continued)

OTHER PUBLICATIONS

EP 11831692.6 Supplementary European Search Report dated Aug. 1, 2014.
(Continued)

*Primary Examiner* — Ahmed Farah
(74) *Attorney, Agent, or Firm* — Hamilton, Brook, Smith & Reynolds, P.C.

(57) ABSTRACT

Disclosed herein are optical assemblies having thin, low profile shapes. These optical assemblies may be used with fiber coupled lasers and other light sources, including high power sources, to irradiate tissue at a wavelength suitable for inducing ablation or coagulation to a target depth, denaturation, thermal modification of a tissue, and/or preferential injury to a target tissue structure. Example optical assemblies can produce substantially uniform illumination patterns that are useful for treating superficial tissue, including the internal or luminal (e.g., esophageal) tissue. Some examples may have capability for cooling superficial tissue
(Continued)

or skin, such as a detachable, reusable heat sink for active cooling without consumables, fluid pumps, or other cooling equipment.

22 Claims, 45 Drawing Sheets

Related U.S. Application Data continuation-in-part of application No. 12/625,335, filed on Nov. 24, 2009, now Pat. No. 8,685,010.

(60) Provisional application No. 61/117,279, filed on Nov. 24, 2008, provisional application No. 61/264,161, filed on Nov. 24, 2009.

(58) Field of Classification Search
USPC .................. 607/88–94; 606/13, 14, 16–18
See application file for complete search history.

(56) References Cited

U.S. PATENT DOCUMENTS

| | | | |
|---|---|---|---|
| 5,445,146 A | 8/1995 | Bellinger | |
| 5,658,275 A | 8/1997 | Saadat | |
| 5,861,020 A | 1/1999 | Schwarzmaier | |
| 5,951,596 A | 9/1999 | Bellinger | |
| 6,240,925 B1 | 6/2001 | McMillan et al. | |
| 6,267,779 B1 | 7/2001 | Gerdes | |
| 6,290,713 B1 | 9/2001 | Russell | |
| 6,339,458 B1 | 1/2002 | Ohkawa | |
| 6,389,313 B1 | 5/2002 | Marchitto et al. | |
| 6,451,013 B1 | 9/2002 | Bays et al. | |
| 6,659,999 B1 | 12/2003 | Anderson et al. | |
| 6,682,501 B1 | 1/2004 | Nelson et al. | |
| 6,743,249 B1* | 6/2004 | Alden .............................. | 607/88 |
| 6,746,473 B2 | 6/2004 | Shanks et al. | |
| 7,018,397 B2* | 3/2006 | Neuberger ............ | A61N 5/062 |
| | | | 606/17 |
| 7,043,287 B1 | 5/2006 | Khalil et al. | |
| 8,685,010 B2* | 4/2014 | McMillan .............. | A61B 18/22 |
| | | | 606/13 |
| 2001/0025176 A1 | 9/2001 | Ellsberry et al. | |
| 2002/0058931 A1 | 5/2002 | Parker et al. | |
| 2004/0093042 A1 | 5/2004 | Altshuler et al. | |
| 2005/0143792 A1 | 6/2005 | Jay | |
| 2005/0215987 A1 | 9/2005 | Slatkine | |
| 2006/0047329 A1 | 3/2006 | Krespi et al. | |
| 2006/0058712 A1 | 3/2006 | Altshuler et al. | |
| 2007/0027440 A1* | 2/2007 | Altshuler et al. ................. | 606/9 |
| 2007/0185188 A1 | 8/2007 | Mirejovsky et al. | |
| 2007/0239232 A1* | 10/2007 | Kurtz et al. ..................... | 607/87 |
| 2008/0021370 A1 | 1/2008 | Borenstein | |
| 2008/0228104 A1 | 9/2008 | Uber et al. | |
| 2008/0240172 A1 | 10/2008 | Rizoiu et al. | |
| 2010/0160904 A1 | 6/2010 | McMillan et al. | |
| 2011/0190749 A1 | 8/2011 | McMillan et al. | |
| 2012/0078160 A1 | 3/2012 | McMillan | |
| 2013/0197473 A1 | 8/2013 | McMillan | |
| 2014/0194770 A1 | 7/2014 | McMillan et al. | |

FOREIGN PATENT DOCUMENTS

| | | |
|---|---|---|
| JP | 2001-046396 A | 2/2001 |
| JP | 2001-204831 A | 7/2001 |
| JP | 2006-051388 A | 2/2006 |
| WO | WO 86/01919 A1 | 3/1986 |
| WO | WO 99/01696 | 1/1999 |
| WO | WO 02/087698 A1 | 11/2002 |
| WO | WO 2008/049905 A1 | 5/2008 |
| WO | WO 2008/131302 A2 | 10/2008 |
| WO | WO 2009/124301 A1 | 10/2009 |
| WO | WO 2010/060097 A2 | 5/2010 |
| WO | WO 2010/102099 A1 | 9/2010 |
| WO | WO 2012/048241 A2 | 4/2012 |

OTHER PUBLICATIONS

U.S. Appl. No. 13/878,185 Final Office Action dated May 30, 2014 entitled "Method and Apparatus for Skin Cancer Thermal Therapy".
Notification of Transmittal of the International Search Report and Written Opinion of the International Searching Authority, or the Declaration, for International Application No. PCT/US2009/065768, "Photothermal Treatment of Soft Tissues," mailing date Jul. 20, 2010.
Supplementary European Search Report for European Application No. 09 82 8386, "Photothermal Treatment of Soft Tissues," dated Apr. 11, 2012.
Interview Summary, U.S. Appl. No. 12/952,946, mailed Jun. 25, 2013.
Non-Final Office Action from U.S. Appl. No. 12/952,946, mailed Nov. 7, 2012.
Final Office Action from U.S. Appl. No. 12/952,946, mailed Mar. 13, 2013.
Supplemental Notice of Allowability, U.S. Appl. No. 12/625,335, mailed Jan. 31, 2014.
Notice of Allowance, U.S. Appl. No. 12/625,335, mailed Dec. 6, 2013.
Interview Summary, U.S. Appl. No. 12/625,335, mailed Dec. 19, 2012.
Interview Summary, U.S. Appl. No. 12/625,335, mailed Aug. 9, 2012.
Arens, R., et al., "Linear dimensions of the upper airway structure during development," *Am. J. Respir. Crit. Care Med.*, 165: 117-122 (2002).
Arrarte, J.L.F., et al., "The effect of adenotonsillectomy on oxygen saturation in children with sleep-disordered breathing," *J. Bras. Pneumol.*, 33: 62-68 (2007).
Bhattacharyya, N., "Evaluation of post-tonsillectomy bleeding in the adult population," *ENT-Ear, Nose & Throat Journal*, 80: 544-549 (2001).
Brodsky, L., et al., "Naso- and oropharyngeal dimensions in children with obstructive sleep apnea," *Int. J. Pediatr. Otorhinolaryngol.*, 17: 1-11 (1989).
Chang, K.W., "Intracapsular versus subcapsular coblation tonsillectomy," *Otolaryngol. Head Neck Surg.*, 138: 153-157 (2008).
Chole, R.A., et al., "Anatomical evidence of microbial biofilms in tonsillar tissues," *Arch. Otolaryngol. Head Neck Surg.*, 129: 634-636 (2003).
Colen, T.Y., et al., "Effect of intracapsular tonsillectomy on quality of life for children with obstructive sleep-disordered breathing," *Arch. Otolaryngol. Head Neck Surg.*, 134: 124-127 (2008).
Derkay, C.S., et al., "Post-tonsillectomy morbidity and quality of life in pediatric patients with obstructive tonsils and adenoid: microdebrider vs electrocautery," *Otolaryngol. Head Neck Surg.*, 134: 114-120 (2006).
Galland, B.C., et al., "Changes in behavior and attentional capacity after tonsillectomy," *Pediatr. Res.*, 59: 711-716 (2006).
Isaacson, G., et al., "Developmental anatomy of the tonsil and its implications for intracapsular tonsillectomy," *Int. J. Pediatr. Otorhinolaryngol.*, doi:0.1016/j.ijporl.2007.09.021 (2007).
Magdy, E.A., et al., "Coblation tonsillectomy: a prospective, double-blind, randomized, clinical and Histopathological comparison with dissection-ligation, monopolar electrocautery and laser tonsillectomies," *J. Laryngol. Otol.*, 122: 282-290 (2008).
Michel, R.G., et al., "Safety and efficacy of pressure-assisted tissue-welding tonsillectomy: a preliminary evaluation," *ENT-Ear, Nose & Throat Journal*, 87: 100-112 (2008).
Okuyucu, S., et al., "The effect of anesthetic agents on perioperative bleeding during tonsillectomy: Propofol-based versus desflurane-based anesthesia," *Otolaryngol. Head Neck Surg.*, 138: 158-161 (2008).
Özdemir, I., et al., "Measurement of tonsillar blood flow in normal and pathological conditions by the use of the $^{133}$Xe clearance technique," *Arch. Otorhinolaryngol.*, 242: 53-56 (1985).
Roth, J.A., et al., "Harmonic scalpel tonsillectomy versus monopolar diathermy tonsillectomy: a prospective study," *ENT—Ear, Nose & Throat J.*, 87: 346-349 (2008).

(56) References Cited

OTHER PUBLICATIONS

Salonen, A., et al., "Recovery after tonsillectomy in adults: a three-week followup study," *Laryngoscope*, 112: 94-98 (2002).
Shah, R.K., et al., "Optical-thermal simulation of tonsillar tissue irradiation," *Lasers Surg. Med.*, 28: 313-319 (2001).
Stearns, M., "The relationship between adenoid weight to tonsillar weight," *J. Laryngol. Otol.*, 97: 519-521 (1983).
Windfuhr, J.P., et al., "Life threatening posttonsillectomy hemorrhage," *Laryngoscope*, 118 (2008).
Young, T., et al., "Epidemiology of Obstructive Sleep Apnea," *Am. J. Respir. Crit. Care Med.*, 165: 1217-1239 (2002).
Allison, K.P., et al., "Pulsed dye laser treatment of superficial basal cell carcinoma: realistic or not?," *Lasers Med. Sci.*, 18: 125-6 (2003).
Au, J. L-S., et al., "Clinical Aspects of Drug Delivery to Tumors," *J. Control Rel.*, 78: 81-95 (2002).
Beutner, K.R., et al., "Effect of Pulsed Dye Laser on Basal Cell Carcinoma," *Lasers Surg. Med. Suppl.*, 14: 22 (2002).
Botteman, M.F., et al., "The Health Economics of Bladder Cancer," *Pharmacoeconomics*, 21(18): 1315-1330 (2003).
Campolmi, P., et al., "Vascular based non conventional dye laser treatment for basal cell carcinoma," *Dermatol. Ther.*, 21: 402-405 (2008).
Chen, D., et al., "Effect of Dimethyl Sulfoxide on Bladder Tissue Penetration of Intravesical Paclitaxel," *Clin. Cancer Res.*, 9: 363-369 (2003).
Christenson, L.J., et al., "Incidence of Basal Cell and Squamous Cell Carcinomas in a Population Younger Than 40 Years," *JAMA*, 294: 681-690 (2005).
Foley, P., et al., "Photodynamic therapy with methyl aminolevulinate for primary nodular basal cell carcinoma: results of two randomized studies," *Int. J. Dermatol.*, 48: 1236-1245 (2009).
Hallock, G.G. and Lutz, D.A., "A Prospective Study of the Accuracy of the Surgeon's Diagnosis and Significance of Positive Margins in Nonmelanoma Skin Cancers," *Plast. Reconstr. Surg.*, 107: 942-947 (2001).
Jemal, A., et al., "Cancer Statistics, 2008," *CA Cancer J. Clin.*, 58: 71-96 (2008).
Karim, M.A., et al., "Realization of a uniform circular source using a two-dimensional binary filter," *Optics Letters*, vol. 10, No. 10 (Oct. 1985).
Kretsos, K. and Kasting, G.B., "Dermal Capillary Clearance: Physiology and Modeling," *Skin Pharmacol. Physiol.*, 18: 55-74 (2005).
Lee, S-J., et al., "Bioadhesive Drug Delivery System Using Glyceryl Monooleate for the Intravesical Administration of Paclitaxel," *Chemotherapy*, 51: 311-318 (2005).
Love, W.E., et al., "Topical Imiquimod or Fluorouracil Therapy for Basal and Squamous Cell Carcinoma," *Arch. Dermatol.*, 145: 1431-1438 (2009).
Lu, Z., et al., "Paclitaxel-Loaded Gelatin Nanoparticles for Intravesical Bladder Cancer Therapy," *Clin. Cancer Res.*, 10: 7677-7684 (2004).
Overholt, B., et al., "Photodynamic Therapy for Esophageal Cancer Using a 180° Windowed Esophageal Balloon," *Lasers in Surgery and Medicine* 14:27-33 (1994).
Robinson, J.K. and Fisher, S.G., "Recurrent Basal Cell Carcinoma After Incomplete Resection," *Arch. Dermatol.*, 136: 1318-1324 (2000).
Shah, S.M., et al., "The Effect of 595 nm Pulsed Dye Laser on Superficial and Nodular Basal Cell Carcinomas," *Lasers Surg. Med.*, 41: 417-422 (2009).
Sukai, S.A., et al., "What Lies Beneath? A Lesson for the Clinician. Intraoperative Frozen Section Appearance of Persistent Basal Cell Carcinoma after Apparent Cure with Imiquimod 5% Cream," *Derm. Surg.*, 35: 1831-1834 (2009).
Tierney, E.P. and Hanke, C.W., "Cost Effective of Mohs Micrographic Surgery: Review of the Literature," *J. Drugs Dermatol.*, 8: 914-922 (2009).
Zijistra, W.G., et al., "Absorption Spectra of Human Fetal and Adult Oxyhemoglobin, De-Oxyhemoglobin, Carboxyhemoglobin, and Methemoglobin," *Clinical Chemistry* vol. 37, No. 9, 1633-1638 (1991).
Notification Concerning Transmittal of International Preliminary Report on Patentability for International Application No. PCT/US2009/065768 Dated Jun. 3, 2011.
Office Action from U.S. Appl. No. 12/625,335, filed Nov. 24, 2009 mailed Jun. 28, 2012.
Final Office Action from U.S. Appl. No. 12/625,335, filed Nov. 24, 2009 mailed Nov. 26, 2012.
Koechner, W. Solid-State Laser Engineering, $2^{nd}$ Ed., Springer-Verlag, pp. 251-253 (1988).
EP 09828386.4 Office Action dated Nov. 14, 2014 entitled "Photothermal Treatment of Soft Tissues".
U.S. Appl. No. 14/210,011 Office Action dated Jul. 16, 2014 entitled "Photothermal Treatment of Soft Tissues."

\* cited by examiner

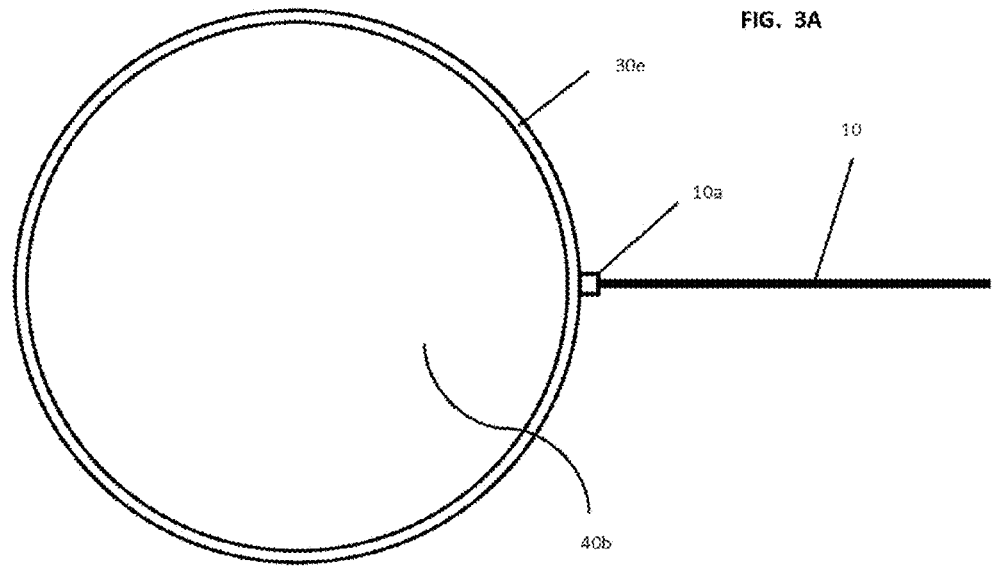
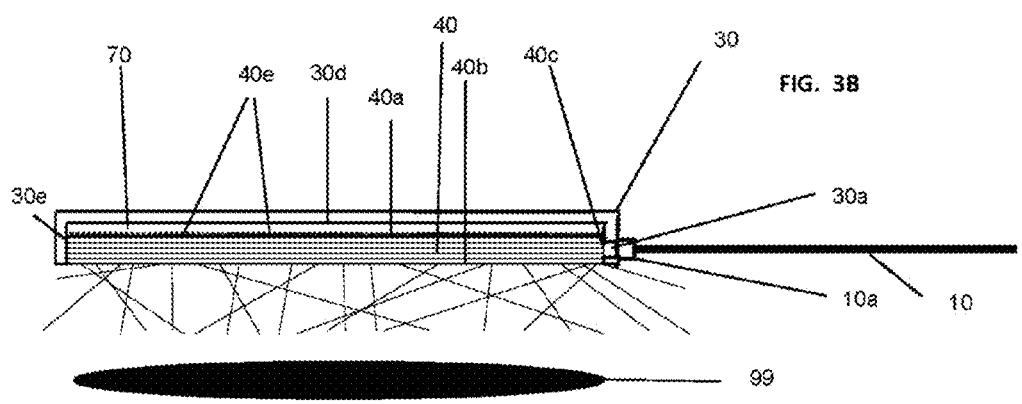

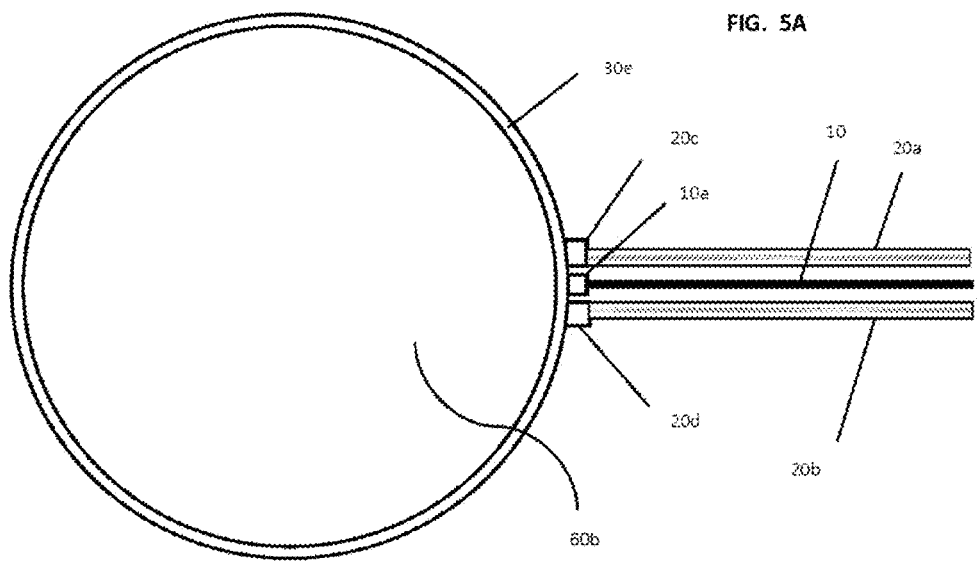
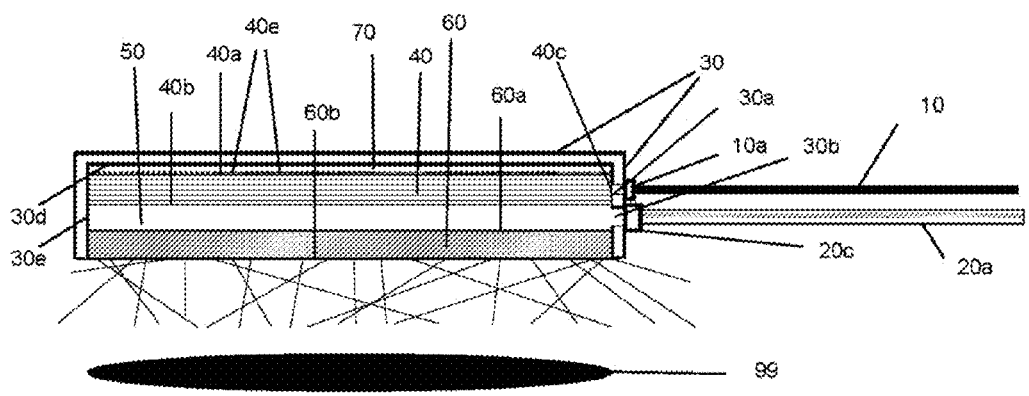

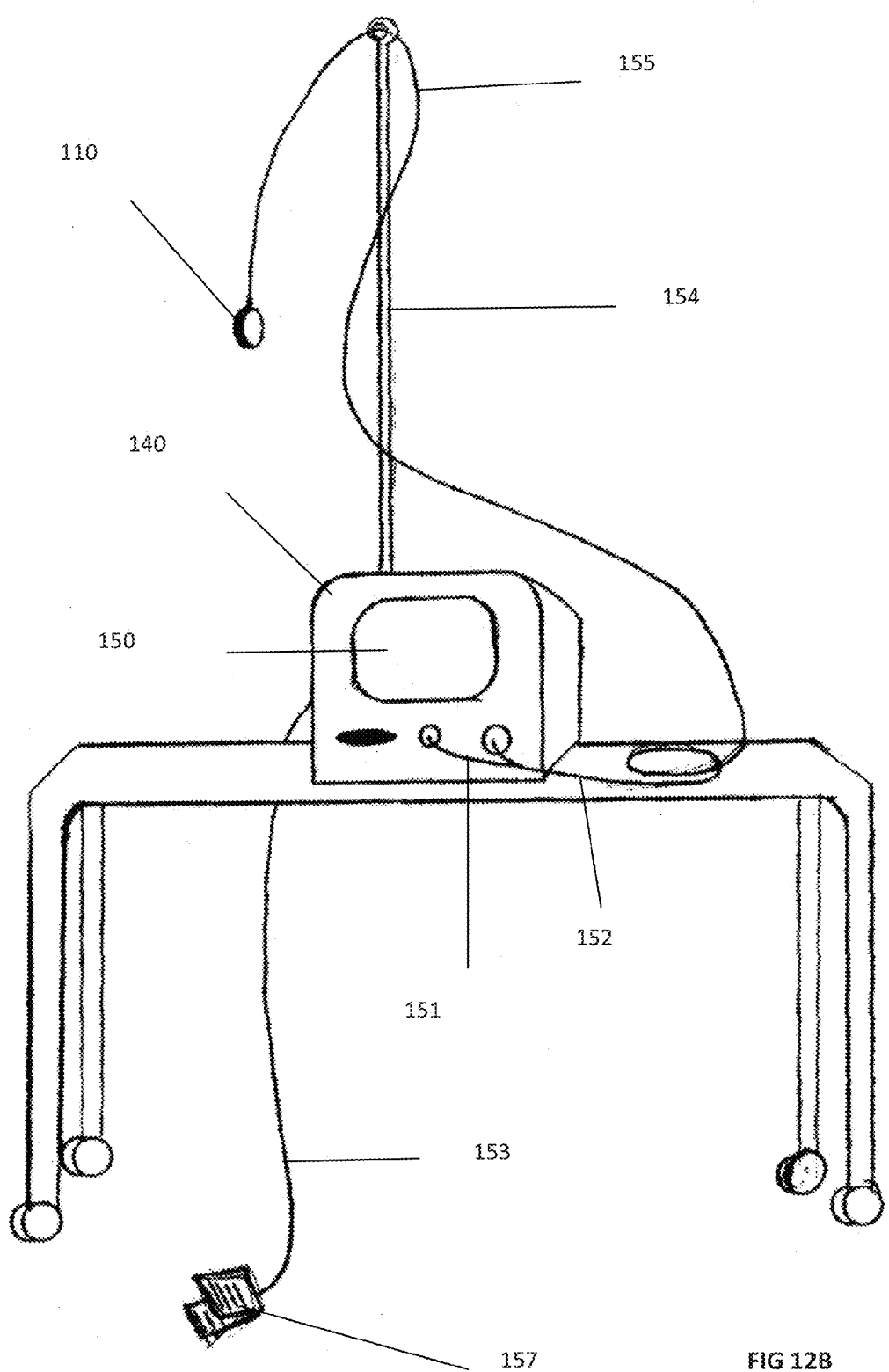

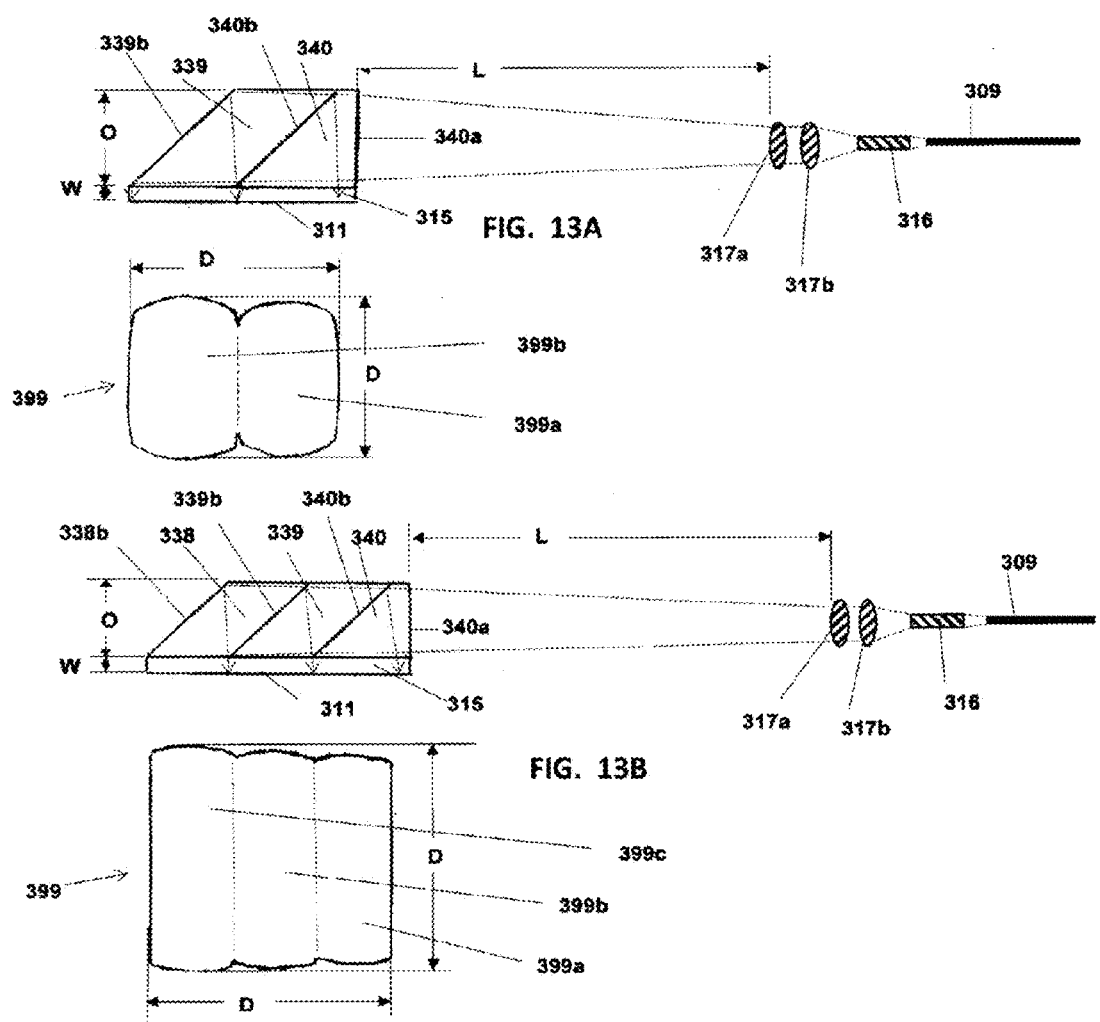

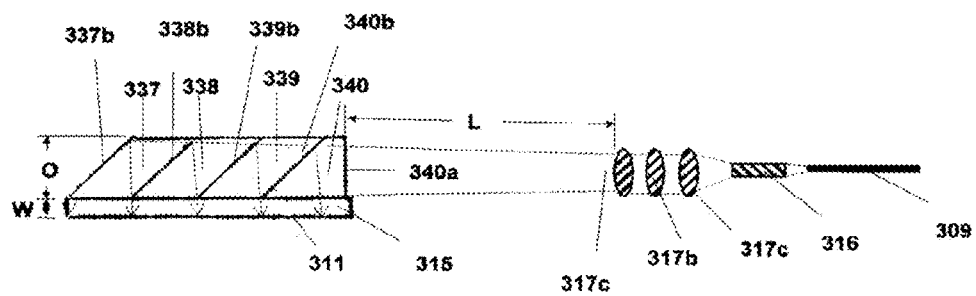
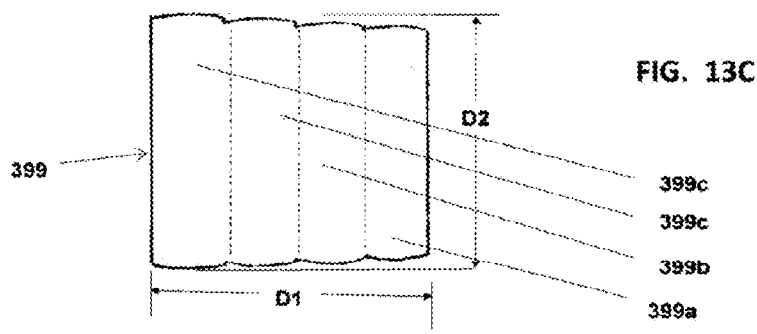
FIG. 13C
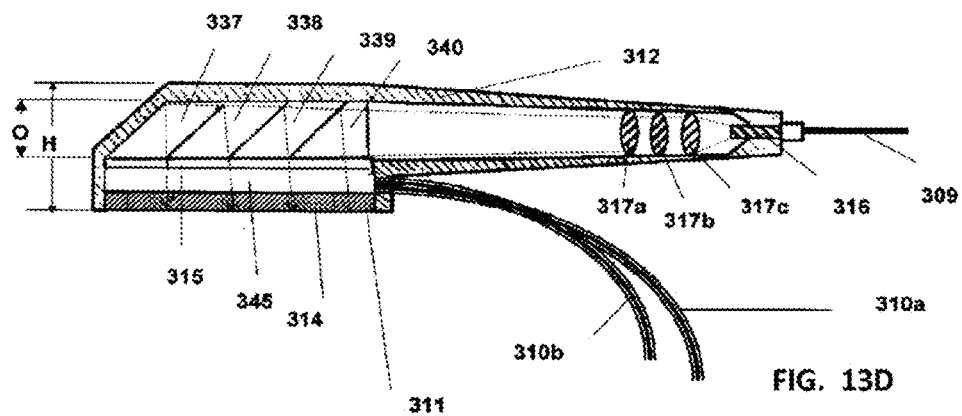
FIG. 13D

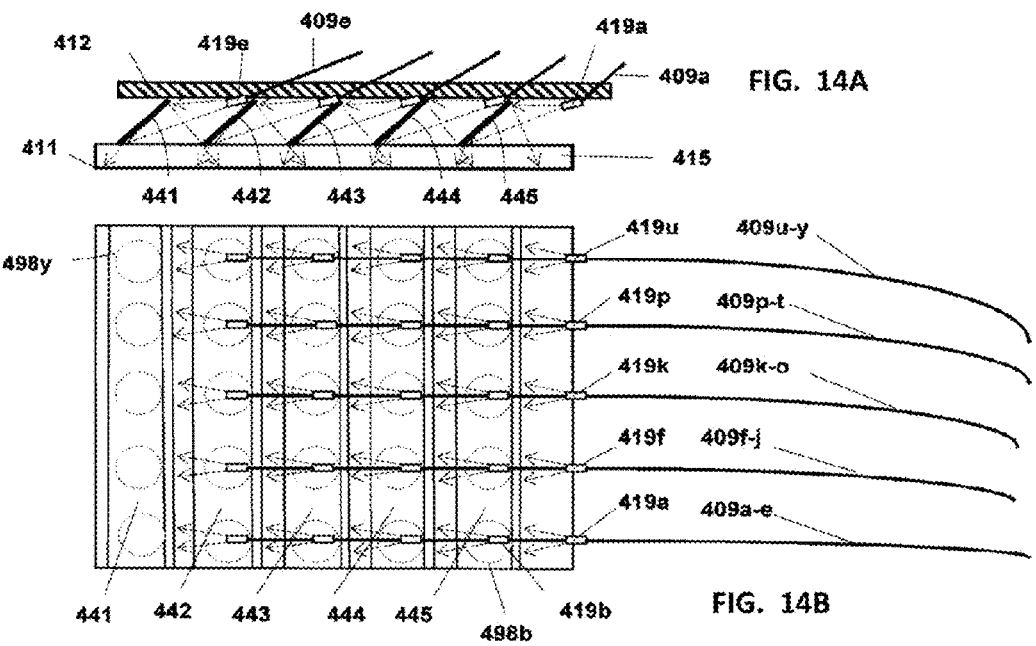
FIG. 14A
FIG. 14B
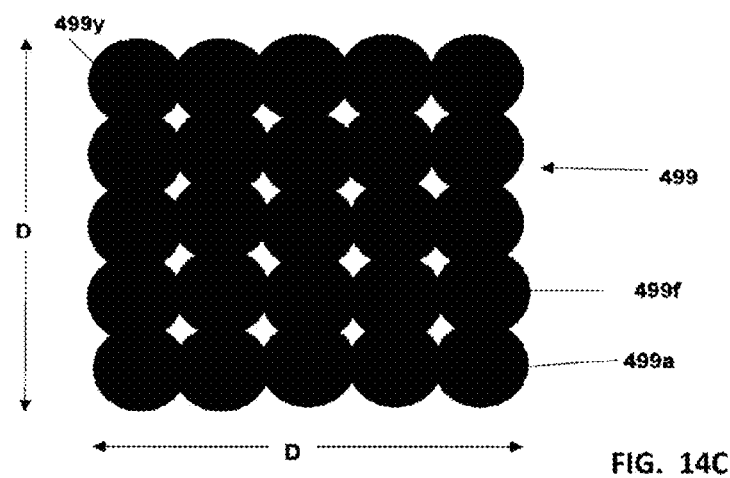
FIG. 14C

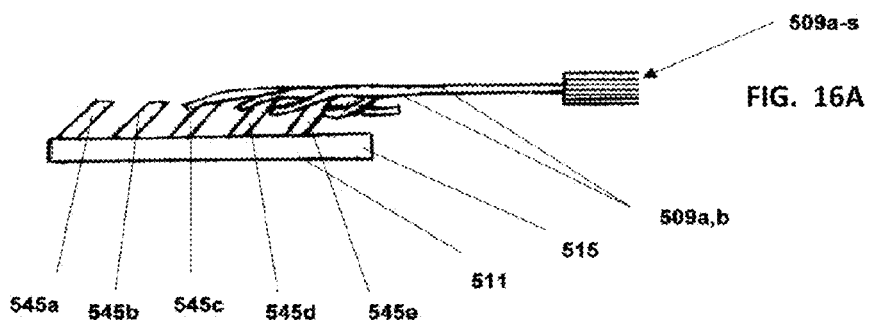
FIG. 16A
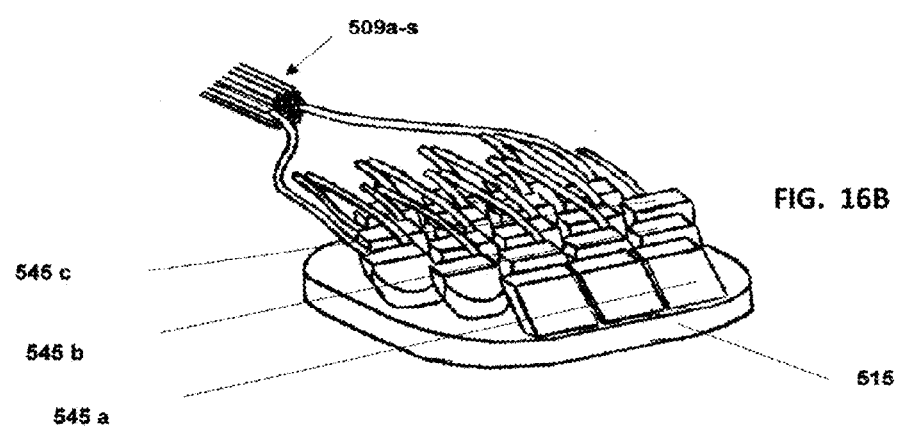
FIG. 16B
FIG. 16C
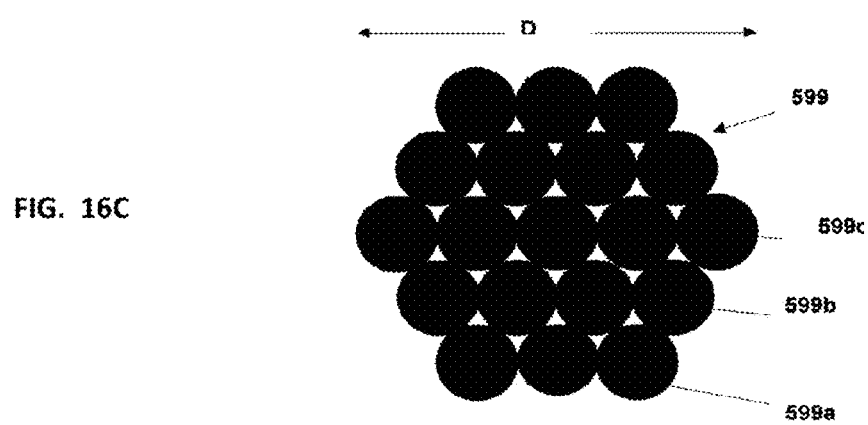

LOW PROFILE APPARATUS AND METHOD FOR PHOTOTHERAPY

RELATED APPLICATIONS

This application is a divisional of U.S. application Ser. No. 12/952,946, filed Nov. 23, 2010, which is a continuation-in-part of U.S. application Ser. No. 12/625,335, filed Nov. 24, 2009, which claims the benefit of U.S. Provisional Application No. 61/117,279, filed on Nov. 24, 2008. U.S. application Ser. No. 12/952,946 also claims the benefit of U.S. Provisional Application No. 61/264,161, filed Nov. 24, 2009. The entire teachings of the above applications are incorporated herein by reference.

BACKGROUND OF THE INVENTION

Phototherapy, defined herein as the use of light in the treatment of tissue in the human body, is a well established field of medicine. Light, defined as electromagnetic radiation of one or more wavelengths, may be used as the sole component of phototherapy, or phototherapy may involve the combination of light with drugs, dyes or other chemical agents, as well with radiofrequency, ultrasound, or other forms of energy. Phototherapy may also involve a combination of tissue temperature modification with the application of light, most frequently in the form of surface cooling. Many of the most important applications of phototherapy involve ablation, coagulation, denaturation or other heat-induced changes in the tissue.

In phototherapy, it is often desirable to expose an area of tissue to treatment. For example, it may be desirable to illuminate a surface area of the skin to treat a multitude of hair follicles associated with unwanted hair. It is often desirable that the area of tissue be exposed to light of substantially uniform distribution. These objectives of area irradiation and uniformity of distribution have been accomplished by reimaging the exit face of an optical fiber onto the tissue surface. Optical fibers are a commonly used transmission system for lasers. Handpieces designed to reimage the exit face of an optical fiber connected to a laser are well known in phototherapy, and design principles have been described (e.g., Hunter et al., Proc. SPIE Vol. 2993, pages 168-179, 1997). Such handpieces typically include at least two lenses disposed along an axis orthogonal to the surface to be irradiated. Because the fiber face has a very small area, a large magnification may be required for phototherapy of a large surface area. Consequently, handpieces commonly have a long axial length, typically of several centimeters, between the exit face of the optical fiber and the tissue surface to be exposed to light.

An example handpiece 1 is shown schematically in FIG. 1, where an optical fiber 2 is attached at one end to a light source (not shown) and at or near the other end by a connector 2a to the handpiece 1 comprising a cylindrical housing 4 that holds two plano-convex lenses 3 selected to reimage the exit face of the fiber 2b. The housing has an open end with a standoff 4a of a length that allows the handpiece to be positioned in contact with the tissue surface so that the light is substantially uniformly distributed over a circular area 5 at or near the image plane on the tissue surface. The axial length of the handpiece orthogonal to the tissue surface is very large compared to the diameter of the irradiated area of the tissue. To avoid light losses, the lenses and windows of the handpiece may be anti-reflection (AR) coated for the wavelength of the light source. A particular AR coating is effective over a limited range of wavelengths, consequently a handpiece may not be compatible with different light sources.

In some phototherapy handpieces, reimaging of the fiber exit face may be approximate, to reduce the axial length. Simpler phototherapy handpieces may have no lens or one lens, although the light distribution may have poor uniformity. In some cases, the handpiece may have the capability of cooling the treatment site, for example by transmitting the light from a source through a cooled window or lens in thermal contact with the treatment site, or by emitting a spray of cooling fluid onto the treatment site. The light passing through and emitted from a phototherapy handpiece may be substantially collimated, divergent or convergent, such that it travels approximately parallel to the long axis of the handpiece and approximately orthogonal to the tissue surface. Commercially available examples of phototherapy handpieces of this directed output type include the GentleLase and Vbeam laser handpieces produced by Candela Corporation (Wayland, Mass.) for removal of hair, and for treatment of cutaneous vascular lesions and aging skin, respectively.

Such handpieces require care on the part of the operator to maintain their orientation perpendicular to the treatment surface, for adequate uniformity of light distribution and tissue cooling. Furthermore, because of the diameter of the optics and length of their housing, as well as other components, for example tissue cooling systems, these handpieces are bulky, heavy, and may be awkward to hold. Operators frequently experience fatigue when performing long procedures. Furthermore, when employing active cooling for protection of superficial tissue layers from the effects of higher power light sources, it is necessary to use recirculating chillers, cryogen spray devices, thermoelectric coolers, cold air machines, and the like. These active cooling devices add cost and complexity, and in some cases use consumables, such as cryogen and gases.

Despite these known disadvantages of large, bulky handpieces, devices of this type continue to be in widespread use, particularly in dermatologic phototherapy, where uniformity of emitted light distribution is important. Fluences of a few to 100 $J/cm^2$ or higher can readily be achieved at the tissue surface, which makes these devices appropriate for relatively high power phototherapeutic procedures that involve ablating, coagulating, denaturing or otherwise thermally injuring tissue or tissue components. Such procedures may be highly efficacious. When pulse durations on the order of a few to hundreds of milliseconds are used, peak irradiances produced by these devices at the tissue surface may range up to several thousand $W/cm^2$ or higher. Bulky handpieces in present use can be designed to withstand high powers.

Phototherapy handpieces of the above-described type produce light of relatively uniform directionality. It is recognized that this directed output can readily damage the cornea or retina of the eye, and requires the use of eye protection by both operator and patient. Recently, phototherapy devices that emit diffuse light output have been described, as a means of providing increased eye safety. For example, Grove et al. (U.S. Pat. No. 7,452,356) have described a device with a hollow chamber or passageway through which light travels from a source, to an optical diffuser at the distal end. If light is accidentally emitted when directed towards the eye, the energy density at the eye will be low because of the scattered and highly divergent output of the handpiece.

In Weckwerth et al. (US 2006/0009749), light from a source is transmitted through opposing surfaces of a solid transparent light guide to an optical diffuser at the distal end of a handpiece. Alternatively, light may enter the light guide through a reflective diffuser, or the light guide itself may have diffusing input or output surfaces. Light propagates in a substantially forward direction through the light guide, that is, in a direction orthogonal to the tissue surface. These diffusing handpiece devices of Grove et al. and Weckwerth et al. provide enhanced eye safety, compared to phototherapy handpieces emitting directed light, and may contain a light source within the housing of the handpiece such that the entire apparatus is handheld. However, the direction of overall light propagation remains orthogonal to the tissue surface in these diffusing devices, and the handpieces are therefore still bulky and large compared to the dimension of the irradiated area on the tissue surface, and consequently have the disadvantages of the previously described phototherapy handpieces.

An example of a diffusing type device described by Weckwerth et al. (US 2006/0009749) is depicted schematically in FIG. 2. Light from an optical fiber (2) attached at one end to a light source (not shown) and at the other end to a reflective back surface (6), travels by total internal reflection (TIR) in a substantially forward direction through an elongated, slightly tapered light guide (7). Upon exiting the light guide, also in a substantially forward direction, the light impinges on optical diffuser (8) and is emitted through a window (9). Any portion of light reflected backwards at the light guide exit surface is reflected at back surface (6) and redirected in the forward direction again through the light guide. With proper design of the light guide and other optical components, the output distribution at the window may be substantially uniform. Since the light is scattered by the diffuser, the output will be low unless the surface to be irradiated is in contact with the window. The device described by Weckwerth et al. is intended to be used with the window in contact with the tissue to be treated. The dimensions of the irradiated area (5) are those of the output window (9).

In US 2007/0032847, Weckwerth et al. described a diffusing type device having a hollow chamber with reflective walls instead of a light guide. The length of the hollow chamber is 1 to 2 times the length of the output window on the device, for adequately uniform light distribution, according to the description in this application of Weckwerth et al.

A phototherapy device of the diffusing type is commercially available from TRIA Beauty (Pleasanton, Calif.). This device is a cordless handheld unit containing battery and light source that has been FDA cleared for hair removal. The overall dimensions of the TRIA device are large compared to the dimension of the output window, and active skin surface cooling technology such as fluid flow or cryogen spray, which would have further added to the weight and power requirements, is not incorporated into the device. The TRIA device produces a maximum irradiance of about approximately 30 W/cm$^2$ from a laser source operating at 800 nm. Without active skin cooling, the TRIA is limited to use by people with light skin and without suntans.

In other phototherapy applications, an array of light generating sources may be disposed over the tissue to provide irradiation of an area. Leber et al. (U.S. Pat. No. 6,860,896) described a device comprising a plurality or array of light-emitting diodes (LEDs) on a substrate, which can be brought in contact with the skin so that when the LEDs are sequentially activated the light traces acupuncture meridians, for a characteristically low power biostimulation effect. Russell (U.S. Pat. No. 6,290,713) has described a flexible low power illuminator using an array of LEDs surrounded by coolant channels to dissipate heat and prevent heat transfer to the treatment surface, and scattering elements such as bubbles, particles, or paint dots disposed between the light sources and the treatment surface to homogenize the distribution of light from the plurality of emitters. The device may be placed in contact with skin for phototherapy, and produces an average irradiance described as preferably at least 50 milliwatts/cm$^2$. An array of diode lasers disposed in a flexible bandage or implantable disc and electrically connected to a power supply has been described by Prescott (WO 98/43703) for low level laser irradiation to stimulate healing of myocardium.

An array of sources overlying the treatment site may provide a means of performing phototherapy with a relatively thin, low profile optical assembly. The source array approach is currently limited to low power applications, however, such as biostimulation. Other disadvantages of the source array approach are complexity, the need for electrical connection to each source, management of waste heat generated by the light sources in proximity to the treatment surface, and the potential hazards of electrical current in proximity to the treatment surface and of explosive failure of the light generating sources. Therapeutic applications of the source array approach are limited by relatively low powers produced by the arrays.

Another approach involves the use of fiber optic mats or patches made of woven optical fibers, where bends in the optical fibers serve as regions of light leakage. The average irradiance that can be achieved at the mat surface is low. Yet another approach is to produce light inside a thin layer that can be disposed over the treatment site, for example by electroluminescence (Holloway et al. (U.S. Pat. No. 7,304,201)) or chemiluminescence (Zelickson et al. (US 2005/0080465)). These approaches are also significantly limited in output power.

Therefore, despite the numerous devices and methods for applying light to an area of tissue using handpieces, arrays, patches, and light guides, there remain substantial longstanding limitations. The available devices for uniformly irradiating surface areas of tissue are large and bulky when capable of high power treatment. Thin, flat, low profile devices of the prior art, which may include some flexible patches, mats, and arrays, are limited to low power applications. The low power limitation of the low profile optical assemblies of the prior art precludes their use for ablation, coagulation, denaturation, or other thermal modification of tissue. This limitation of the prior art low profile devices precludes many of the most effective and well established phototherapeutic treatments, such as hair removal, vascular lesion eradication, pigmented lesion eradication, acne treatment, tattoo treatment, scar treatment, and many others.

For treatments that involve irradiation of superficial tissue of a lumen or hollow organ of the body, current technology also has significant limitations. Light can be delivered using an optical fiber positioned within the lumen and irradiating over a wide range of angles toward the luminal walls, for example, but the light intensity at a given point on the luminal wall is affected by reflections, and also by the distance between the irradiating fiber tip and said point. Consequently, fibers have been centered in the lumen using balloons and the like, but the light intensity at the level of the fiber tip, whether it is a point source, sphere, cylinder, etc., is higher than above or below said level. The tip or the balloon can be filled with a diffusively scattering fluid medium, such that light intensity at its surface is more uniform, but losses are high with multiple scattering through long distances in said medium and the transmission efficiency is poor.

Furthermore, such technology is not well suited for delivering the high irradiances required for ablative or coagulative treatments. To ablate in a single light exposure the entire surface area of a lumen affected by a disease, for example, a very high power light source may be required. Treatment of a lumen or hollow organ with light can be done when light requirements are relatively low, for example in photodynamic therapy (PDT), where light is delivered at nonthermal levels to activate a drug, although variable and inconsistent light dosages at the tissue surface remain problematic and may lead to adverse effects, such as strictures, as well as ineffective treatment with recurrences. Alternatively, to ablate superficial tissue in a lumen or hollow organ, a directable optical fiber delivery system, with or without a contact tip, can be used to deliver high irradiances to one section of the affected area at a time. Disadvantages of that segmental approach are that it is time consuming, and it is difficult to avoid overlapping or missed segments.

Limitations in the current technology have limited the application of phototherapy in treatment of lumens and hollow organs. For example, there is the problem of treating Barrett's esophagus (BE) in patients with gastrointestinal reflux disease (GERD), and high grade dysplasia of the esophagus. GERD leads to premalignant changes in the normal squamous epithelium of the distal esophagus. BE is the only known precursor lesion for esophageal adenocarcinoma, the incidence of which has increased by 300 to 500% in the past four decades (Anandasabapathy S, Gastrointest Cancer Res 2:81-84, 2008). Considerable effort has been made over many years to develop PDT for BE. However, difficulties in light delivery as outlined above have contributed to unsatisfactory outcomes, and PDT has not developed into a standard treatment of esophageal disease.

Recently, a balloon radiofrequency device has been developed for treatment of BE and other esophageal diseases. In that device, an array or arrays of electrodes attached to a catheter is positioned at the esophageal surface using a balloon, and the electrode energized to ablate the mucosa. However, disadvantages remain. The surface array design is specific for radiofrequency, and does not enable use of energy in the form of light. With radiofrequency, control over ablation depth must be obtained by choice of power and pulse width. Depth of radiofrequency ablation cannot be controlled as it is with light, where the tissue optical properties of scattering, absorption and anisotropy determine the depth of penetration of a given wavelength. Tissue effects are limited to nonselective thermal destruction in radiofrequency, unlike irradiation with light using wavelengths selectively absorbed by specific tissue components. The electrode arrays must be in full contact with tissue to avoid injury when activated. Furthermore, the tissue-contacting radiofrequency ablation catheters are single use disposables costing approximately $2700 and $1800 for 360° and 90° ablations, respectively, to be used with a $900 disposable sizing balloon. Consequently, radiofrequency ablations performed in an outpatient clinic with the patient under sedation can be nearly as costly as a surgical esophagectomy performed in the operating MOM.

Thus, light is not part of the current armamentarium in treating patients with esophageal disease including BE, despite inherent advantages of light based treatments, either with or without a photodynamic drug, over other less flexible and less precise forms of energy such as radiofrequency.

SUMMARY OF THE INVENTION

Embodiments of the present invention include a phototherapy apparatus comprising an optical assembly having a thin, low profile shape. More particularly, embodiments include a low profile optical assembly that may be used with fiber coupled lasers and other light sources, including high power sources, and that emits light with substantial uniformity. Some examples include to a low profile optical assembly with capability for cooling skin, such as a detachable, reusable heat sink for active cooling without consumables, fluid pumps, or other cooling equipment.

Example apparatus can be used to treat superficial tissue of a lumen or hollow organ with light, at irradiances that are ablative or coagulative, with substantial uniformity. They may include a light source selected such that its wavelength is advantageous for a desired tissue effect, such as ablation or coagulation to a target depth, denaturation, thermal modification of a tissue, and/or preferential injury to a target tissue structure. For example, they can be used to produce a uniform distribution of light at a surface of mucosal tissues, for a highly advantageous treatment of internal or luminal tissue including Barrett's esophagus. Examples include reusable optical assemblies with disposable protective sleeves.

Example phototherapy apparatus may also have enhanced eye safety (e.g., by emitting light with a substantially Lambertian distribution) and may be advantageous for medical, aesthetic, and home use treatment of the skin. These examples may include an optical assembly that may be used with light sources having different wavelengths.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3A and 3B are schematic drawings of a first optical assembly.

FIGS. 5A and 5B are schematic drawings of a second optical assembly.

FIG. 12B is a schematic drawing of a simple apparatus having a single optical assembly.

FIGS. 13A-13D are drawings of a ninth optical assembly that includes a plurality of prisms.

FIGS. 14A-14C depict a tenth optical assembly that includes a plurality of elongated mirrors for light reflection.

FIGS. 16A-16C show an eleventh optical assembly that includes an array of fiber coupled mirrors.

FIG. 20A depicts the optical assembly housing. FIG. 20B depicts the elements of the optical assembly. FIG. 20C depicts the light guide plate with extraction features. FIG. 20D shows the irradiance diagram for the optical assembly of the first example.

FIG. 21A depicts the optical assembly housing. FIG. 21B depicts the elements of the optical assembly. FIG. 21C depicts the light guide plate with extraction features. FIG. 21D shows the irradiance diagram for the optical assembly of the second example.

FIG. 22A depicts the optical assembly housing. FIG. 22B depicts the elements of the optical assembly. FIGS. 22C and 22D depict the light guide plate with coatings of the lateral walls. FIG. 22E depicts the extraction features of the light guide plate. FIG. 22F shows the irradiance diagram for the optical assembly of the third example. FIG. 22G shows the irradiance diagram for the optical assembly of the third example, when extraction features are not applied.

FIG. 23A depicts the optical assembly housing. FIG. 23B depicts the elements of the optical assembly. FIG. 23C depicts the light guide plate with extraction features. FIG. 23D shows the irradiance diagram for the optical assembly of the fourth example.

DETAILED DESCRIPTION OF THE INVENTION

Figure 1:
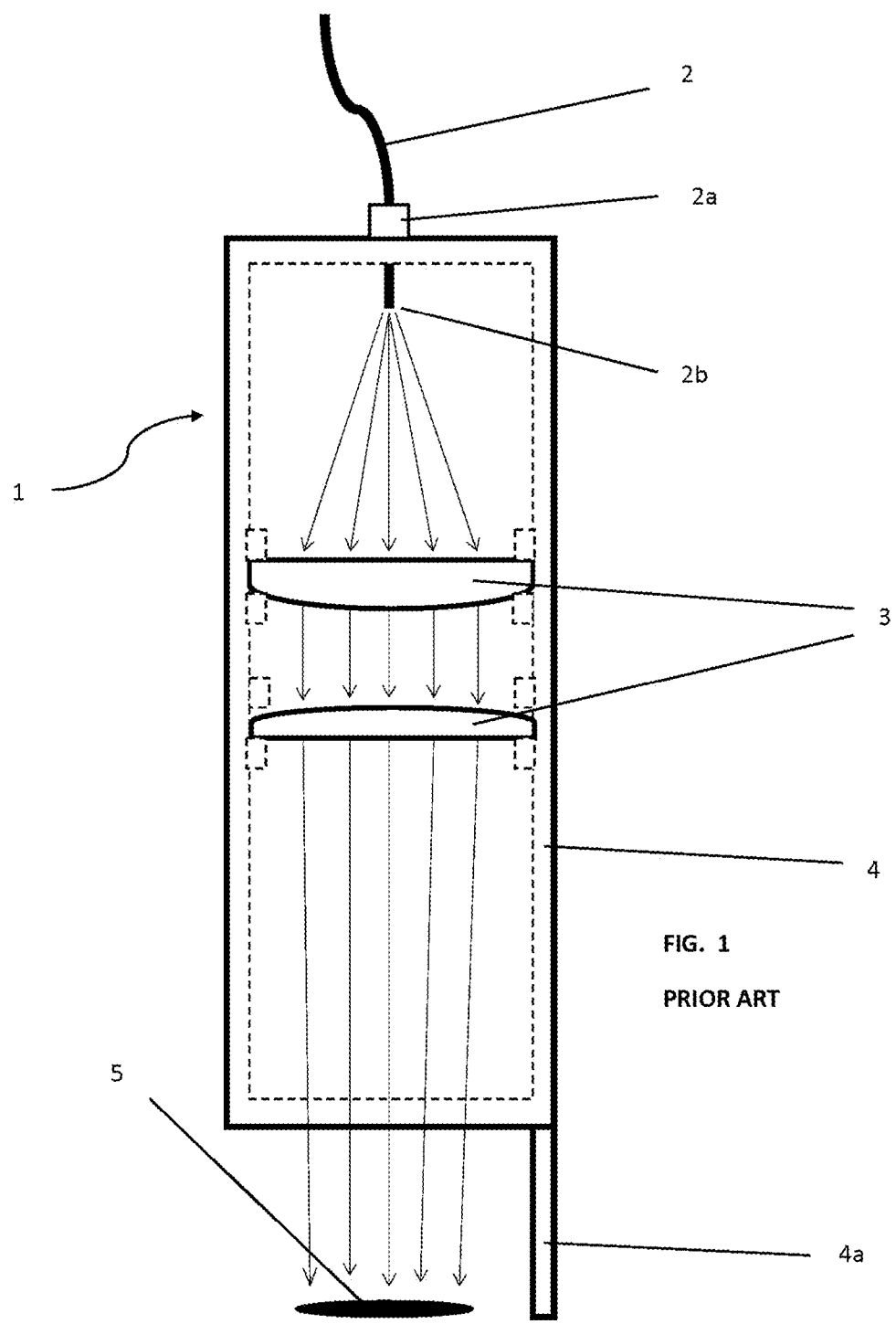
FIG. 1 is a schematic drawing of a handpiece of the prior art having a directed output.
Figure 2:
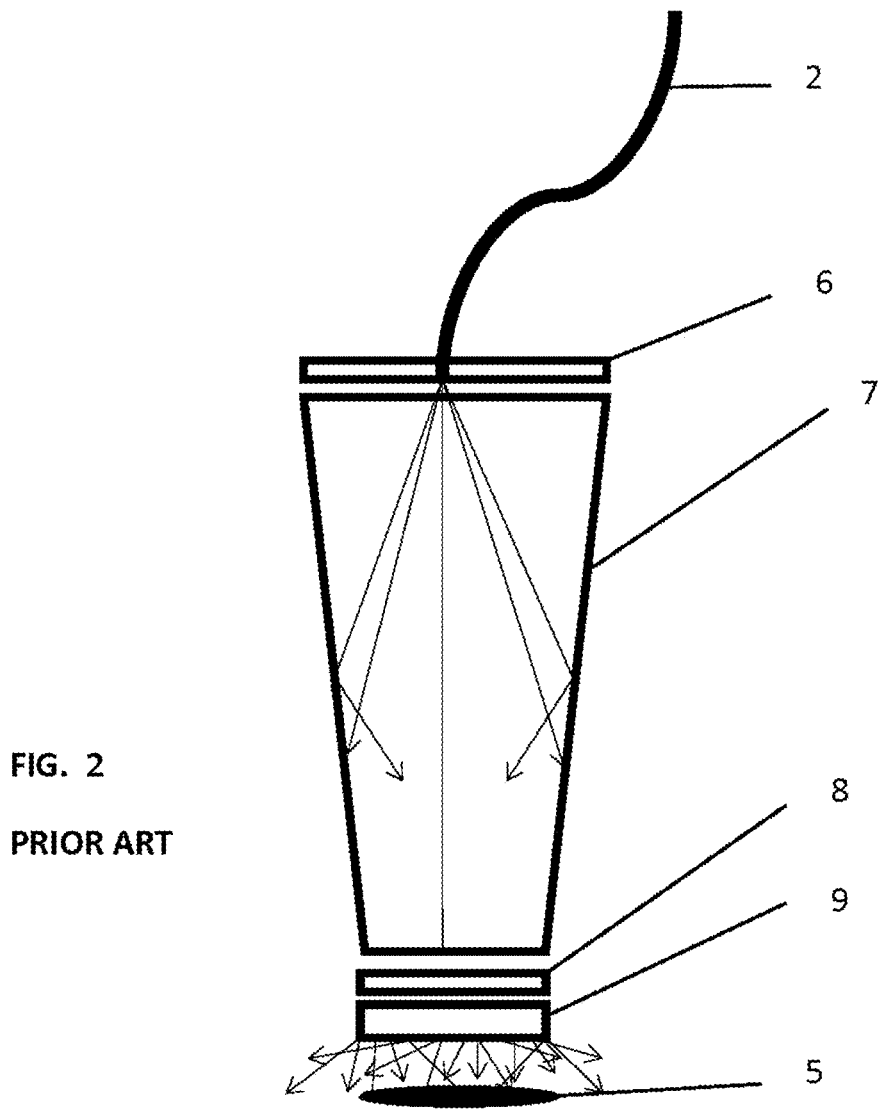
FIG. 2 is a schematic drawing of a diffusely scattering handpiece of the prior art.

A description of example embodiments of the invention follows. The teachings of all patents, published applications and references cited herein are incorporated by reference in their entirety.

Disclosed herein are apparatus for irradiation of an area of tissue on or in the human body. In particular, these apparatus may be used for irradiation of human tissue and may include an optical assembly that has a light-emitting contact surface. The optical assembly is advantageously thin and light. In advantageous embodiments, the optical assembly comprises a light guide plate having a pattern of extraction features on at least one surface. An optical fiber may transmit light to a lateral input surface of a light guide plate of the optical assembly, such that the light propagates transversely within the light guide plate, in a direction that is substantially parallel to the tissue surface.

The optical assembly may distribute the light output of an optical fiber over a contact surface of an optical element of the optical assembly, such that when the contact surface is placed adjacent to the area of tissue to be irradiated, the contact surface emits light to irradiate the area of tissue. The contact surface is substantially parallel to the light guide plate and has a surface area that is large compared to the cross-sectional area of said optical fiber. The light emitted from the contact surface, which can be a surface of the light guide plate, may be of substantially uniform irradiance. In advantageous embodiments, the light-emitting contact surface is actively cooled.

Embodiments provide for a highly advantageous and efficient coupling of a light source to a light-emitting contact surface of an optical assembly. The apparatus may comprise a single optical assembly, multiple optical assemblies, or interchangeable optical assemblies of different contact surface area or shape. It is found herein that an optical assembly can be operated over a wide range of light wavelengths, such that said optical assembly may be used with different light sources, light sources operating at more than one wavelength, or interchangeable light sources.

An optical assembly may have a light-emitting contact surface that is circular, oval, square, hexagonal, elliptical, or any other geometric or nongeometric shape that is advantageous for phototherapy. Some embodiments concern the irradiation of human tissue with a least one optical assembly producing a substantially Lambertian distribution of light from the contact surface. Other embodiments concern the irradiation of human tissue with light of substantially uniform directionality from the contact surface.

Embodiments are also readily adapted to produce irradiated areas of a range of dimensions on a tissue surface, with the maximum area limited only by the power of the light source of the apparatus, such that the optical assembly remains advantageously thin regardless of the area of the light-emitting contact surface.

In some embodiments, an optical assembly of the apparatus is adapted to have a plurality of non-contiguous light-emitting contact surfaces, each surface with substantially uniform irradiance, such that tissue is irradiated in a fractional manner.

Some apparatus can be used to apply light from light-emitting contact surfaces that cool the tissue during irradiation. In advantageous embodiments, the contact surface actively cools the tissue during irradiation. In some highly advantageous embodiments, the light-emitting contact surface is cooled by flowing a liquid or gas through the optical assembly or through the housing of the optical assembly. In other highly advantageous embodiments, the light-emitting contact surface is cooled by a heat sink that is in a solid, liquid, or gel state, or some combination of said states, during irradiation of the tissue. Said heat sink is adjacent to the housing and in thermal contact with the optical assembly, but external to the beam path, during irradiation. In highly advantageous embodiments, the heat sink can be repeatedly reused by a process in which it is detached from the apparatus, chilled, reattached to cool the light-emitting contact surface during irradiation, detached after the procedure is complete, and chilled again as necessary for a subsequent procedure.

Another example can use pulsed or continuous wave (CW) light sources. The apparatus can comprise incoherent light sources, such as LEDs or lamps, having output that can be transmitted through an optical transmission element such as an optical fiber or light guide to an optical assembly of the device. In some preferred embodiments, the apparatus comprises a coherent light source or laser, which is coupled to or comprises an optical fiber or other optical transmission element. Lasers that may be used include diode lasers, including but not limited to AlGaAs and InGaAsP diode lasers, InAs/GaAs quantum dot diode lasers, solid state lasers such as alexandrite, neodymium YAG, holmium YAG, thulium YAG, ytterbium YAG, erbium glass, titanium sapphire, and KTP, pulsed dye lasers, excimer lasers, fiber lasers, Q-switched lasers, and any other laser operating in the ultraviolet, visible, or near-infrared spectral regions. High peak power lasers, for example pulsed dye lasers for vascular lesion treatment and alexandrite lasers for hair removal, may also be used.

Herein, for any optical element of an optical assembly, said element having two opposing surfaces, the surface that is closer to the light-emitting contact surface of the optical assembly, or which is a light-emitting contact surface, is referred to as the distal surface of said optical element. Likewise, the surface that is further from the a light-emitting contact surface of the optical assembly is referred to as the proximal surface of the optical element. The optical elements exposed to light from the optical fiber, including light guide plate, windows, and other optical elements, as well as air gaps and fluid layers located between the optical elements, and as positioned and contained at least partially within the housing of the optical assembly, are collectively referred to herein as the optical assembly. The optical assembly has as its boundaries the light-emitting contact surface of the distal end, and on the proximal end a substantially reflective surface. In some embodiments said substantially reflective boundary surface is an interior surface of the housing. In other embodiments the substantially reflective boundary surface is a light reflecting plate. The apparatus may comprise one or more optical assembly.

Disclosed herein are two types of optical assemblies: (1) optical assemblies that contain a substantially rigid light guide plate with diffusing extraction features, and (2) optical assemblies that contain a plurality of reflecting elements. Details regarding assemblies of the reflecting type are described in a later section. Optical assemblies with a light guide plate design are highly advantageous due to the minimal number of optical elements they comprise, facilitating their manufacture and reducing cost. The light guide plate accepts light at a lateral edge from an optical fiber and provides a path for transverse propagation by total internal reflection (TIR). TIR is achieved in the light guide plate by specular reflectance at surfaces of said plate in contact with a material or materials having lower refractive index $n_d$ than the light guide plate itself. The ability of the light guide plate to propagate light by TIR is improved as the difference between the $n_d$ of the plate and that of materials it is in contact with is increased. The light guide plate can be substantially transparent to light emitted by the light source, and may be formed of a rigid material or it may be a fluid or nonsolid layer bounded and constrained by adjacent rigid optical elements.

The optical assembly also comprises a light-emitting contact surface. In some embodiments, the light-emitting contact surface is in contact with tissue when the apparatus is irradiating a tissue surface. In other advantageous, a disposable sleeve may be disposed between the tissue and the optical assembly, such that the light-emitting contact surface is in contact with the disposable sleeve when irradiating a tissue surface. In some embodiments, light is transmitted from the distal surface of the light guide plate to a contact surface of a window element that is in contact with the tissue and that is substantially parallel to the light guide plate. In some embodiments the contact surface is a surface of the light guide plate. The light guide plate may be planar, with plane parallel distal and proximal surfaces, or said plate may have planar surfaces formed at an angle for a wedged shape. In other embodiments, one or both of the distal and proximal surfaces of the light guide plate may be nonplanar, having a convex, concave, or any other advantageous shape, such that the area of each of said surfaces is large compared to the output surface of the distal end of the optical fiber, and such that the propagation of light from the lateral input edge is in a direction substantially parallel to the tissue surface. Using a substantially rigid light guide plate reduces effects of the conformation of tissue surface being treated on the transmission efficiency and uniformity of irradiance from the optical assembly.

The light guide plate of the invention has extraction features that serve to disrupt TIR during transverse propagation and distribute light over the contact surface with substantial uniformity. Extraction features may be formed by removal of material from the light guide plate, for example as etched, ground, milled, machined or laser-ablated depressions, holes, dots, lines, or grooves. Because light spreads as it traverses the light guide plate from the input edge, the extraction features are applied in a pattern or distribution with spatial variation. For example, in regions of the light guide plate where light intensity is relatively high, such as in the vicinity of the input, a lower number or density of extraction features may be required.

Extraction features may also be formed by application of material to the surface of the light guide plate, for example reflective, scattering, or diffusive material applied to said surface in a pattern or distribution of dots, lines, or spots. Said applied materials may comprise diffusely reflective coatings, paints or other formulations comprising a particulate substance. Particulate substances may include substances with relatively high refractive index, such as barium sulfate, titanium dioxide, cerium oxide, tantalum oxide, magnesium oxide, aluminum oxide, high index glass, and the like, and mixtures of these substances. The particulate substance does not substantially absorb light from the light source of the apparatus. The applied material also contains a binder that serves to bind the particles of a particulate substance together and to a substrate, in the present case the light guide plate. In addition to providing mechanical stability of the applied material, the binder also serves to couple light out of the light guide plate and into the applied material, by disrupting TIR. Once in the applied material, light is diffusely scattered by the high index particles of the particulate substance.

The binder may be an organic substance such polyvinyl alcohol (PVA), polyvinyl acetate, urethanes, cellulose, polymethylmethacrylate, or the like. The applied material may be formulated with a solvent that evaporates after application. For example, a barium sulfate coating with very high diffuse reflectance throughout the visible and near-infrared spectral regions can be made by mixing 55.2% barium sulfate, 0.4% PVA, 27.2% water, and 17.2% ethanol, by weight. The ethanol is included in this formulation to inhibit aggregation of the particulate substance. After drying, the applied material comprises barium sulfate and PVA. Alternatively, the binder in an applied material may be an inorganic substance such as a salt or ionic compound. In these formulations, the binder crystallizes in the particulate interstitial space. For example, a mixture of 7.4% ammonium sulfate, 37% barium sulfate, and 55.5% (by weight) water makes an applied material that is completely inorganic and that is highly reflective.

Light guide plates with extraction features are commonly used in backlights for cell phones, computer displays, and flat screen televisions. Light guide plates have been in common use for visual displays for decades, but have not been used for phototherapy to ablate, coagulate, or thermally alter tissue until now. This may be because a backlight or light guide plate for a tissue ablation device has substantially different requirements than a backlight or light guide plate for a visual display.

As noted above, the binder is in contact with the light guide surface, and serves to couple light out of said light guide so that it is diffusely reflected by the particles. In advantageous implementations, the binder has an index of refraction $n_d$ that is higher than or approximately equal to the refractive index of the light guide plate, so that light traversing the light guide and impinging on an area of light guide surface with applied material exit into the binder. If the binder has an index that is substantially less than that of the light guide plate, some of the light impinging on the surface with applied material may be internally reflected, and only some may escape to be diffusely reflected by the particulate substance. Consequently, the applied material is less effective in disrupting TIR, and hence in directing light out of the light guide plate and into the tissue being irradiated.

Scattering occurs in a formulation comprising a particulate and a binder, when the particulate substance has a high index of refraction compared to the binder. In advantageous embodiments, diffuse reflectance by the applied material is increased by a relatively large difference in index between the particulate and the binder.

Therefore, according to example embodiments, a highly advantageous applied material comprises a particulate substance with a high refractive index, and a binder that has an index that is approximately equal to the index of the light guide, and lower than that of the particulate substance. Most advantageously, the particulate substance has a refractive index that is at least about 0.1 greater than that of the binder. Also, the binder and the particulate substance of the applied material do not substantially absorb the wavelength of the light source. In advantageous embodiments, the applied material of the extraction features has a reflectivity of at least approximately 95% at the wavelength or wavelengths.

In addition to extraction features made by removal of material or application of material, the extraction features of the light guide plate may be made by a molding process, or by a combination of molding, removal, and/or application of material.

Example light guide plates may be made of optical quality plastic, fused silica, quartz, glass or a crystalline material such as sapphire. In embodiments where the light-emitting contact surface is the distal surface of the light guide plate, it is advantageous for the light guide plate to have sufficient thickness, and to be made of material with sufficient strength, that said plate is substantially unbreakable during normal use. In highly advantageous embodiments the light guide plate thickness is not substantially greater than necessary to accept light at a lateral input edge from the light transmitting element. A thinner light guide reduces the number of scattering events within said guide, increasing transmission efficiency, as well as providing an advantageously thin optical assembly.

In some embodiments, it is highly advantageous to use a sapphire light guide plate. Sapphire has a high refractive index (1.76), a very high thermal conductivity (58 W/m K), and is very strong (flexure strength 1200 MPa). Sapphire cannot be molded, but extraction features can be made using diamond drills, or with laser ablation, with or without chemical etching. For extraction features made with applied materials however, existing formulations are poorly suited for sapphire. Binders known in the art have refractive indices substantially lower than that of sapphire. For example, $n_d$ for PVA is 1.50, whereas for sapphire $n_d$=1.76, and PVA will be ineffective in disrupting TIR with a sapphire light guide plate. To implement an advantageous sapphire light guide plate with applied material for extraction features, a new binder formulated with $n_d$ of about 1.76 is required. According to this example, a new binder material is made by mixing a standard binder, such as PVA, with inorganic nanoparticles of a very high index material.

For example, the nanoparticles may be zirconium oxide ($n_d$=2.2). The proportion of standard polymer binder and nanoparticles required for the new binder is determined according to the following equation:

$$n_d(\text{binder})=n_d(\text{polymer})\times \text{vol}(\text{polymer})+n_d(\text{nano})\times \text{vol}(\text{nano}), \quad (1)$$

where vol(x) is the volume fraction of substance x. Hence, an index matching binder for sapphire may be made with 0.629 vol % PVA, and 0.371 vol % zirconium oxide nanoparticles. Zirconium oxide nanoparticles are commercially available (for example, READE Advanced Materials, Providence, R.I.). Nanoparticles of diameter of about 25 to 50 nm or smaller are advantageous. A binder may be made, for example, by sonicating the nanoparticles in an aqueous solution of PVA until well dispersed. Then, an applied material suitable for sapphire light guide plates may be made by mixing the new binder with a particulate substance comprising larger (for example, about 1 to 3 micron diameter) zirconium oxide particles. In another example, an aqueous solution of coated nanoparticles, such as coated zirconium oxide nanoparticles, or vinyl coated zirconium oxide nanoparticles, can be mixed with PVA or other polymeric material to formulate a new high refractive index binder. In some embodiments, extraction features comprising applied material may be easier or less expensive to manufacture than extraction features made by removal of material from the light guide plate.

According to another inventive aspect, the optical assembly is made as thin as possible. Minimizing the thickness of the optical assembly reduces the number of scattering events and mean pathlength of photons between the optical fiber distal end and the contact surface, resulting in improved efficiency of the optical assembly, as well as making said assembly advantageously low profile. In embodiments comprising an external heat sink, minimizing the thickness of the optical assembly improves heat transfer and surface cooling.

In yet another aspect, the size, shape, pattern or distribution of extraction features is selected to produce a substantially uniform irradiance at the contact surface. In another aspect of the invention, the pattern or distribution of extraction features is selected to produce high transmission efficiency and a substantially uniform irradiance at the contact surface. In advantageous embodiments, transmission efficiency is 50% or higher. In highly advantageous embodiments, transmission efficiency is 80% or higher. In advantageous embodiments, irradiance at the contact surface has uniformity of approximately +25% to −25% or better. In highly advantageous embodiments, said irradiance has uniformity of approximately +10% to −10% or better.

In advantageous embodiments, the numerical aperture (NA) of the optical fiber is selected so that the light beam spreads to fill a substantial fraction of the width of the guide before reaching the edge opposite the input edge. In more advantageous embodiments, the output of an optical fiber directed to the lateral input edge of the light guide plate has sufficiently high NA that the light expands to substantially completely fill the width of the light guide by the time the opposing edge of said light guide is reached. In some embodiments, optical components such as lenses including anamorphic lenses may be inserted between the exit face of the optical fiber and the lateral input surface of the light guide plate.

The light-emitting contact surface of the optical assembly is in thermal contact with the tissue surface during irradiation. Heat generated in the tissue by absorption of light during irradiation is transferred from the tissue to one or more elements of the optical assembly, in a passive process. In advantageous embodiments, the optical element of the contact surface of a passively cooling optical assembly may be fused silica, quartz, glass or sapphire. More advantageously, the optical element of the contact surface of a passively cooling optical assembly is made of sapphire. When the optical element is fused silica, quartz, or glass, it may be advantageous to apply a cooling gel to the skin prior to irradiation with the apparatus.

In some advantageous embodiments, the apparatus comprises a cooling device such as a pump, recirculator, or cold gas source, and the optical assembly contains a coolant layer. The coolant layer may be an element of the optical assembly, or alternatively it may be external to the optical assembly, for example between the optical assembly and the housing. The coolant layer may be an element in the beam path of the optical assembly, or external to said beam path. The coolant layer actively cools one or more elements of the optical assembly and the tissue being irradiated. The coolant layer is adapted for the flow of a cooling fluid, which may be either a gas or a liquid. The temperature of the fluid may be any temperature, but in advantageous embodiments is maintained approximately at or below the physiological temperature of 37° C. by the cooling device, which is connected to the optical assembly and which circulates fluid in and out of the coolant layer of the optical assembly. The cooling fluid is biocompatible and nontoxic. In advantageous embodiments, the coolant layer is external to the optical assembly. In advantageous embodiments, the cooling fluid comprises water or air. In advantageous embodiments, the optical element of the contact surface of an actively cooling optical assembly is made of quartz, fused silica, glass, sapphire, or other suitable material.

A highly advantageous aspect is that, in some embodiments, the novel low profile design of the optical assembly allows for active tissue cooling without the use of a cooling device such as a fluid pump, recirculator, cold air machine, spray valve, thermoelectric chiller, or other means of active cooling known in the art and that adds complexity, cost, weight, and bulk to the apparatus. In these highly advantageous embodiments, the optical assembly, including the contact surface, is cooled by contact with a detachable heat sink. An aspect of the heat sink is that it is external to the beam path of the optical assembly, for example it may be attached to the top surface of the housing of the optical assembly. As a consequence of the thin, low profile aspect of the optical assembly and the thermal properties of the optical elements, the heat sink efficiently cools the contact element of the optical assembly while remaining advantageously positioned outside the beam path. The heat sink can be cooled prior to attachment to the optical assembly, for example using a small refrigerator or freezer commonly kept in clinics to store medications, and requires no fluid flow or other cooling after attachment to the optical assembly or during irradiation to maintain tissue cooling capability. The concepts disclosed herein allow other cooling devices to be replaced by reusable heat sinks that may be stored at low temperature, attached to the optical assembly at the time of treatment, and returned to storage for later use. Advantageous aspects of embodiments using a detachable heat sink are that the apparatus does not require either a cooling device or consumables, and energy consumption is minimized.

Active cooling with reusable external heat sinks is not feasible with current technology for phototherapy, and at present it is not possible to actively cool tissue being ablated, coagulated, or otherwise thermally modified without the use of cooling devices such as pumps, chillers, and the like, and in some cases with consumables as well.

In some embodiments, the optical assembly comprises one or more heat transfer layers. Said heat transfer layer comprises fluid with thermal conductivity k greater than that of air, and substantial transparency at the wavelength or wavelengths of light emitted by the light source. In some embodiments, the at least one heat transfer layer is disposed between optical components of the optical assembly, such as between two window elements or between a window element and the light guide plate. In other embodiments, a heat transfer layer is disposed between an optical component and a reflecting plate at the proximal boundary of the optical assembly. In other embodiments, the extraction features of the light guide plate are configured to transfer heat from the light guide plate through an air gap to a reflecting plate at the proximal boundary of the optical assembly. In advantageous embodiments, the extraction features of the light guide plate are configured to transfer heat from the light guide plate through an air gap to a reflecting plate at the proximal boundary of the optical assembly, wherein said extraction features are applied material comprising a particulate substance with a thermal conductivity greater than that of air. In other embodiments, the heat transfer layer is disposed between the optical assembly and the housing, or between the reflecting plate and the housing, in which case the heat transfer layer does not need to be transparent, and may be, for example, a flowing nontransparent fluid or a layer of thermal epoxy.

The housing can be made of a substantially rigid moldable or machinable biocompatible material. The interior surface of the housing does not substantially absorb the wavelength or wavelengths of the source connected to the optical fiber, and all or part of the interior surface of the housing can be specularly or diffusely reflective. All or part of the interior surface may be coated with a material that is diffusely reflective of the wavelength or wavelengths of light being transmitted by the optical fiber. In some embodiments, all or part of the interior surface has a coating made of gold or other reflective material. In some embodiments, some or all of the lateral edges of one or more optical components of the optical assembly are polished or coated. The housing material may be Ultem® (GE Plastics), Makrolon® (Bayer), or other polymeric material that is laser-resistant and which has relatively low thermal conductivity. In embodiments where an external heat sink is used, the housing may have a top surface that is made of a material with higher thermal conductivity, for example 316 stainless steel.

For convenience, properties of some exemplary materials that may be used in an apparatus of the invention are listed in the following table:

| material | refractive | thermal conductivity k |
|---|---|---|
| fused silica (Suprasil ®) | 1.46 | 1.4 |
| glass (BK7) | 1.517 | 1.114 |
| polymethylmethacrylate | 1.491 | 0.16-0.24 |
| polycarbonate (Makrolon ®) | 1.586 | 0.19 |
| sapphire | 1.76 | 58 |
| polyetherimide (Ultem ®) | — | 0.122 |
| polyvinyl chloride | 1.500 | 0.2 |
| barium sulfate $BaSO_4$ | 1.64 | 1.31 |
| titanium dioxide $TiO_2$ (rutile) | 2.7 | 10 |
| alumina $Al_2O_3$ | 1.76 | 58 |
| zirconium oxide $ZrO_2$ | 2.2 | 10.5 |
| zinc white ZnO | 2.0 | 30 |
| water | 1.33 | 0.58 |
| Fluorinert ™ FC-43 | 1.291 | 0.065 |
| Fluorinert ™ FC-70 | 1.303 | 0.070 |
| air | 1.00 | 0.0262 |
| stainless steel (316 grade) | — | 16.2 |
| thermal epoxy | — | 1-7 |

Design and optimization of an optical assembly is facilitated by use of optical design software to simulate the propagation of photons through the device, taking into account the optical properties of the elements of the optical assembly including the scattering properties of the extraction features. The initial design may be constrained, for example, by the shape and size of the light-emitting contact surface required for effective irradiation of a particular region of tissue, by the diameter and NA of an optical fiber that can be efficiently coupled to the light source, by the choice of light guide plate material and cooling design, and by the source wavelength required for the phototherapeutic application. Based on such constraints, a preliminary design with a particular optical assembly and initial distribution of extraction features can be made. Then, using optical design software, the number, size, and distribution of extraction features can be adjusted as necessary to optimize output uniformity and transmission efficiency. The software package LightTools (Optical Research Associates, Pasadena, Calif.) was used by the present inventors. Other packages useful for this purpose include TracePro (Lambda Research, Littleton, Mass.) and Specter (Integra, Tokyo, Japan).

The output of radiation from the light-emitting contact surface is substantially Lambertian or nearly Lambertian, that is, with rays randomly oriented and highly divergent. This aspect is a consequence of diffuse reflectance by the extraction features and the interior of the housing and/or lateral edges of components of the optical assembly. With a collimated source, the intensity of light at the tissue surface at a distance is unchanged, whereas for a Lambertian source, the intensity of light decreases as the square of the distance. In embodiments in which tissue is actively cooled, the apparatus provides a means of performing procedures using low or high power laser or light sources for safe, efficacious treatment using an optical assembly that is smaller, lighter, easier to hold, and less fatiguing for the medical or aesthetic operator, eye safe for the patient, operator, and staff, and that is efficient and of low cost to manufacture. Eye protection with lower optical density for better visibility may be used. In embodiments in which the optical assembly passively cools the tissue, or in which the tissue is actively cooled by an optical assembly in thermal contact with a prechilled detachable heat sink, the apparatus provides a means of safe, lower cost treatment using low or high power laser or other light sources, and that is highly advantageous for home use skin treatment products as well as for medical practitioners, staff, and patients.

Embodiments may be highly advantageous for treatment of internal superficial tissues of the body, for example a lumen or hollow organ. In these embodiments, at least one and more advantageously at least two optical assemblies are disposed so that their light-emitting contact surfaces can be brought into contact with the interior surface of the lumen or organ. In advantageous embodiments, at least two optical assemblies are attached to an expanding element, such that the assemblies can be inserted into the organ with the expanding element in a collapsed or unexpanded state, and brought into position adjacent to the superficial tissue requiring treatment. The expanding element is then expanded, to bring the light-emitting contact surfaces into contact with said tissue.

Advantages of embodiments disclosed herein for treatment of internal superficial tissues is that high light intensities, or light intensities at least sufficient to result in ablation, coagulation, denaturation, new collagen generation, cellular injury, cell death, heat shock, or other thermal or thermally-mediated effect, can be achieved with an apparatus delivering substantially uniform irradiation to the tissue surface. In some embodiments, the at least one optical assembly actively cools the tissue surface, for example by fluid flow through the optical assembly from an external cooling device, while the irradiation heats subsurface tissue. In other embodiments, irradiation ablates the surface tissue, with or without concomitant subsurface heating. In addition to the option of surface cooling, the apparatus of the invention uses a light source with wavelength that may be optimized to heat the target tissue of the lumen or hollow organ to a desired depth for appropriate clinical results. In an especially advantageous aspect of an embodiment of the invention comprising a plurality of optical assemblies, the light source of the apparatus is directed in a sequential manner, for example by use of a scanner mechanism, to the optical fibers of each of the optical assemblies, so that the entire luminal area covered by the plurality of light emitting contact surfaces of said assemblies can be treated using a light source of having a fraction of the total power required if the entire luminal area was irradiated at once. However, the disadvantages of other technology are eliminated, since having multiple optical assemblies disposed together in the lumen eliminates the problems associated with moving a light source or emitter from area to area within said lumen. The ability to fit multiple optical assemblies within a lumen or hollow organ is a consequence of the thin low profile design of said assemblies.

A further and highly advantageous aspect of the embodiments disclosed herein is that the light-emitting optical assembly can be protected by a transparent, disposable sleeve during use. In embodiments using a sleeve to protect the optical assemblies, said assemblies may be protected from contamination by body fluids, and reused. The sleeve may be made substantially entirely of polymeric material with substantial transparency to the wavelength of the light source. For example, the sleeve may have 75% transmission, or 90% transmission. More advantageously the sleeve has a transmission over 90%. Or, the sleeve may comprise non-transparent flexible polymeric material and substantially transparent window portions that are adapted to be aligned with and come into contact with the light-emitting contact surfaces of the optical assemblies. The substantially transparent window portions of the sleeve may be flexible transparent plastic, such as but not limited to polyethylene, polyimide, polyurethane, latex, polyolefin, fluorocarbon polymer, or the window areas may be rigid or semi-rigid plastic, such as but not limited to acrylic, polyvinyl chloride, or polycarbonate. In one embodiment, the substantially transparent window portions of the sterile disposable sleeve are made of a rigid or semi-rigid transparent polymeric material such as acrylic or polycarbonate that is not substantially thicker than is required to provide mechanical strength and sterile protection.

The embodiments disclosed herein have the following aspects: (1) thinness of the optical assembly; (2) efficiency of optical assembly transmission (ratio of output power to input power), and (3) uniformity of irradiance at the tissue contact surface. Some advantageous embodiments also have the aspect of (4) active tissue cooling capability; others provides a means of irradiating tissue using high power laser and other light sources. The elements and materials of the optical assembly are selected configured in a novel manner to achieve this combination of advantageous qualities relating to shape, and optical and thermal performance.

First Embodiment

FIGS. 3A and 3B are schematic depictions of a simple first embodiment of the device of the invention.

FIG. 3A shows the circular contact surface (40b) of the optical assembly. The contact surface (40b) is flush with the edge surface (30e) of the device housing (30). An optical fiber (10) is attached at or near its light-emitting distal end to the housing (30) with a connector (10a). The proximal end of the optical fiber is attached to a laser or other light source (not shown).

FIG. 3B is a schematic cross-section depiction of the housing and optical assembly of this embodiment. Inside the housing (30) is a light guide plate (40) with proximal surface (40a), and distal or contact surface (40b). The housing (30) has an opening (30a) for entry of light from the optical fiber (10). The opening (30a) is positioned so that the output of the optical fiber is substantially transmitted to the light guide plate (40) through lateral input surface (40c) of said light guide plate. The housing provides a small space or air gap (70) between its base interior surface (30d) and the proximal surface (40a) of the light guide plate. Extraction features (40e) are applied to all or part of the proximal surface (40a) of the light guide plate, in patterns or distributions that vary spatially over said surface. Light transmitted from the optical fiber through the lateral surface of the light guide plate is internally reflected within the light guide plate, and is scattered by the extraction features on the proximal surface of said light guide plate so that said light is substantially emitted from the distal surface of said light guide plate. The base interior surface (30d) and lateral interior surface (30e) of the housing are coated, covered, or made with a substantially reflective material.

All or part of the lateral surfaces of the light guide plate, with the exception of the lateral input surface (40c) adjacent to the output face of the optical fiber, may be optically polished and coated with gold, or left unpolished and coated with a diffusively reflecting substance such as barium sulfate paint. The lateral input surface (40c) may be polished or unpolished but is not reflective.

The refractive index of the light guide plate (40) is higher than that of air or tissue, which will be in contact with said light guide plate of the first embodiment when in use. Air has a refractive index of 1.0, and soft tissue such as skin has an index of approximately 1.34. Therefore, common transparent optical materials with refractive indices in the approximately 1.4 to 1.8 range, such as BK7 glass (Schott AG, $n_d$=1.517), Supracil® (Hereaus, $n_d$=1.46), polymethylmethacrylate ($n_d$=1.49), quartz (1.5), and sapphire (1.76), may be used for the light guide plate to transmit light by TIR.

The light emitted from the light guide plate distal surface (40b) is substantially Lambertian, that is, with rays randomly directed. The irradiance at said surface is substantially uniform. For clarity, FIG. 4B shows the irradiated area (99) at a distance from the distal surface of the light guide, or contact surface. The irradiated area (99) on a tissue surface in contact with the light guide plate distal surface is substantially the same shape and area as the light guide plate distal surface.

Figure 4A:
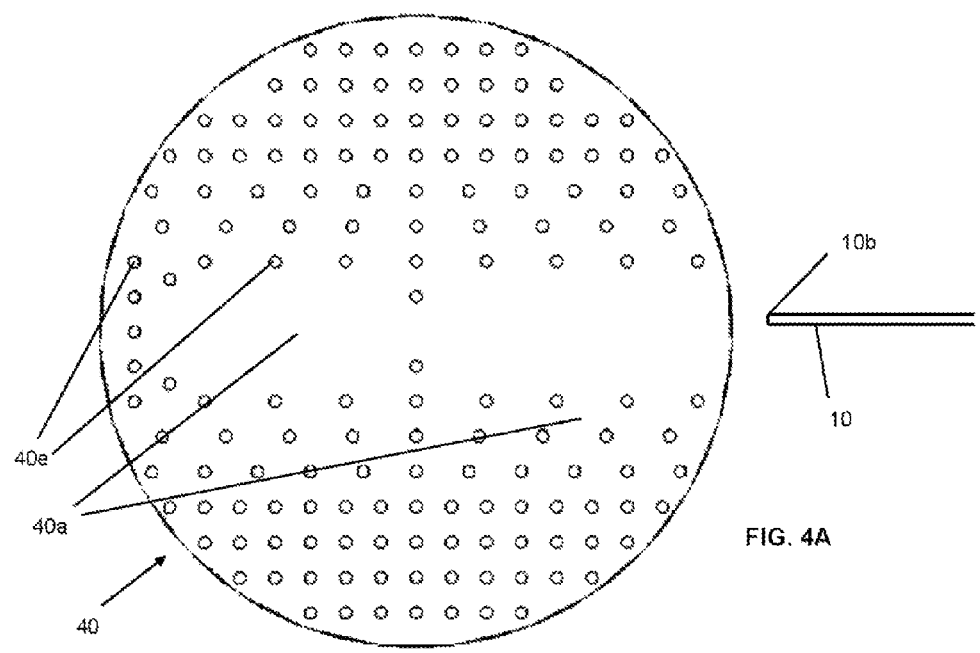
FIGS. 4A and 4B are schematic drawings of a light guide plate.
Figure 4B:
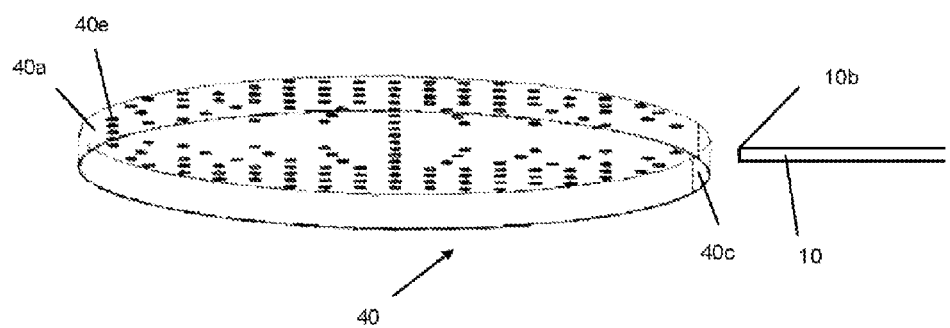

The extraction features (40e) on the proximal surface (40a) of the light guide plate (40) are shown in greater detail in the schematic views of FIGS. 4A and 4B. FIG. 4A shows the proximal surface of the light guide plate. The optical fiber (10) exit face (10b) is in close proximity to the light guide plate lateral input surface. The tilted view of FIG. 4B shows the light input area (40c) on the light guide plate lateral surface.

The extraction features shown in 40e are greatly enlarged and arbitrarily distributed for clarity in FIGS. 4A and B; other patterns and extraction feature sizes are also possible. The pattern and distribution of extraction features corresponding to a device with high uniformity of light distribution and high output efficiency depend on the optical materials and geometry of a optical assembly. The extraction features of the light guide plate in this embodiment are on the proximal surface of said plate. In other embodiments, extraction features may be on both the proximal and distal surfaces of said plate.

The thickness of the air gap (70) is greater than approximately twice the wavelength or wavelengths of light from the light source, or sufficient to allow TIR at the light guide plate proximal surface.

The light guide plate does not need to be substantially thicker than is necessary for flexure strength and resistance to breakage, and for coupling substantially all of the light emitted from the optical fiber of a given NA and distance from the light guide input surface.

This simple first embodiment is an optical assembly that passively cools the tissue surface by conduction of heat by the light guide plate in thermal contact with said tissue surface. Passive cooling capability may be enhanced by using a light guide plate made of a sapphire. Sapphire is an highly advantageous material for the contact element of the invention, due to its very high thermal conductivity of 58 W/m K, high flexure strength of 1200 MPa, resistance to scratching (hardness 1370 kg/mm$^2$), and very high transmission from 190 nm into the infrared. When sapphire is used as the light guide plate, it is found that the strength of this material allows a minimum thickness of approximately 1 mm to be used for light emitting surface area of diameter 7 cm$^2$ or more.

When the light guide plate is fused silica, glass, quartz, or acrylic or other transparent optical plastic, extraction features may be made by a removal or molding process. Molding is a less expensive process in volume, but is limited to features on an approximately millimeter scale. Use of these larger scale features may limit the uniformity of irradiance, depending on the size and shape of the light guide plate. Etching, drilling, or other removal processes can be performed to produce smaller, denser, and more complex extraction features on a submillimeter scale. For example, the features produced by drilling or etching may be in the 50 nm to 700 μm range. More advantageously, the features may be in the 100 to 300 μm range, for example depressions with diameter of about 100 to 300 μm. Sapphire cannot be molded, but can be etched or ablated to produce extraction features. For example, the extraction features can be formed by laser ablation. Additionally, extraction features made by removal processes in sapphire, glass, and other materials can be enhanced by providing a gold or other reflective coating to the features. Gold coating of the features on a light guide plate proximal surface, for example, may be accomplished in practice by applying a coating over the entire proximal surface, and then polishing that surface to remove the coating not located on a feature.

Extraction features may be made by applying diffusive material, for example by printing or direct-write dispensing. Suitable diffusive applied materials include paints or formulations of reflective substances, with a binder to provide mechanical stability, as described previously. Suitable materials include barium sulfate paints commercially available for reflectance coatings, such as Duraflect, Spectraflect, and Labsphere 6080 (Labsphere, North Sutton, N.H.), or formulated according to methods known in the art. Printed extraction features may be used advantageously with commercially available reflective paints or coatings on light guide plates made of fused silica, glass, plastic or quartz. For example, one binder used in commercially available reflectance coating is polyvinyl alcohol (PVA). PVA has a refractive index of approximately 1.52, which matches that of BK7 optical glass, and which is lower than the index of barium sulfate ($n_d$=1.64). Other particulate substances that may be formulated in a diffusive material applied to glass, plastic, quartz, or fused silica include rutile titanium dioxide ($n_d$=2.87), alumina (1.76), zinc selenide (2.71), and zirconium oxide (2.1), zinc sulfide (2.37), zinc oxide (1.95-2.1) and silicon carbide (2.6). These particulate substances can be used with PVA, for example, or other polymeric or inorganic binder known in the art.

When the light guide plate is sapphire and the extraction features are applied material, the most efficient coupling of light out of the light guide plate may be achieved using a binder with higher refractive index than those of the commercially available reflectance coatings. According to example embodiments, this can be accomplished by mixing an organic polymer binder with inorganic nanoparticles of material with high refractive index, or by using the nanoparticles alone as the binder. For example titanium dioxide and zirconium dioxide in nanoparticle form can added to the polymer binder at a concentration giving the combination a refractive index of approximately 1.76, or the refractive index of sapphire. Then, larger titanium or zirconium oxide particles are added to the combination binder to make a material that can be applied to a sapphire light guide for efficient extraction of light. The method for preparing a binder from a combination of polymer and nanoparticles was described previously. Alternatively, the binder can comprise only nanoparticles of alumina, matching the refractive index of sapphire, and combined with yet higher index, larger (about 1 to 3 μm diameter) particles of titanium or zirconium oxide, for example, as the particulate substance for diffuse reflectance.

An optical assembly of this first embodiment with light guide plate made of fused silica, glass, plastic, or quartz will provide passive cooling of tissue, although to a lesser extent than sapphire. All of these materials have thermal conductivity at least an order of magnitude greater than air: quartz has a value of 7.5 W/m K, fused silica 1.4 W/m K, glasses between 0.51 and 1.28 w/m K, and polymethylmethacrylate approximately 0.2 W/m K. Quartz, fused silica and glass are highly transmissive in the visible and near infrared. However, with these substances, the thickness of the light guide should be sufficient to prevent breakage, e.g., approximately 2 mm or more.

Plastics are stronger, but many acrylics, polystyrenes, and polycarbonates have absorption bands beginning at approximately 1100 nm which makes them unsuitable for use with wavelengths of approximately 1100 nm or longer. Plastics typically have lower transmission in the visible and near-infrared wavelengths shorter than approximately 1100 nm than sapphire, quartz, fused silica, or glass, and their use as a light guide plate material will result in relatively poor efficiency for the system. Because of the relatively low thermal conductivity of plastics (0.1 to 0.3 W/m K), a system of the first embodiment with a plastic light guide plate provides relatively inefficient passive cooling. For these reasons of lower transmission efficiency and less effective cooling, and because plastic optical components may be damaged by high power light sources, plastic light guide plates may be less generally advantageous in other implementations.

Advantages of the first embodiment are simplicity for phototherapeutic applications requiring only passive cooling. In some cases, the optical assembly of the first embodiment can be precooled by placing it in contact with ice, cold water, or chilled air prior to use, to enhance tissue cooling.

Second Embodiment

FIGS. 5A and 5B are a schematic depiction of an embodiment of the invention that includes active cooling capability. FIG. 5A shows a circular light-emitting distal surface (60b) of a contact window. The distal surface (60b) is flush with the edge surface (30e) of the device housing (30). An optical fiber (10) is attached at or near its light-emitting distal end to the housing (30) with a connector (10a). The proximal end of the optical fiber is attached to a laser or other light source (not shown). The device also has inlet (20a) and outlet (20b) lines for flow of coolant fluid, connected to the housing (30) with inlet (20c) and outlet (20d) tubing connectors. The other ends of the coolant lines are connected to a cooling device (not shown). The cooling device may be a recirculating chiller with coolant fluid reservoir, or a cold air producing device.

FIG. 5B is a schematic cross-section depiction of the housing and optical assembly of this embodiment. Inside the housing (30) are a light guide plate (40), cooling layer (50), and contact window (60). The light guide plate (40) has a proximal surface (40a) and distal surface (40b). The housing (30) has an opening (30a) for entry of light from the optical fiber (10). The opening (30a) is positioned so that the output of the optical fiber is substantially transmitted to the light guide plate (40) through lateral input surface (40c) of said light guide plate. The openings in the housing for the coolant flow tubes are positioned so that coolant flows into and out of the cooling layer (50). The inlet opening (30b) is depicted. The housing provides a small space or air gap (70) between its base interior surface (30d) and the proximal surface (40a) of the light guide plate. The contact window (60) has a proximal surface (60a) in contact with coolant in the cooling layer (50), and distal contact surface (60b). Extraction features (40e) are applied to all or part of the proximal surface (40a) of the light guide plate, in patterns or distributions that vary spatially over said surface. Light transmitted from the optical fiber through the lateral input surface of the light guide plate is internally reflected within the light guide plate, and is scattered by the extraction features on the proximal surface of said light guide plate so that said light is substantially emitted from the distal surface of said light guide plate. The base interior surface (30d) and lateral interior surface (30e) of the housing is coated, covered, or made with a substantially scattering material.

Coolant flowing into the cooling layer (50) cools the contact window and extracts heat from tissue in contact with said window. Coolant flow also may reduce any heating of other components of the device resulting from internal scattering and absorption of light by optical elements and reflective surfaces including the housing interior surface. In an aspect of this embodiment of the invention, the fluid is substantially non-absorbent of light being transmitted through the optical assembly. In another aspect of this embodiment, the fluid absorbs less than approximately 25% of the light being transmitted through the coolant layer. More advantageous fluid absorbs less than approximately 10% of said light. Most advantageous fluid absorbs approximately 5% or less of said light. Examples of suitable fluids include water, saline, perfluorocarbon such as Fluorinert™ FC-43 or FC-70 (3M, Minneapolis, Minn.), and air, depending on the light source wavelength or wavelengths. For example, at a wavelength region where water has an absorption of greater than 5 or 10% over the cooling layer thickness, a preferred cooling fluid may be FC-43, FC-70 or air. The cooling capability of the optical assembly is determined by the heat transfer properties of the fluid, the temperature of the fluid, and the rate of flow of fluid within the cooling layer.

The light emitted from the contact window distal surface (60b) is substantially Lambertian, that is, with rays randomly directed. The irradiance at said surface is substantially uniform. The irradiated spot (99) on a tissue surface in contact with the contact window distal surface is substantially the same shape and area as the contact window.

Another aspect of this embodiment is that the contact window is made of a rigid material that is substantially transparent to the light of the source connected to the optical fiber. Examples of suitable materials for the contact window include fused silica, quartz, glass, acrylic, and sapphire. More advantageous contact window material has substantially higher thermal conductivity than optical plastics, and is, for example, is quartz, fused silica, glass or sapphire. Most advantageous contact window material has both a high thermal conductivity and high flexure strength, and is sapphire.

An aspect of the second embodiment is that the light guide plate is made of a material that has a higher index of refraction than the cooling fluid. Air has index $n_d$ of 1.0, $n_d$ for water and normal saline is 1.33, and $n_d$ for Fluorinert FC-43 and FC-70 is 1.29 and 1.30, respectively. Therefore, examples of suitable materials include fused silica, quartz, acrylic, and sapphire. An advantageous light guide plate has a thickness that is sufficient for coupling substantially all of the light emitted from an optical fiber of given NA and distance from the light guide input surface, and is not substantially thicker than is necessary for flexure strength and resistance to breakage. If the contact window is sapphire, a light guide plate made of quartz, fused silica, or glass may be protected from damage by said window and the thickness of said light guide plate may be reduced, compared to the first embodiment in which the light guide plate is exposed.

A sapphire light guide plate of the second embodiment has extraction features, as described previously. Also as in the first embodiment, the thickness of the air gap (70) is greater than approximately twice the wavelength or wavelengths of light from the light source, or sufficient to allow TIR at the light guide plate proximal surface.

In this embodiment, the thickness of the light guide plate and optical assembly are minimized. The light guide plate thickness is determined by coupling efficiency with the light source, and the contact window by strength requirements. The cooling layer may be approximately 1 mm in thickness, for cooling with water, perfluorocarbon, or air.

Third Embodiment

Figure 6:
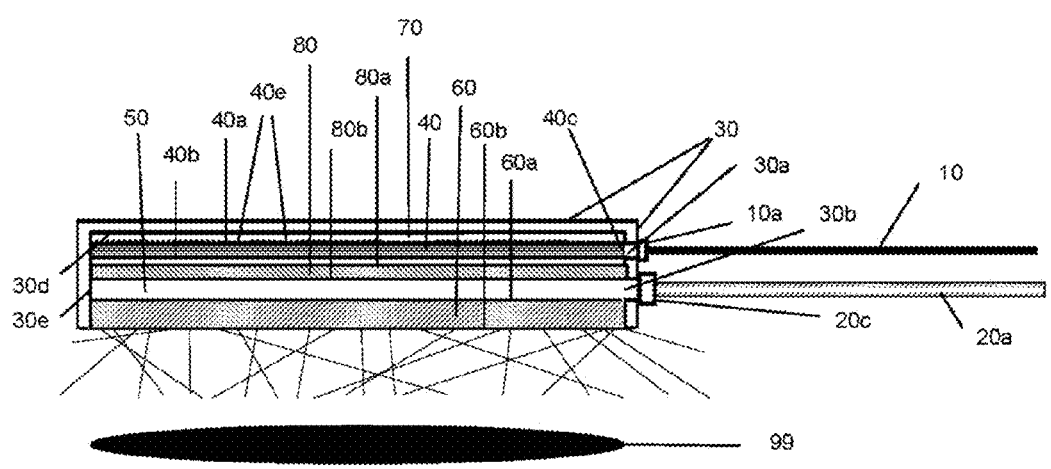
FIG. 6 is a schematic drawing of a third optical assembly.

FIG. 6 is a schematic cross-section depiction of the housing and optical assembly of a third embodiment of the invention. As in the second embodiment, the third embodiment has active cooling capability, however the optical assembly has a minimal air gap between the light guide plate and a cooling layer window, to reduce scattering within the optical and thereby improve efficiency, compared to an optical assembly of the second embodiment.

Inside the housing (30) are a light guide plate (40), a cooling layer window (80), a cooling layer (50), and a contact window (60). The light guide plate (40) has a proximal surface (40a) and distal surface (40b). The housing (30) has an opening (30a) for entry of light from the optical fiber (10). The opening (30a) is positioned so that the output of the optical fiber is substantially transmitted to the light guide plate (40) through an input area (40c) on the lateral surface of said light guide plate. The openings of the housing for the coolant flow tubes are positioned so that coolant flows into and out of the cooling layer (50). The inlet opening (30b) is depicted. The housing provides a small space or air gap (70) between its base interior surface (30d) and the proximal surface (40a) of the light guide plate. The cooling layer window (80) has a distal surface (80b) in contact with cooling fluid in the cooling layer (50), and a proximal surface (80a) in contact with air. The cooling layer window proximal surface (80a) is separated from the light guide plate distal surface (40b) by a space or air gap (85) of at least 2 microns thickness, or at least twice the wavelength or wavelengths of the light source. The contact window (60) has a proximal surface (60a) in contact with coolant in the cooling layer (50) and distal contact surface (60b). Extraction features (40e) are formed by application or removal of material, or molding, to all or part of the proximal surface (40a) of the light guide plate, as described previously.

Light transmitted from the optical fiber through the lateral input surface of the light guide plate is propagated by TIR within the light guide plate in a direction that is substantially parallel to the light guide plate proximal (40a) and distal surfaces (40b). TIR is partially disrupted by the extraction features (40e) on the proximal surface of said light guide plate, such that light is scattered and emitted from the distal surface (40b) of said light guide plate. Said emitted light is propagated through the air gap (85), coolant layer window (80), cooling layer (50), and contact window (60), to irradiate an area (99) on the tissue surface in contact with the contact window.

The base interior surface (30d) and lateral interior surfaces (30e) of the housing is partially or completely coated, covered, or made with a substantially reflective material. All or part of the lateral surfaces of the coolant window and contact window may be coated or covered with a diffusively or specularly reflective material. All or part of the light guide plate lateral surfaces, with the exception of the lateral input surface, may be coated or covered with a diffusively or specularly reflective material.

In an aspect of this embodiment, the fluid is substantially transparent to light being transmitted through the cooling layer. In another aspect of this embodiment, the fluid absorbs less than approximately 20% of the light being transmitted through the cooling layer. An advantageous fluid absorbs less than approximately 10%, and most advantageously absorbs approximately 5% or less of said light. Examples of suitable fluids include water, saline, perfluorocarbons such as FC-43 or FC-70, and air or nitrogen gas, depending on the wavelength or wavelengths of the light source.

An aspect of the third embodiment is that the light guide plate is made of a material that has a higher index of refraction than air. Examples of suitable materials include fused silica, quartz, acrylic, and sapphire. An advantageous light guide plate has a thickness that is sufficient for coupling substantially all of the light emitted from an optical fiber of given NA and distance from the light guide input surface, and is not substantially thicker than is necessary for flexure strength and resistance to breakage. A light guide plate made of quartz, fused silica, or glass may be protected from damage by the contact and cooling window and the thickness of said light guide plate may be reduced. The contact and cooling windows may be fused silica, quartz, acrylic, sapphire, and the like, with thinness limited only by flexural strength.

The light emitted from the contact window distal surface (60b) is substantially Lambertian, that is, with rays randomly directed. The irradiance at said surface is substantially uniform. The irradiated area (99) on a tissue surface in contact with the contact window distal surface is substantially the same shape and area as the contact surface.

In an aspect of this embodiment, the pattern or distribution of extraction features on the light guide plate is selected to produce a substantially uniform irradiance at the distal surface of the contact window. In another aspect of this embodiment, the pattern or distribution of extraction features is selected to produce high transmission efficiency and a substantially uniform irradiance at the distal surface of the contact window. An advantageous transmission efficiency is 50% or higher. A more advantageous transmission efficiency is 80% or higher. An advantageous irradiance at the distal surface of the contact window has uniformity of approximately +25% to −25% or better. A more said irradiance has uniformity of approximately +10% to −10% or better.

Fourth Embodiment

In a fourth embodiment, the cooling layer may be disposed between the proximal surface of the light guide plate and the interior surface of the housing. An advantage of this embodiment is that the light guide plate is also the contact window, so that the thickness of the optical assembly is reduced while providing active cooling. Reducing the thickness of the optical assembly reduces internal scattering and increases transmission efficiency, as well as making the device advantageously thin.

Figure 7:
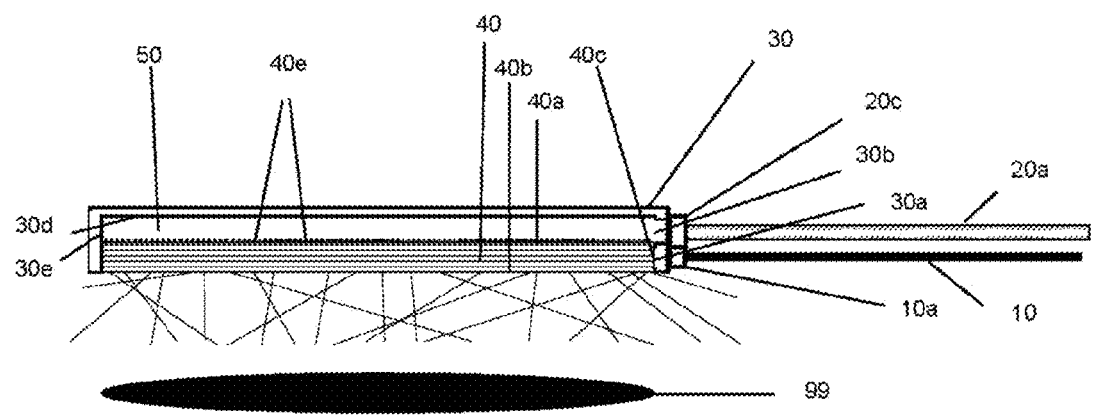
FIG. 7 is a schematic drawing of a fourth optical assembly.

FIG. 7 is a schematic cross-sectional depiction of the housing and optical assembly of this embodiment. Inside the housing (30) is a light guide plate (40) and a cooling layer (50). The light guide plate (40) has a proximal surface (40a) and distal surface (40b). The housing (30) has an opening (30a) for entry of light from the optical fiber (10). The opening (30a) is positioned so that the output of the optical fiber is substantially transmitted to the light guide plate (40) through lateral input surface (40c) of said light guide plate. The openings of the housing for the coolant flow tubes are positioned so that coolant flows into the cooling chamber (50). The inlet opening (30b) is depicted.

Extraction features (40e) are applied to all or part of the proximal surface (40a) of the light guide plate, in patterns or distributions that vary spatially over said surface. Light transmitted from the optical fiber through the lateral surface of the light guide plate is propagated transversely by TIR within the light guide plate, and is scattered by the extraction features on the proximal surface of said light guide plate so that said light is substantially emitted from the distal or contact surface (40b) of said light guide plate. The base interior surface (30d) and lateral interior surface (30e) of the housing is coated, covered, or made with a substantially reflecting material. The irradiated spot (99) on a tissue surface in contact with the contact window distal surface is substantially the same shape and area as the contact window.

In an aspect of this third embodiment, the coolant fluid is substantially transparent to light being transmitted through the coolant chamber. The fluid may be a liquid or a gas. In another aspect of this embodiment, the fluid absorbs less than approximately 20% of the light being transmitted through the optical assembly. An advantageous fluid absorbs less than approximately 10% of said light. A highly advantageous fluid absorbs approximately 5% or less of said light. Examples of suitable fluids include water, saline, perfluorocarbons FC-43 or FC-70, air, or nitrogen gas, depending on the wavelength of the light source.

An aspect of the present embodiment is that the light guide plate is made of a material that has a higher index of refraction than the tissue or the fluid of the coolant layer. Examples of suitable materials include fused silica, quartz, PMMA, and sapphire. An advantageous light guide plate has a thickness that is sufficient for coupling substantially all of the light emitted from the optical fiber, and is not substantially thicker than is necessary coupling or for strength. An advantageous light guide plate material has a moderate to high thermal conductivity, of about 1 W/mK or higher. The extraction features of the light guide plate may be a diffusing material applied in the form of an adherent paint or coating with binder and particulate substance of appropriate refractive index, as described previously, and that will not be degraded or eroded by contact with the coolant fluid. For example, when the light guide plate is made of quartz, the applied material may be barium sulfate applied in the form of Duraflect coating material (Labsphere, North Sutton, N.H.), and the cooling fluid may be, for example, water, saline, perfluorocarbon, air, or nitrogen gas, depending on source wavelength. The applied material may be in a form that is not resistant to flowing liquid, for example barium sulfate pain applied in the form of Labsphere 6080 coating material (Labsphere, North Sutton, N.H.), in which case the cooling fluid is air or nitrogen gas.

According to example embodiments, when the light guide plate is made of sapphire, a high index binder comprising organic polymer and inorganic nanoparticles, and particulate substance such as zirconium or titanium oxide may be used when the cooling fluid is air or nitrogen, as described previously. Another preferred light guide plate material is sapphire, quartz, fused silica, or glass with extraction features formed by removal of material (etching, milling, machining, and/or ablating). If extraction features are formed by removal or molding, the light guide plate can be exposed to flowing liquid or gas in the cooling layer without erosion. The light guide plate is of sufficient thickness to provide adequate resistance to breakage. The present embodiment requires cooling fluid substantially free of particulate impurities and in advantageous configurations has a filtration system to minimize contamination of the extracting features of the light guide plate.

In another aspect of this embodiment, the pattern or distribution of extraction features is selected to produce high transmission efficiency and a substantially uniform irradiance at the distal surface (40b) of the light guide plate.

Fifth Embodiment

In a fifth embodiment, a reflecting plate is disposed between the cooling layer and the proximal surface of the light guide plate. An advantage of this reflective plate is that extraction features on the light guide plate proximal surface are protected from erosion or dissolution by, or contamination or reaction with, the flowing coolant of the cooling layer. A further advantage of the reflective plate is that the cooling layer is not part of the optical assembly and is not exposed to light. The coolant fluid is therefore not limited to gases or liquids that are substantially transparent light of the wavelength or wavelengths emitted from the optical fiber. Consequently, water, an advantageous coolant fluid because its good heat transfer capability, low cost, and biocompatibility, can be used in this embodiment even at source wavelengths where there is substantial absorption by water.

Figure 8:
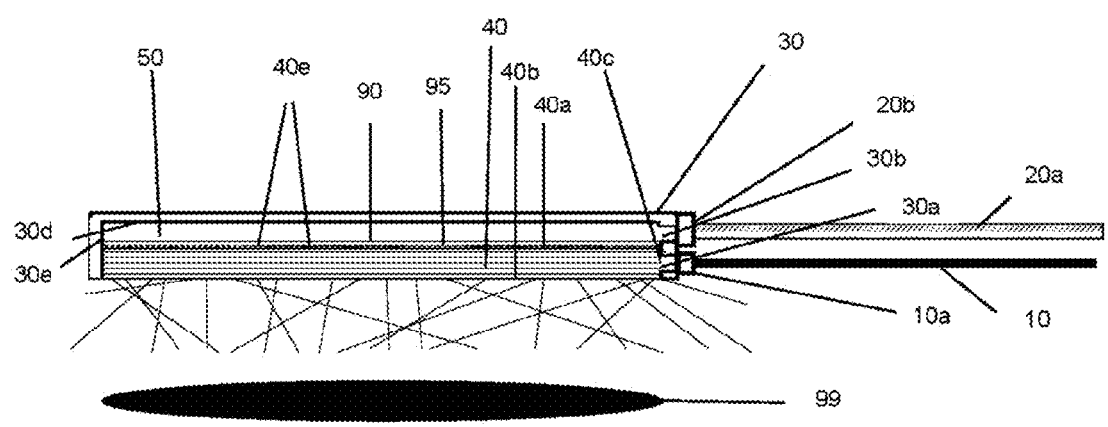
FIG. 8 is a schematic drawing of a fifth optical assembly.

FIG. 8 is a schematic cross-sectional depiction of the housing and optical assembly of the fifth embodiment. Inside the housing (30) is a light guide plate (40) and a cooling chamber (50). The light guide plate (40) has a proximal surface (40a) and distal surface (40b). A thin reflective plate (90) is disposed adjacent to but not in contact with the proximal surface (40a) of the light guide plate. An extraction space (95) is provided between the light guide plate (40) and the reflective plate (90). The extraction space (95) is at least 2 µm in thickness, or at least twice the wavelength of the light source. The housing (30) has an opening (30a) for entry of light from the optical fiber (10). The opening (30a) is positioned so that the output of the optical fiber is substantially transmitted to the light guide plate (40) through lateral input surface (40c) of said light guide plate. The openings of the housing for the coolant flow tubes are positioned so that coolant flows into the cooling layer (50). The inlet opening (30b) is depicted. Extraction features (40e) are applied to all or part of the proximal surface (40a) of the light guide plate, in patterns or distributions that vary spatially over said surface. Said light transmitted from the optical fiber through the lateral surface of the light guide plate is propagated transversely by TIR within the light guide plate, and is scattered by the extraction features (40e) on the proximal surface of said light guide plate so that said light is substantially emitted from the distal or contact surface (40b) of said light guide plate. The base interior surface (30d) and lateral interior surface (30e) of the housing is coated, covered, or made with a substantially non-absorbent material. The irradiated spot (99) on a tissue surface in contact with the contact window distal surface is substantially the same shape and area as the contact window.

In another aspect of the fifth embodiment, the extraction space (95) may contain a substantially static amount of air, gas, or liquid that is substantially transparent to the light transmitted by the optical fiber, and with refractive index lower than the light guide plate. Preferably, the extraction space contains a liquid with high thermal conductivity. Preferably, the liquid of the extraction space comprises perfluorocarbon (Fluorinert™, 3M, Minneapolis Minn.). The perfluorocarbon preferably has a boiling point well above room temperature and relatively low vapor pressure, such as Fluorinert™ FC-43 or FC-70, among others. Fluorinert™ fluids typically increase in volume by 1% for every 10° C. temperature increase. An aspect of this embodiment is that the thin reflective plate (90) is metallic and sufficiently thin to provide for change in volume with temperature of the fluid in the extraction space (95). Circulation in the cooling layer of a fluid maintained at 2° C., for example, reduces the temperature of a static fluid in the extraction space (95) originally at room temperature by approximately 20° C. The flexibility of a thin metal reflective plate can adequately adapt to an approximately 2% change in liquid volume without distortion and possible bubble formation within the extraction space. The reflective plate may be a metal with moderate to high thermal conductivity, and may be polished or coated with a diffusively reflective material on all or part of its surface in contact with the extraction layer.

An aspect of the present embodiment is that the light guide plate is made of a material that has a higher index of refraction than the material within the extraction space (95). Examples of suitable materials include fused silica, quartz, acrylic, and sapphire. When the difference between refractive indices of fluid of the extraction space and the light guide plate is relatively small, for example if the fluid is Fluorinert and the light guide plate is etched quartz, fused silica or glass, etched features of sufficient depth to effectively scatter and extract light from the light guide plate are advantageous.

In an aspect of this fifth embodiment, the pattern or distribution of extraction features is selected to produce a substantially uniform irradiance at the distal surface of the light guide plate. In another aspect of this embodiment, the pattern or distribution of extraction features is selected to produce high transmission efficiency and a substantially uniform irradiance at the distal surface of the light guide plate.

The present embodiment has many advantages; it contains only one optical component in the optical assembly for minimal thickness, ease of manufacture, and low cost; it has a cooling layer outside the optical assembly to eliminate light absorption by cooling fluid and allow use of water as coolant; and can be configured with components having high thermal conductivity for excellent cooling capability.

Sixth Embodiment

In the sixth embodiment, the reflective plate (90) is in thermal contact with extraction features formed by application of diffusive applied material to the light guide plate proximal surface. The extraction features are in thermal contact with the reflective plate, providing an efficient route for heat transfer from the light guide plate to the cooling layer without the need for liquid in the extraction space. Air or nitrogen in the extraction space will have a lower refractive index than a liquid, such that TIR is more efficient and the optical assembly transmission efficiency may be even greater than in the previous embodiment. The reflective plate (90) may be made of metal, more advantageously a thermally conductive metal, and may be advantageously polished or having a diffusive reflective coating on the side in contact with the extraction features. An advantageous reflective plate has a diffusive reflective coating on the side in contact with the extraction features, for good thermal contact.

Figure 9A:
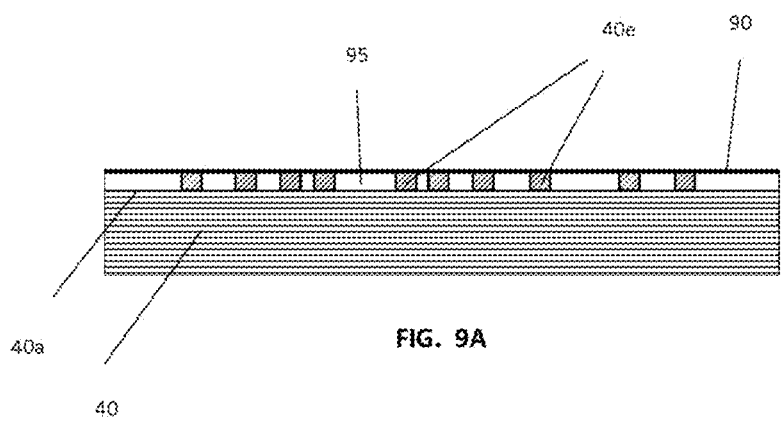
FIGS. 9A and 9B are schematic drawings of a light guide plate, extraction features, and reflective plate of a sixth optical assembly.
Figure 9B:
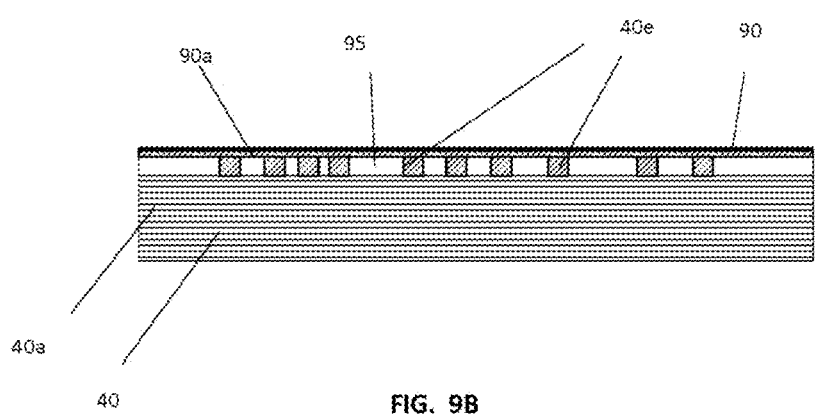

FIGS. 9A and B are schematic depictions of this embodiment. In FIG. 9A the extraction features (40e) of the proximal surface (40a) of a light guide plate (40) are in contact with the reflective plate. In FIG. 9B the extraction features (40e) are in contact with a coating (90a) of the reflective plate (90).

According to the sixth embodiment, the extraction features disrupt TIR in the light guide plate and transfer heat from the light guide plate through the reflective plate to the coolant layer. Extraction features formed of applied material, such as reflectance paint applied by printing, may have thickness on the order of tens to hundreds of microns, which is more than sufficient to provide an air gap between light guide proximal surface (40a) and reflective plate of at least 2 μm when the reflective plate is in contact with the top surface of the dots.

An important aspect of this embodiment are the thermal characteristics of the extraction features. Formulations used for creation of extraction features of the applied material type are typically composed of a particulate substance and binder, as described previously. The particulate substance is the larger component. In this embodiment, an advantageous particulate substance has a thermal conductivity substantially greater than that of the surrounding air in the extraction space (0.024 W/mK), in addition to being highly reflective. An advantageous substance has thermal conductivity greater than 1 W/mK. Examples of suitable substances include barium sulfate (18.4 W/mK, zirconium dioxide (10.5 W/mK), and titanium dioxide (11 W/mK), depending on the light guide plate material.

An advantageous optical assembly of this embodiment may have, for example, a sapphire light guide plate and an applied material comprising PVA and zirconium oxide nanoparticles, and zirconium dioxide scattering particles.

Seventh Embodiment

In this embodiment, the optical assembly is adapted to emit light in a more directed manner. An advantage of this embodiment that may be useful in certain applications is that light that is more collimated or directed will have a greater depth of penetration in tissue.

Figure 10:
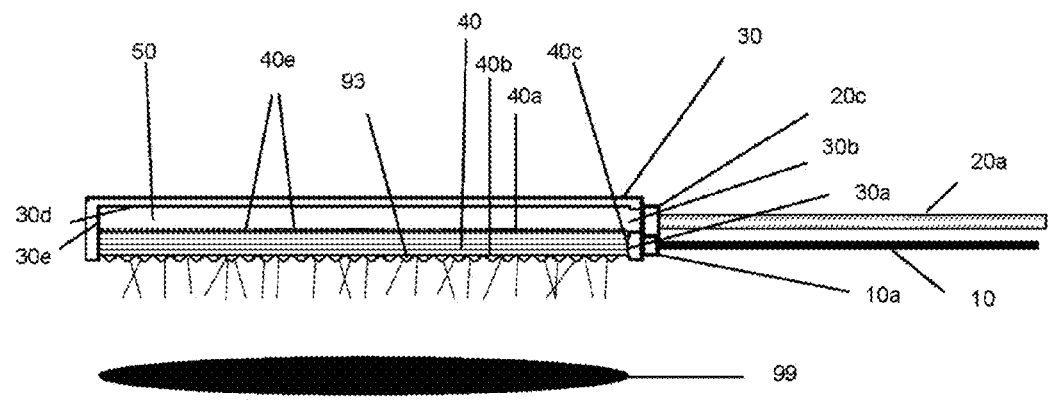
FIG. 10 is a schematic drawing of a seventh optical assembly.

FIG. 10 is a schematic depiction of the seventh embodiment, which is similar to the assembly shown in FIG. 7, and for brevity the features of this embodiment that are the same as the fifth embodiment are given the same numbers and their description is not repeated here. New aspects of this embodiment include collimating features (93) shown in FIG. 10. The collimating features may be a series of ridges, grooves, lenslet arrays, and the like.

Eighth Embodiment

In an embodiment, irradiation is delivered in a fractional manner to the tissue. Fractional treatment is useful in some applications to allow zones of untreated tissue to be interspersed among treatment sites, for improved healing for example.

Figure 11A:
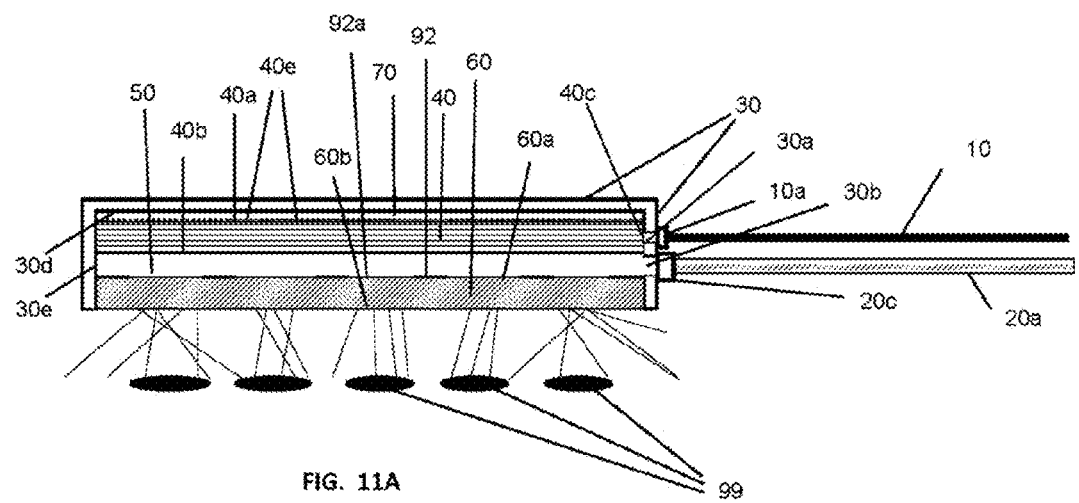
FIGS. 11A and B are schematic drawings of an eighth optical assembly.
Figure 11B:
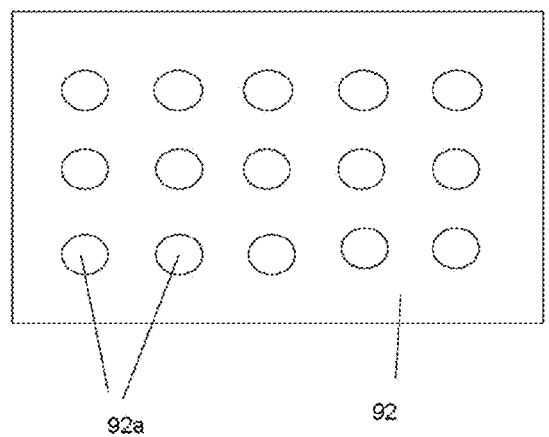

FIGS. 11A and 11B depict this eight embodiment. FIG. 11A is similar to FIG. 5B, and includes a mask (92) disposed at the proximal surface of the contact window. The mask (92) has holes or openings (92a) through which light may pass in the optical assembly. The irradiates sites on the tissue surface (99) are then of a size, shape and position similar to the mask openings (92a).

The mask may be a thin metal reflective component, or it may be a reflective coating on an optical surface, for example the contact window. A mask in the form of a gold coating on an optical surface is advantageous. It will be appreciated that based on the design of the optical assembly, which has different configurations in the previous seven embodiments, a mask may be inserted at various points within the optical assembly, including on or adjacent to the distal surface of the light guide plate, on or adjacent to either surface of a contact window, or on or adjacent to either surface of a cooling layer window. The openings (92a) of the mask may be of any size, shape, arrangement, or density that is useful for a phototherapeutic application.

Figure 12A:
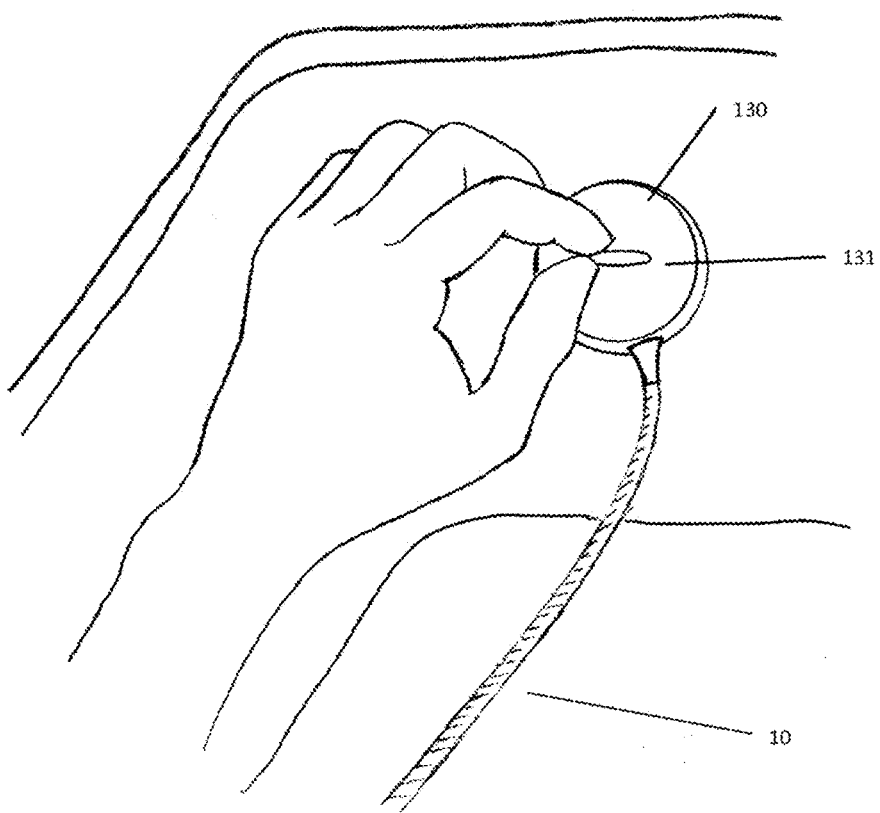
FIG. 12A is a drawing of an optical assembly and transmission element in use to treat the skin surface.

FIG. 12A is a schematic drawing of an optical assembly of embodiments 1-8, as shown here treating the surface of the skin. The optical assembly housing (130) with attached light guide (10) may have a small handle (131).

FIG. 12B is a schematic drawing of a very simple apparatus. The optical assembly (130) is attached to a light source unit (140) by a cable (155). It may be advantageous to support the cable with a pole (154). The cable contains a light guide or optical fiber (151) and cooling input and output lines (152). The light source unit may contain a cooling device (not shown) and may have a user display (150) for setting treatment parameters. A footswitch (157) attached to the unit with a cable (153) may be used to activate the light source.

As described previously, the optical assemblies disclosed herein may be divided into two classes: (1) optical assemblies that contain a substantially rigid light guide plate with diffusing extraction features, and (2) optical assemblies that contain a plurality of reflecting elements. Embodiments using the reflecting type optical assembly are described below. The reflecting device may be one or more prisms or mirrors.

In one embodiment, the apparatus includes a plurality of reflecting elements, where each reflecting element corresponds to a segment area of light distributed at the light-emitting contact surface of the optical assembly. In another embodiment, each reflecting element corresponds to a plurality of segment areas of light distributed at the light-emitting contact surface. These corresponding segment areas of are further described below. In certain embodiments, the apparatus includes a cooling device configured to provide coolant fluid to the optical assembly to remove heat from the light emitting contact surface of an optical assembly. In one embodiment, the coolant is brought in direct contact with the plurality of reflecting devices. In a further embodiment, the apparatus includes at least one channel for cooling fluid flow in direct contact with the reflecting elements.

Ninth Embodiment

In the ninth embodiment, the optical assembly comprises a plurality of prisms.

FIG. 13A is a semi-schematic drawing of an optical design comprising a window element 315 and an optical fiber 309. Optical elements transmit and distribute light from the optical fiber to the window element. Surface 311 is the light-emitting contact surface. In FIG. 13A, the window 315 is square with edge length of approximately 10 mm. Light from the distal end of an optical fiber is transmitted to a 2:1 anamorphic beamshaper 316 and two collimating lenses 317a and 317b, to a first 340 and second 339 prism disposed on the proximal surface of the contact window 315. Prism surfaces 340b and 339b are coated to provide 50% and 100% reflection, respectively. The beamshaper and collimating lenses are selected so that light from the optical fiber substantially fills the proximal face 340a of the first prism. The prisms have a height O of approximately 5 mm, and the window a thickness W of 1 mm. At the light-emitting contact surface 311, the light is distributed over an approximately square total area 399 with edge length D approximately 10 mm. Light passing through prism 340 is transmitted in segment area 399a and light passing through prism 339 is transmitted in segment area 399b. The distance L from the second collimating lens 317a to the proximal face 340a of the first prism 340 is approximately 20 mm.

In FIG. 13B, the effect of increasing the number of prisms from two to three is shown. Prism surfaces 340b, 339b, and 338b are coated to provide 33%, 50%, and 100% reflection, respectively. Again, the distance from the second collimating lens to the proximal face 340a of the first prism 340 is approximately 20 mm. The light is distributed over an approximately square total area 399 with edge length (D) approximately 10 mm, at the light-emitting contact surface 311, as in FIG. 13A. Light passing through prisms 340, 339, and 338 are transmitted in segment area 399a, 399b, and 399c, respectively. However, the prism height O is reduced to approximately 3.5 mm, allowing for a significantly thinner optical assembly. With a 1 mm sapphire window, and a 1 mm thick housing, the total thickness is 5.5 mm.

The distance L in FIGS. 13A and 13B is greater than the dimension D of the irradiated area on the contact surface 311. In practice, this will require a straight, rigid section of the handpiece between the fiber exit face and the first prism of over 2 cm. This distance L may be advantageously reduced by adding another collimating lens, as in FIG. 13C. With three lenses 317a, 317b, and 317c, L is reduced to approximately 10 mm. Also in FIG. 20C, the number of prisms is increased to four, with surfaces 340b, 339b, 338b, and 337b having reflectivity of 25%, 33%, 50%, and 100%, respectively. Here, the prism height O is reduced to approximately 2.5 mm, while D is maintained at approximately 10 mm. With a 1 mm sapphire window, and a 1 mm thick housing, the total thickness is 4.5 mm.

Cooling capability may be added to a device of FIGS. 13A-13C by adding a second window to create a space through which cooling fluid may be introduced, as shown in FIG. 13D. Window 314 is parallel to window 315, such that a coolant layer 345 is formed. Cooling fluid inlet 310a and outlet 310b lines are connected at their proximal ends to a cooling device such as a recirculating chiller (not shown) and at their distal ends with a connector (not shown) at openings in the housing 312 to coolant layer 345. A housing 312 contains prisms 340, 339, 338, and 337, windows 314 and 315, collimating lenses 317a-c, and anamorphic lens 316. Windows 315, the coolant layer 345, and the housing 312 are each about 1 mm thick. Window 315, in a protected position behind window 314, may be thinner than window 314. With windows made of sapphire, the total window thickness may be about 1.5 mm. The prisms may be made of quartz, fused silica, glass, or any other transparent optical material. The total thickness H of the housing and optical components is only 6 mm.

Tenth Embodiment

Still further reductions in total thickness can be achieved by increasing the number of reflecting surfaces, as shown in FIGS. 14A-14C. Reflecting surfaces can be, for example, surfaces of either solid optical elements such as prisms, or they can be surfaces of mirrors. In this embodiment, the elongated prisms are replaced by elongated mirrors, and light is delivered to the mirror surfaces using individual fibers from a fiber bundle. As used herein, the term elongated is used to describe reflecting devices that have a length sufficient to span across much of the length of the optical assembly. To produce an irradiated square area with edge length 10 mm, five elongated mirrors 441, 442, 443, 444, and 445 are disposed on a contact window 415.

A total of twenty five individual fibers 409a-y are positioned to irradiate twenty five circular areas 498a-y on the angled reflecting surfaces of the mirrors. The proximal ends of the fibers 409a-y are combined in a fiber bundle attached to a light source (not shown). The distal ends 419a-y of fibers 409a-y are disposed in channels within the housing 412, so that light from each fiber is directed towards the elongated mirrors, to form an array of circular irradiated segment areas 498a-y on the mirrors. Reflection from the mirrors then creates an array 499 with D of 10 mm, from the individual segment areas 499a-y on the light transmitting contact surface 411. In FIGS. 14A and 14B, the fiber distal ends 419a-y are shown as small cylinders, for clarity, whereas in actuality the distal ends may be a simple cleaved or polished surface of the fiber. The size of areas 499a-y may be varied by changing the distance between fiber distal ends 419a-y and the mirrors, for example.

Figure 15A:
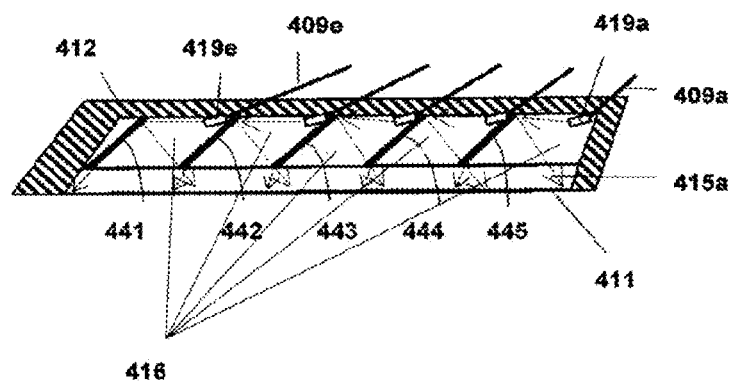
FIGS. 15A and 15B show the tenth assembly with cooling channels.
Figure 15B:
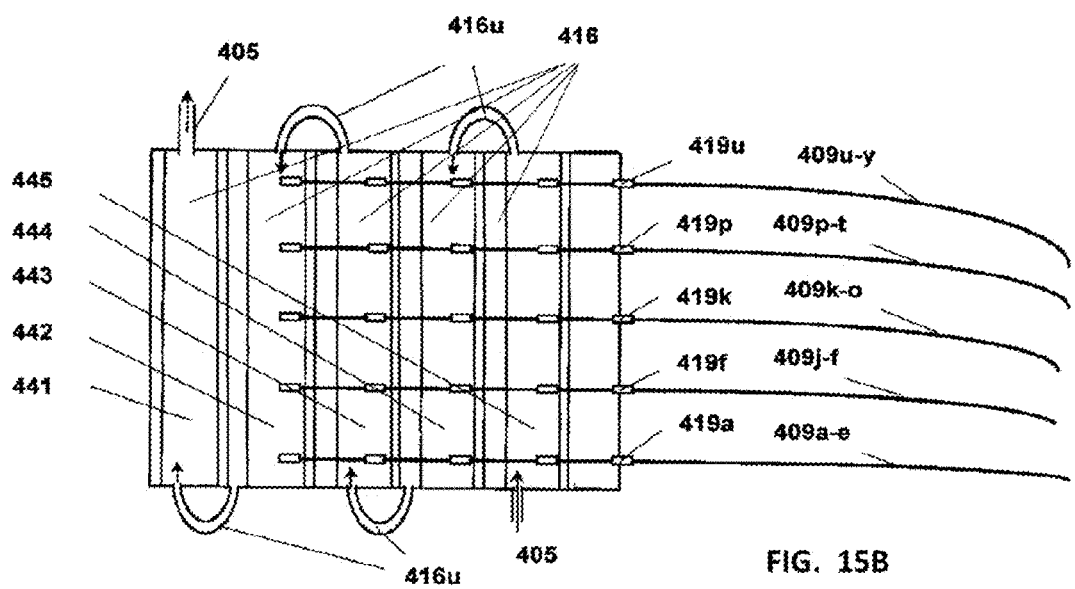

Cooling ability can be added to the device of FIG. 14 by adding a second window in parallel to the first, to provide a cooling layer in between, as in the device of FIG. 13D. However, it is recognized here that the space adjacent to or surrounding the mirrors may be used to cool the optical assembly, with an advantageous reduction in total thickness of the handpiece. The concept is shown schematically in FIGS. 15A and 15B, for the same optical layout as in FIGS. 14A-14C. For brevity, elements with the same numbers are not described again.

Space between the rows of elongated mirrors provides channels 416 for fluid flow. By adding coolant flow redirecting channels 416u at the edge of the optical assembly, a single continuous channel for coolant between inlet 410a and outlet 410b coolant lines can be obtained, that routes fluid evenly over the window and minimizes turbulence or the possibility of air pockets if the fluid is a liquid. A fluid suitable for use in this embodiment is any liquid or gas that is substantially transparent to the wavelength or wavelengths of the light source, and which is nontoxic and biocompatible. Depending on the light source, advantageous choices include cold air, water, and saline. Another advantageous choice is a perfluorocarbon such as Fluorinert™ (3M, Minneapolis, Minn.). Suitable Fluorinerts™ include FC-70 and FC-43, among others. The total thickness of a device as shown in FIG. 15, including housing, is about 4.5 mm, which is very advantageously thin.

Eleventh Embodiment

FIGS. 16A-16C is a semi-schematic depiction of another embodiment. As shown in FIGS. 16A and 16B, light is reflected by mirrors, however in this embodiment there is a separate mirror for each individual fiber from a fiber bundle. In this embodiment the mirrors are not considered elongated. Rather, several short mirrors are arranged side by side to span across the length of the optical assembly, as shown in FIG. 16B. The window 515 is a square with edge length 12.5 mm and rounded corners. There are nineteen mirrors 545a-s and nineteen individual fibers 509a-s, arranged to produce circular irradiated segment areas 599a-s of diameter about 2.5 mm each. The irradiated areas on surface form a hexagonally shaped area of substantially uniform irradiation, with dimension D approximately 12.5 mm. Distal ends of fibers 509a-s are disposed within the spaces between the mirrors, to further reduce total thickness to a very thin 3.5 to 4.0 mm. For active cooling capability without increased thickness, coolant fluid may be circulated within the housing, either around the individual mirrors, or in channels produced by setting the mirrors in partitions made of Ultem or other laser-resistant material to guide fluid flow, with insertion holes in said partitions for the distal ends of fibers 509a-s to be placed between mirrors.

As may be appreciated, the irradiation pattern and array size and shape at the contact surface can be readily changed by repositioning the mirrors, and by increasing or decreasing the number of mirrors. An advantage of the reflective optics design is flexibility in producing handpieces with a wide range of contact surface areas and shapes, using a limited number of standardized optical components, for example the mirrors, fibers, and a window. The housing of the embodiments shown in FIGS. 13-16 may be any biocompatible material known in the art that can be molded or machined, including metals or plastics. The interior of the housing may be coated for reflectivity, or may be uncoated. An advantageous material for the housing includes Ultem, or other such laser-resistant plastic material.

In order to an achieve advantageously thin assembly of optical components within the housing attached to the handpiece distal ends, it is found that a plurality of reflecting devices, for example either prisms or mirrors, may be used. As found using the reflective optics design described herein, the thickness of the housing containing the optical elements may be as small as about 3.5 mm. Irradiated areas of light-emitting surfaces may be increased to any size, without an increase in thickness, by increasing the number of reflecting devices. A reflective optics design also has the important advantage of high transmission efficiency from light source to light-emitting contact surface. For the design of FIGS. 16A-16C with antireflection coatings, losses including Fresnel reflections, absorption of the mirror, and a 9% loss associated with the fiber bundle, yield a total transmission of 86.5% with air cooling. With proper choice of cooling fluid, for example the highly transparent perfluorocarbons, a liquid cooled design may have similar high transmission.

In a reflective optics design of the optical assembly, light is transmitted in segments from the light source to the light-transmitting contact surface. The total light at the contact surface is in the form of an array or combination of individual segment areas, each segment area corresponding to a reflecting surface or an area on a reflecting surface. For example, in FIGS. 14B and 14C the twenty-five segment areas 499a-y correspond to reflecting areas 498a-y on the mirrors, and in FIG. 13A, the two segment areas 399a and 399b correspond to reflections on prisms 340 and 339.

As described previously, uniformity of irradiance at the light transmitting contact surface of the apparatus is desired. For an apparatus using reflective optics as described herein, uniformity is influenced by several factors, including the placement or pattern of individual segment areas within the contact surface area, the number of individual segment areas, the uniformity of light within each segment area, the amount of overlap between segment areas, and the amount of unirradiated surface in areas between individual segment areas. Also, although the embodiments described herein each have had individual segment areas of a uniform size, a reflective optics design may be implemented to produce an array consisting of segment areas of different size, and/or carrying different amounts of light.

A simple and practical method of defining uniformity is therefore to consider the average irradiance within any single circular region located within the total area of the contact surface, said circular region comprising no less than a quarter of the total surface area, regardless of the shape of the total surface area. For any such single region on the contact surface comprising a quarter of the total area, the average irradiance should be no less than 50% above or 50% below the average irradiance over the entire contact surface, for an advantageous device. A more advantageous device has an average irradiance for any single region of one quarter the total surface area that is no less than 25% above or 25% below the average irradiance over the entire contact surface. Most advantageously, the device has an average irradiance for any single region of one quarter the total surface area that is no less than 10% above or 10% below the average irradiance over the entire contact surface.

As demonstrated herein, a reflective optics design has been found which provides thinness, uniformity of irradiation, cooling capability, and large light-emitting surface area.

Twelfth Embodiment

Figure 17A:
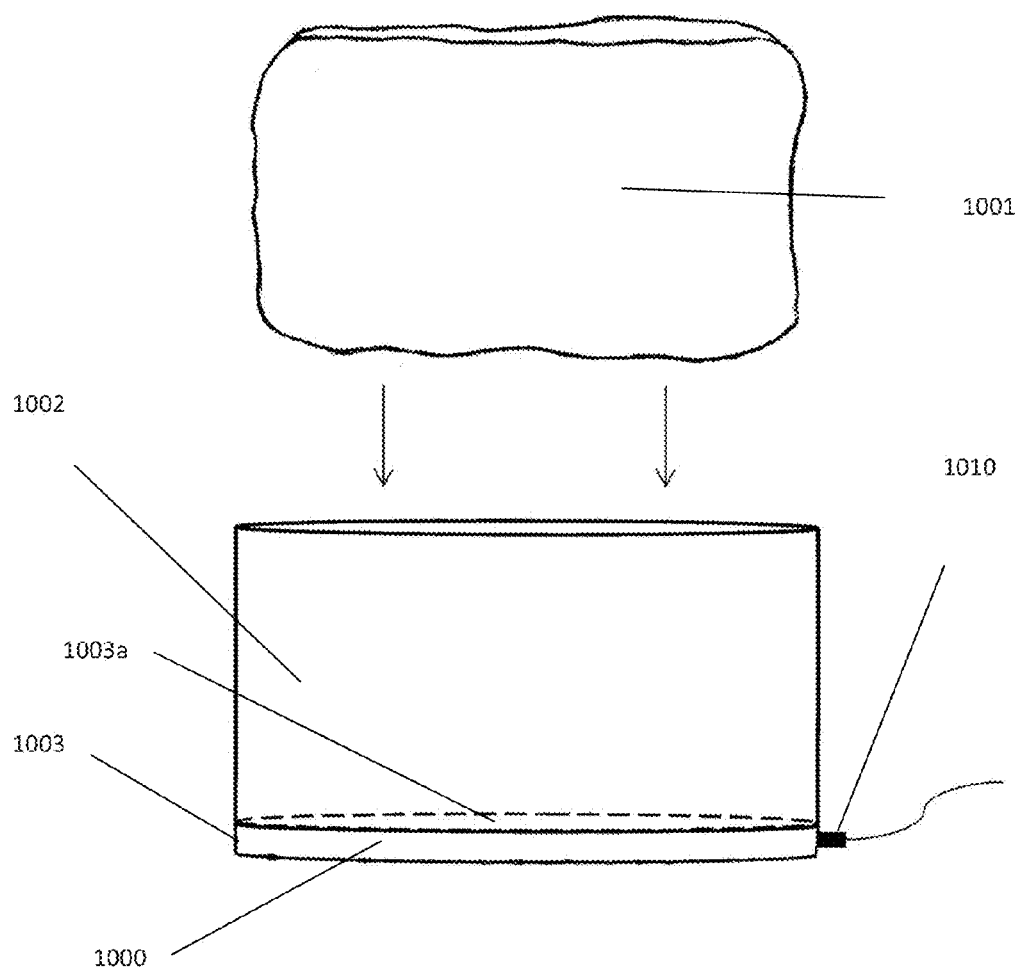
FIGS. 17A and 17B are schematic depictions of a twelfth apparatus comprising a detachable heat sink.

In the tenth embodiment shown schematically in FIG. 17A, the optical assembly (1000) is cooled with a detachable heat sink (1001). The heat sink (1001) is designed to be held on the top surface (1003a) of the housing (1003) of the optical assembly (1000), such that the heat sink is in good thermal contact with said surface. A frame or holder (1002) may be attached to the housing of the optical assembly to contain, hold, or support the heat sink in contact with said housing. The holder may have hollow cylindrical shape as depicted here, it completely enclose the heat sink, it may be an open frame, or it may have any other configuration suitable for holding the heat sink. Alternatively, the heat sink itself may comprise a frame or holder that attaches to the optical assembly. It is advantageous for the holder (1002) to be made of an insulating material, for example a plastic, to insulate the heat sink. In advantageous configurations, the holder may be permanently attached to the housing of the optical assembly. The holder (1002) may also be conveniently grasped by the operator when using the optical assembly. The optical assembly (1000) is attached by an optical fiber or other light transmission device (1010) to the light source.

The heat sink may be a sealed or closed pouch made of a flexible polymeric material, for example polyvinyl chloride, containing a gel, liquid, or frozen material, such as, for example, ice water, or cold pack gel material. An advantageous heat sink may be a plastic pouch containing crushed ice and water, sized and shaped to fit the holder (1002). More advantageously, the heat sink material may be any cold pack gel material known in the art, such as mixtures of water, salt and cellulose, mixtures of water and alcohol, vinyl-coated silica gel, and the like, that has a higher heat capacity than ice, and that is used as a cold compress or in beverage coolers, for example. The heat sink of the apparatus is designed to be placed in a refrigerator, freezer, or the like, to be brought to a low temperature prior to use. An advantageous gel material retains some malleability at the low temperature, so that it conforms readily to the top surface of the optical assembly. In this embodiment, the housing of the optical assembly has a top surface that is thermally conductive, for transmission of heat from the optical assembly contact surface, through the optical assembly, across the top surface, and to the heat sink. For example, the top of the housing may be made of metal.

The heat sink is cooled prior to attachment to the optical assembly, and requires no fluid flow or other cooling after attachment to the optical assembly or during irradiation to maintain tissue cooling capability. The present embodiment allows other cooling devices to be replaced by reusable heat sinks that may be stored at low temperature, attached to the optical assembly at the time of treatment, and returned to storage for later use. Advantageous aspects of embodiments using a detachable heat sink are that the apparatus does not require a cooling device or consumables, and energy consumption are minimized.

Figure 17B:
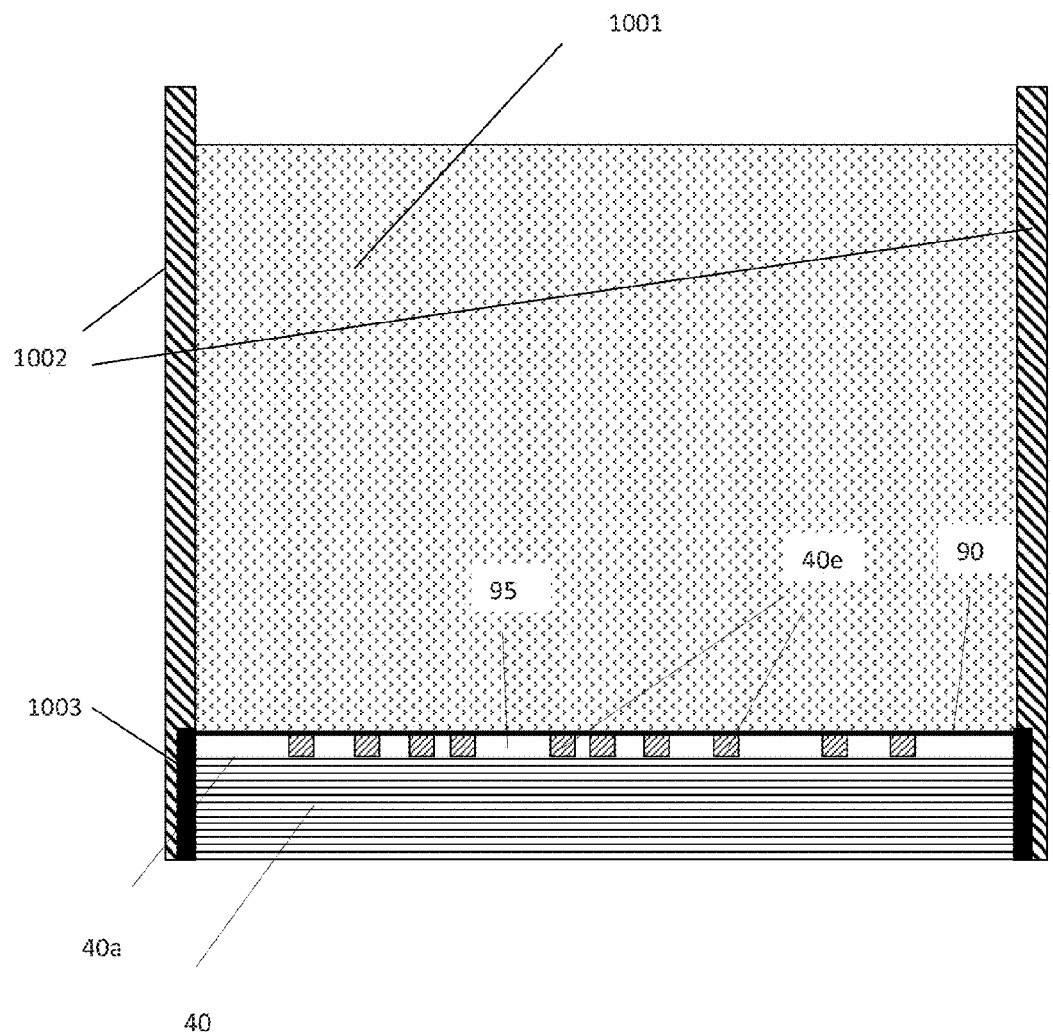

The capability of using a detachable heat sink for cooling directly through the optical assembly over the tissue irradiation site during irradiation is made possible by the novel low profile design of the optical assembly. A detachable heat sink can be used with any of the optical assemblies disclosed herein. Particularly advantageous optical assemblies for use with a heat sink are those of embodiments that do not have a cooling layer, for example the first embodiment. Also particularly advantageous is a light guide plate with applied extraction features in thermal contact with a reflecting plate, as in the sixth embodiment, but with no cooling layer and with the metallic reflecting plate exposed in an opening in the housing, so that said reflective plate is in direct contact with the heat sink. FIG. 17B is a schematic depiction. The extraction features (40e) of the proximal surface (40a) of a light guide plate (40) are in contact with the reflective plate (90) adjacent to the extraction space (95). The optical elements of the optical assembly are in a housing (1003) that is attached to the holder (1002) containing a heat sink (1001). The heat sink is in contact with the reflective plate (90).

Thirteenth Embodiment

In an apparatus intended to treat a superficial surface of a lumen or hollow organ, at least one optical assembly, and more advantageously a plurality of optical assemblies, may be disposed on an expanding element attached to the distal end of flexible elongated device, such as a catheter.

Figure 18A:
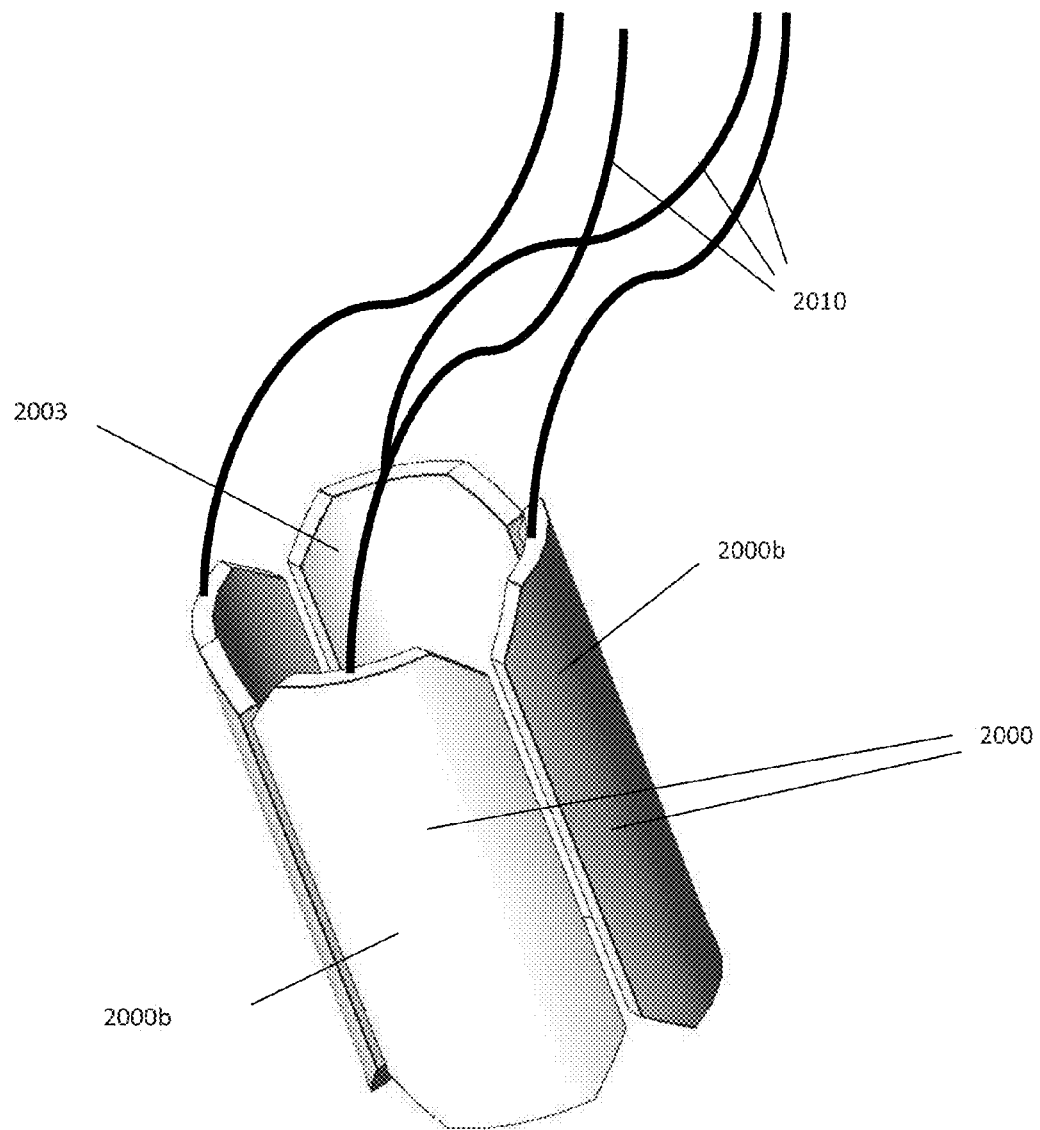
FIG. 18A-18D are schematic depictions of a thirteenth apparatus that includes a plurality of optical assemblies arranged for treatment of a lumen.
Figure 18B:
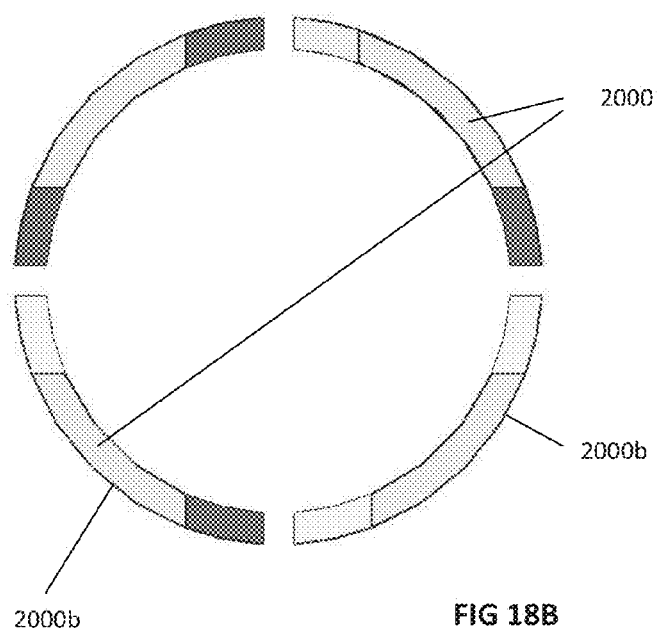
Figure 18C:
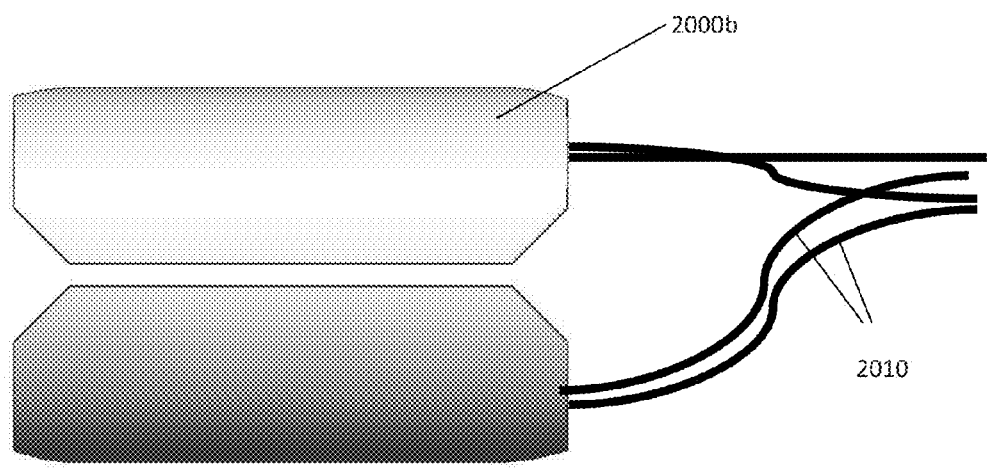

FIG. 18A is a schematic depiction of a device of this embodiment. Four optical assemblies (2000) are disposed in a circular arrangement, such that the light-transmitting surface elements (2000b) of the assemblies are facing outwards. The inner surfaces of the cylindrically shaped arrangement comprise the housings (2003). Each optical assembly is connected to an optical fiber (2010). End and side views are shown in FIGS. 18B and 18C, respectively.

Figure 18D:
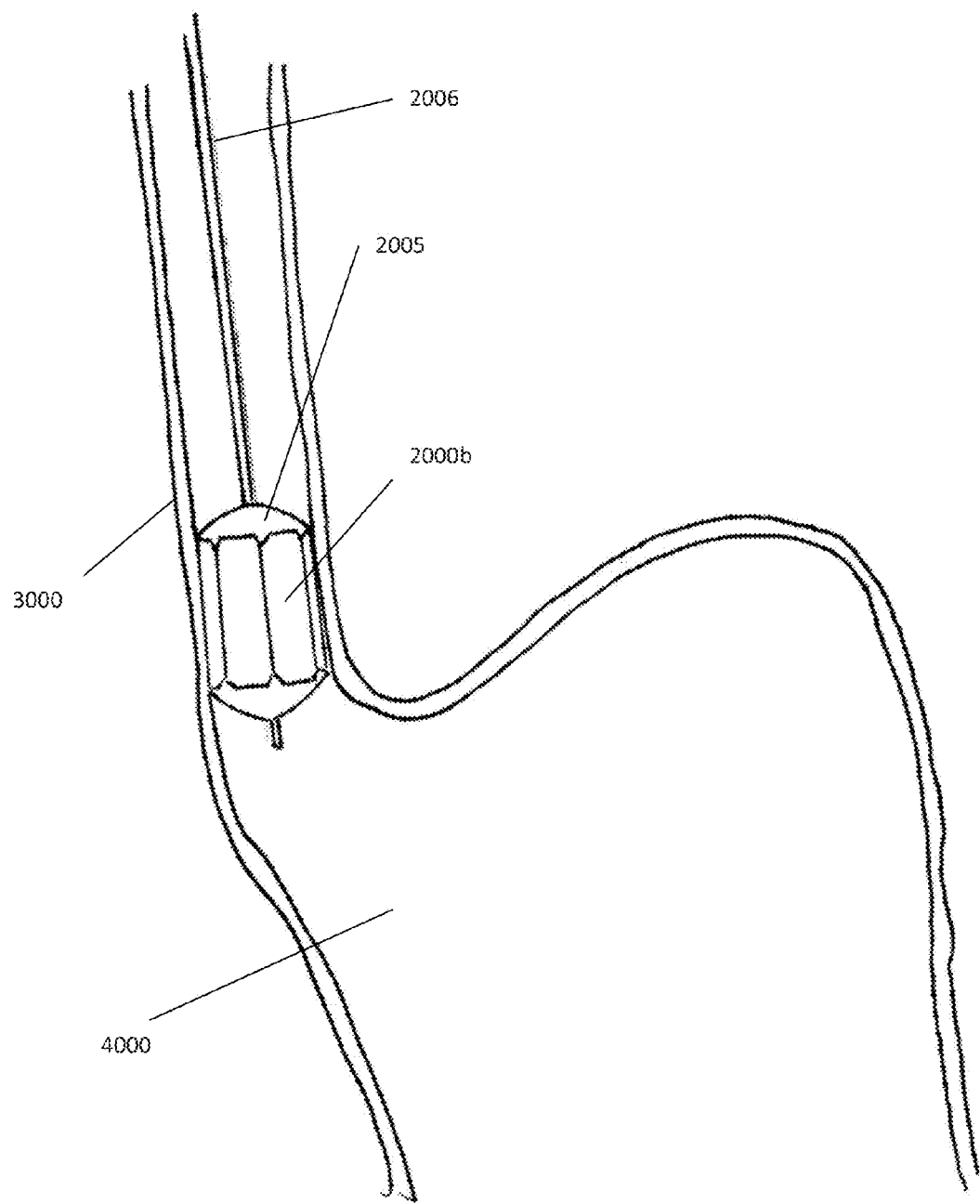

FIG. 18D depicts the assemblies as they may be used in a medical procedure. Here the stomach (4000) and esophagus (3000) are depicted. The optical assemblies (2000) are attached or tethered to a balloon (2005), such that when the balloon is expanded the light-transmitting surface elements are in contact with the esophageal inner wall. The balloon and attached optical assemblies are attached to a catheter 2006. An advantageous aspect of the invention is that the use of optical assemblies emitting light with substantially Lambertian output can be used to irradiate tissue when said tissue is not entirely in contact with the light emitting contact surface, since the intensity of the Lambertian output decreases rapidly with distance from the tissue. If there is a gap or space between a portion of the tissue and the contact surface, the light intensity at that surface portion will be significantly reduced and unlikely to produce unintended thermal damage.

This embodiment may be used to treat the tissue of Barrett's esophagus, for example, or dysplasia of the esophagus. With the patient under sedation, the distal esophagus is inspected with a standard endoscope to determine the extent and location of abnormal mucosal tissue. A guidewire may be inserted and the endoscope withdrawn. Then, an apparatus of FIG. 18C with deflated balloon is advanced over the guidewire and positioned so that the light emitting surface elements are at the level of abnormal mucosal tissue of the distal esophagus. With the balloon deflated, the optical assemblies may partially overlap so that the diameter is smaller than that of the esophagus. The balloon is inflated to bring the optical assemblies into position with the light emitting elements in contact with the abnormal mucosa. The light source of the apparatus is then activated and the abnormal mucosa is irradiated to damage or destroy the abnormal mucosal tissue.

For treatment of the esophagus, a plurality of optical assemblies disposed to provide a substantially circular arrangement of light-emitting contact surfaces with diameter ranging from about 20 mm to about 36 mm may be advantageous. For example, the apparatus may comprise four to eight optical assemblies, each approximately 18 mm in length and 8 mm in width and curved, so that a circular arrangement of contact surface having diameter of about 20 mm can be achieved. For treating a larger esophagus, the apparatus may have more optical assemblies and/or wider optical assemblies. The length of each assembly can be any length that is advantageous; for the esophagus lengths in the 1 cm to 3 cm range may be most advantageous. An aspect of the invention is that a set of variously sized optical assemblies can be used with the light source of the apparatus to treat patients.

The optical assemblies of an apparatus for treatment of a lumen may be those of any of the previously embodiments of the invention. The optical assemblies are sufficiently thin that when arranged with their light-emitting surfaces in a non-overlapping manner, a central space between the assemblies is available for an expanding element such as a balloon. A thickness of about 6 mm or less is advantageous for the optical assemblies. More advantageously, the optical assemblies are about 4 mm thick.

The optical assemblies may comprise cooling layers. Alternatively, an assembly of the first embodiment, where the light-emitting contact surface is the distal surface of the light guide plate and there is no cooling layer, may be advantageous for its thinness. In some embodiments, the optical assemblies of the apparatus are not actively cooled.

The light from a light source may be transmitted simultaneously to a plurality of optical assemblies using beamsplitters, including fiberoptic beamsplitters. More advantageously, a scanner can be used to distribute the light sequentially to each of the optical fibers associated with the plurality of optical assemblies. In this manner, the light of the light source is transmitted to each of the optical assemblies in a sequential manner. In this advantageous embodiment, the light source for a plurality of optical assemblies does not need to have total power substantially higher than required for the light-transmitting surface area of a single optical assembly. The scanner can be operated at a scan rate corresponding to different dwell times on the optical fiber input ends. Most advantageously, for a selected light source power, the scan rate corresponds to an irradiation time for each of the optical assemblies that is sufficient for the desired tissue effect (ablation, coagulation, thermal injury, and the like).

FIGS. 18A-18D depict a simple apparatus of this embodiment, with a balloon as the expanding element. In this embodiment, the balloon may be expanded or inflated using air delivered by the catheter.

The light source of the embodiment may be of any wavelength that is advantageous for tissue effect. For BE, it may be advantageous to ablate the mucosal tissue to a depth of 0.5 mm to 1.0 mm. For example, in treatment of BE, the 532 nm wavelength of a CW KTP laser may be advantageous for ablation of BE tissue which has increased vascularity. Other advantageous light sources include pulsed KTP, pulsed dye lasers, filtered flashlamps, or other pulsed sources with wavelength absorbed by hemoglobins, to produce a tissue effect of selective vascular injury that may be advantageous in treating malignant or premalignant tissues. An aspect of the invention is that the optical assembly can be used to transmit high energy, high power, and high peak power light pulses. Other advantageous light sources include lasers with more deeply penetrating wavelengths for treatment of thicker tumors in a lumen or hollow organ.

Fourteenth Embodiment

In an apparatus intended to treat a superficial surface of a lumen or hollow organ, at least one optical assembly, and more advantageously a plurality of optical assemblies, may be disposed on an expanding element attached to a flexible elongated device, such as a catheter, and a disposable sleeve covers at least the optical assemblies.

Figure 19:
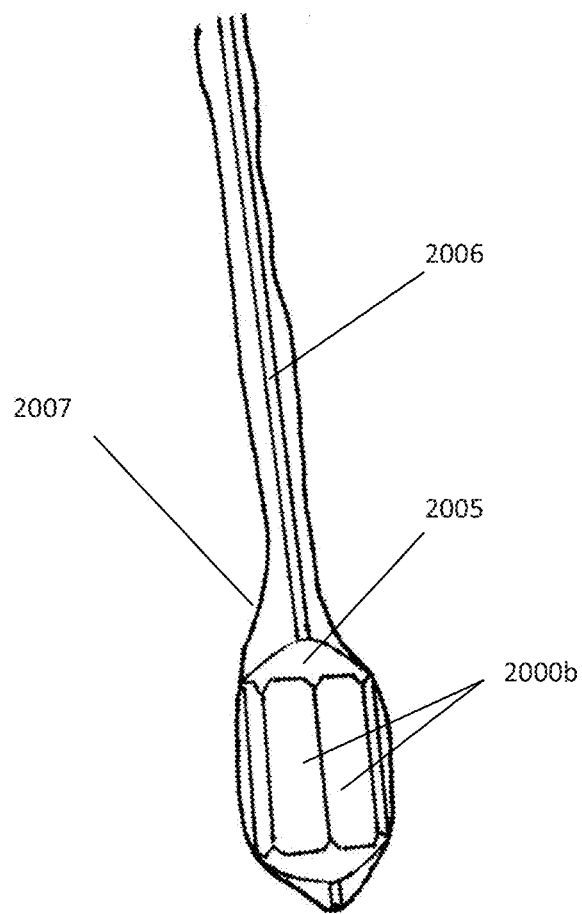
FIG. 19 is a schematic depiction of an apparatus of the fourteenth embodiment, comprising a plurality of optical assemblies arranged for treatment of a lumen and a disposable sleeve.

The disposable sleeve (2007) is depicted in FIG. 19, for the apparatus shown in FIG. 18. The sleeve may be placed over the distal end of the catheter, covering at least the light-transmitting surface elements of the optical assemblies, prior to the insertion of the catheter into the esophagus. The procedure is otherwise performed as described for the thirteenth embodiment.

A significant advantage of the present embodiment is that the sleeve protects the optical assemblies from exposure to body fluids or potentially infectious materials, such that time consuming or harsh sterilization procedures can be avoided, and the optical assemblies can be reused for cost savings.

EXEMPLIFICATION

In the following examples, optical modelling is used to determine the performance of optical assemblies. The examples do not represent all of the embodiments, rather, the examples are an analysis of a limited range of embodiments, demonstrating the effect of design changes on device performance.

Example 1

In a first example, a device of the first embodiment produces an irradiated spot on a tissue surface of approximately 18 mm length by 8 mm width, using the output from a single 275 μm core diameter, 0.22 NA silica optical fiber coupled to a CW quantum dot diode laser operating at 1120 nm at power of 10 W (Innolume GmbH, Dortmund, Germany). The device has a cooled surface in contact with the tissue surface at the irradiated spot. The total height of the device of this example, measured in a dimension normal to the plane of the tissue surface, is approximately 5 mm, which is smaller than the length or width of the irradiated spot on the tissue surface.

Figure 20A:
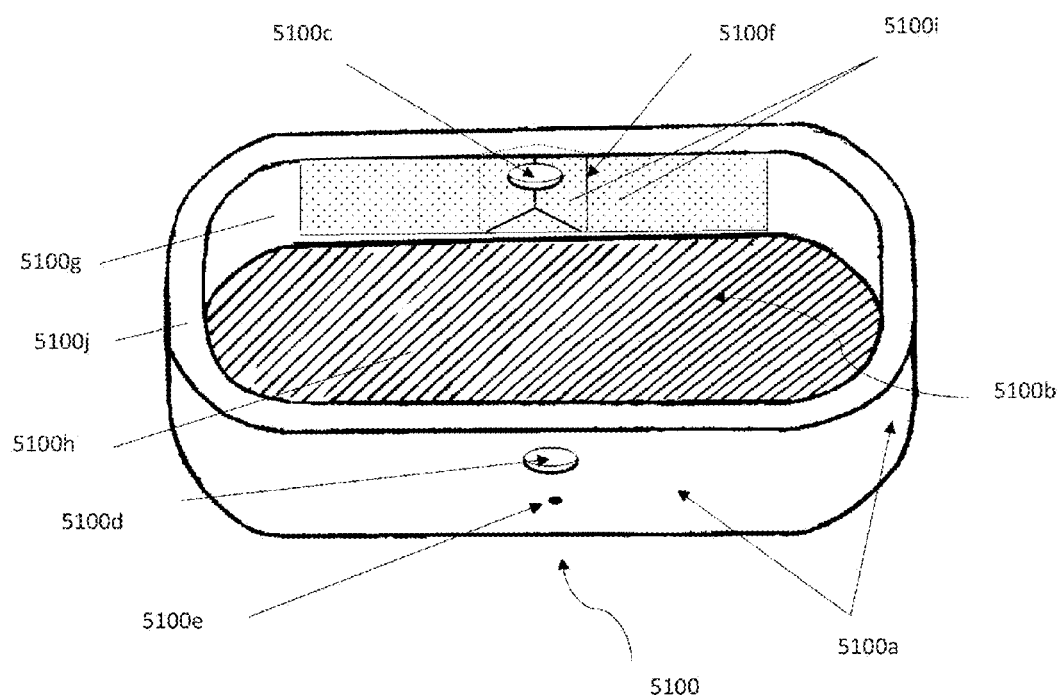
FIG. 20A-20D are semi-schematic drawings of the first example optical assembly.

FIG. 20A depicts the housing of the device of this example. The housing (5100) has lateral walls (5100*a*) and base (5100*b*) that are approximately 1 mm in thickness. The housing has interior dimensions of 18 mm length and 8 mm width, with a 3 mm radius fillet on the corners, and an exterior height of approximately 5 mm. On opposite sides of the lateral walls of the housing are openings (5100*c*, 5100*d*) for entrance and exit of coolant fluid. These openings are 1 mm in diameter.

Also on the lateral wall is an opening (5100*e*) for entrance of light from the optical fiber of the laser light source. The housing has a V-groove (5100*f*) on the portion of the lateral wall directly opposite the opening (5100*e*) for the optical fiber. The V-groove extends from a point on the lateral wall above the base interior surface (5100*h*) to a point below the rim (5100*j*) of the housing. The base interior surface (5100*h*) and lateral wall interior surface (5100*g*) of the housing are completely coated with Labsphere 6080 barium sulfate paint (Labsphere, North Sutton, N.H.), with the exception of a mirrored wall surface segment (5100*i*) on the lateral wall opposite the fiber entrance opening, comprising V-groove (5100*f*) surface and segments of the adjacent lateral wall surface on either side of the V-groove. The mirrored surface 5100*i* is 95% reflective Alanod material (ALANOD Aluminium-Veredlung GmbH, Germany).

Figure 20B:
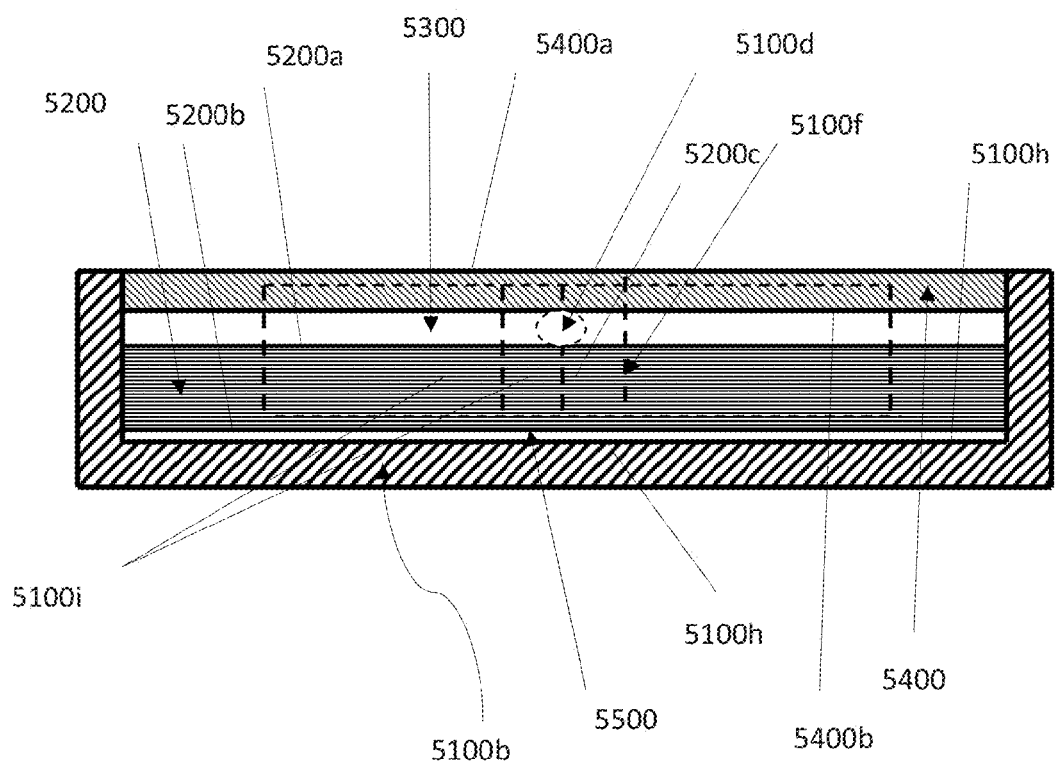

FIG. 20B is a cross sectional diagram of the optical assembly and housing of the device of this example. The proximal surface (5200*b*) of a 2 mm-thick light guide plate (5200) is separated by a minimal air gap from the base interior surface (5100*h*) of the base of the housing (5100*b*). A 1 mm-thick tissue contacting surface optic (5400) has a tissue contacting distal surface (5400*a*) and a coolant contacting proximal surface (5400*b*). The light guide plate (5200) is made of quartz, and the tissue contacting surface optic (5400) is a sapphire window. The proximal surface (5400*b*) of the sapphire window is separated from the distal (5200*a*) surface of the light guide plate by a 1 mm space that serves as a coolant flow chamber (5300). Both quartz and sapphire optics are plane parallel windows. The quartz light guide plate and sapphire window are held in contact with the housing lateral wall so that their plane surfaces are parallel. Projections of the Alanod mirrored surfaces (5100*i*) and the coolant flow opening centered in the V-groove (5100*d*) on to the cross section are indicated in FIG. 20B.

The entrance in the lateral wall for the optical fiber (5100*e*, shown in FIG. 20A) is positioned so that light exiting the fiber is centered on the quartz light guide plate lateral edge (5200*c*). The coolant entrance and exit holes (5100*c* and 5100*d*, respectively) in the housing lateral walls are aligned with the coolant flow chamber (5300). When coolant fluid enters the chamber (5300) at hole (5100*c*) it fills the chamber and the space between the light guide plate (5200) and tissue contacting optic (5400) and the V-groove (5100*f*) of the housing. Fluid is prevented from flowing from the V-groove into the air gap (5500) between the base interior surface (5100*h*) and the light guide plate proximal surface (5200*b*) by contact between the lateral walls (5100*a*) of the housing and the light guide plate (5200), in proximity to the housing base (5100*b*). Contact between the lateral walls (5100*a*) and the tissue contacting surface optic (5400) in proximity to the rim (5100*j*) of the housing prevents fluid from flowing out of the housing at the V-groove. Fluid flows out of the housing at exit hole (5100*d*). In the device of this example, the fluid is water. Water is used in this example because it is biocompatible and has a relatively low absorption of approximately 5% over a 1 mm path length at 1120 nm.

Figure 20C:
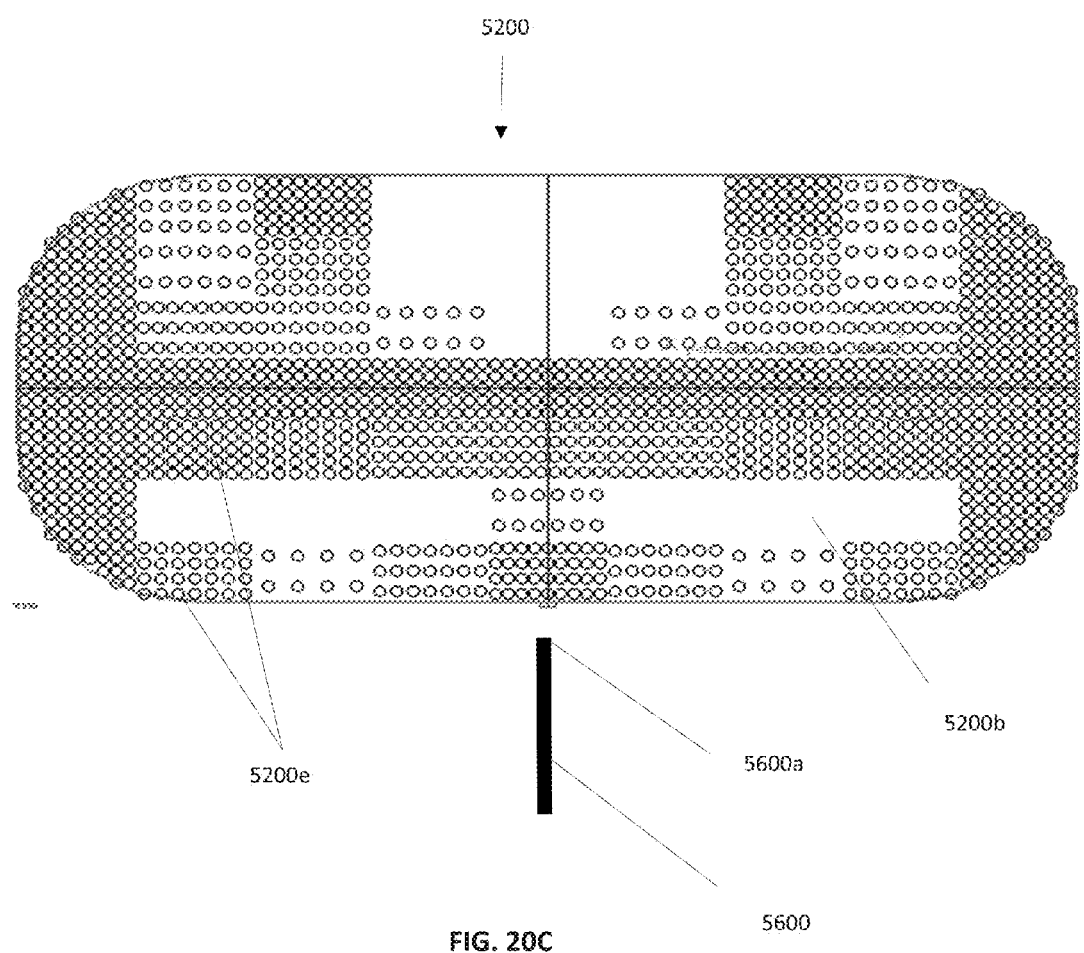

FIG. 20C is a schematic depiction of the light guide plate (5200). The proximal surface of the quartz light guide plate (5200*b*), adjacent to the base interior surface (5100*h*) but positioned with a minimal space (5500) from said base interior surface, has extraction features (5200*e*) applied using screen printing with Labsphere 6080 paint. The extraction features consist of a plurality of 200 micron diameter dots, arranged in a pattern. The dot arrangement is selected so that the device of the example produces an approximately 18 mm by 8 mm irradiated spot, with substantial uniformity of irradiation. The density and position of the paint dot pattern varies over the proximal surface of the light guide plate. The dot pattern is selected by using a Monte Carlo ray tracing program (Optical Research Associates, Pasadena, Calif.) to calculate the irradiance at the tissue contacting surface for various dot patterns, to determine the pattern best corresponding to uniform irradiance. The dots of FIG. 20C are enlarged for visibility. The position of the exit face (5600*a*) optical fiber (5600) of the laser relative to the light guide plate is indicated.

Figure 20D:
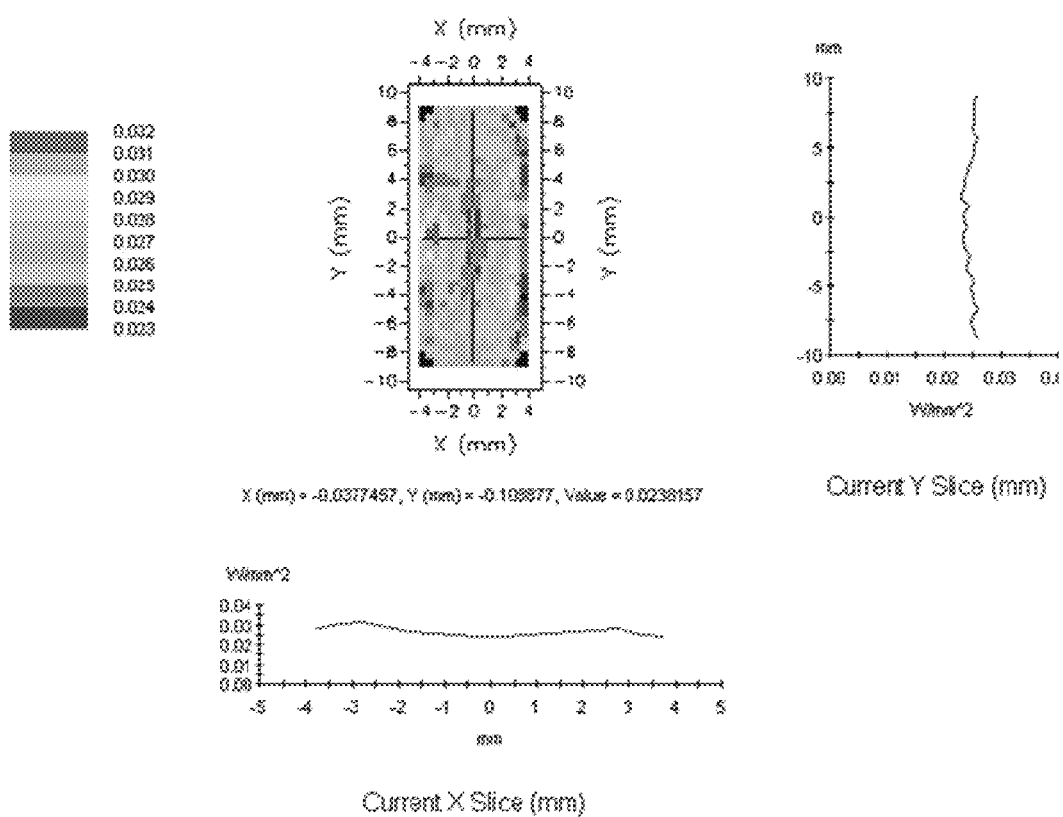

Results of the Monte Carlo calculations are shown in FIG. 20D, for the selected dot pattern shown in FIG. 20C. With laser light power entering the housing at 10 W, the average irradiance at the tissue contacting surface (400*a*) is calculated to be 0.026 W/mm$^2$, for an efficiency of 35%. With a bin size of 0.5 mm×0.5 mm, the maximum and minimum irradiance is 0.032 W/mm$^2$ and 0.023 W/mm$^2$, respectively. The uniformity of irradiance is +25%, −12%. The output is substantially Lambertian.

The device of this example has the disadvantage that the Labsphere 6080 coating of the housing lateral walls is exposed to water at the coolant chamber (300) and will erode with use. This disadvantage can be readily eliminated by using a reflective Alanod or gold mirror surface instead barium sulfate on all or part of the lateral walls of the housing, or by using Duraflect coating (Labsphere) instead of Labsphere 6080.

Example 2

The device of Example 1 has efficiency of 35%. The majority of light entering the housing is lost to absorption within the device rather than being emitted from the device. In an example of the second embodiment, a design with improved efficiency is described, for the same 1120 nm laser source and optical fiber as the device of Example 1. An advantage of this second example is that it reduces back scattering of light into the light guide plate and leakage of light out of the light guide plate, for reduced scattering within the device and increased transmission efficiency.

Figure 21A:
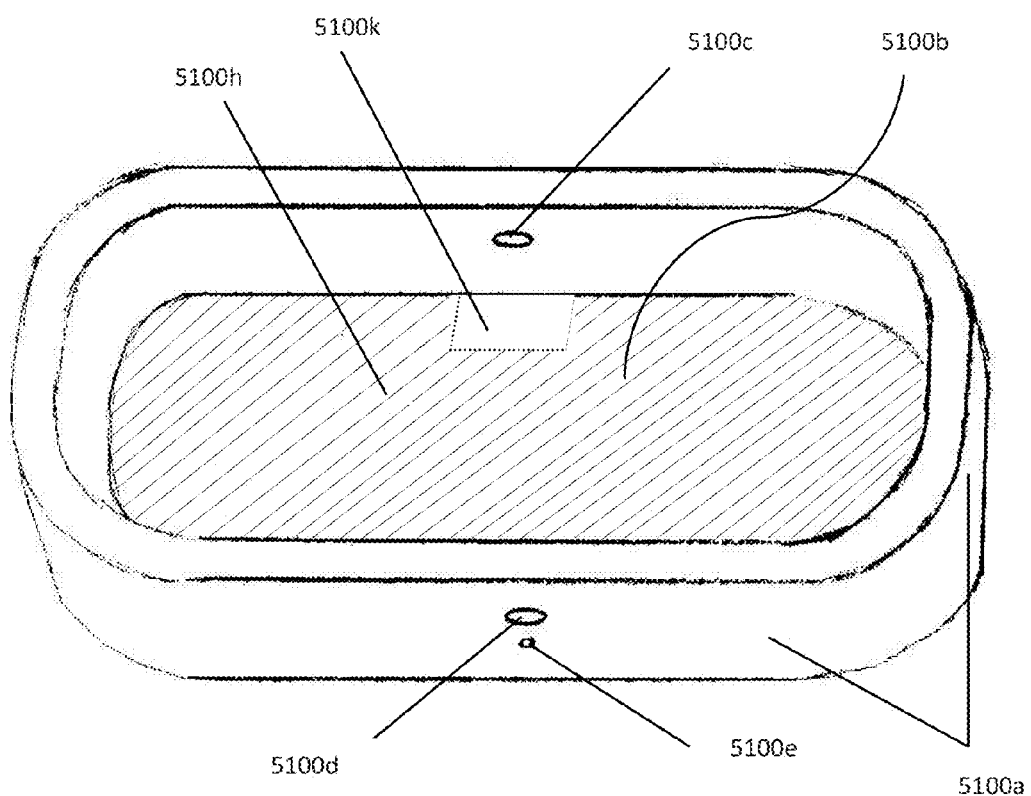
FIGS. 21A-21D are semi-schematic drawings of an optical assembly of the second example.

FIG. 21A depicts the housing of the device of this example. The housing has lateral walls (5100a) and base (5100b) that are approximately 1 mm in thickness. The housing has interior dimensions of 18 mm length and 8 mm width, with a 3 mm radius fillet on the corners, and an external height of approximately 5 mm. On opposite sides of the lateral walls of the housing are openings (5100c, 5100d) for entrance and exit of coolant fluid. These openings are 1 mm in diameter. Also on the lateral wall is an opening (5100e) for entrance of light from the optical fiber of the laser. The base interior surface (5100h) and lateral wall interior surface (5100g) of the housing are completely coated with Labsphere 6080 barium sulfate paint (Labsphere, North Sutton, N.H.), with the exception of a rectangular 4 mm by 2 mm unpainted area (5100k) on the base interior surface adjacent to the lateral wall opposite to the light entrance opening (5100e).

Figure 21B:
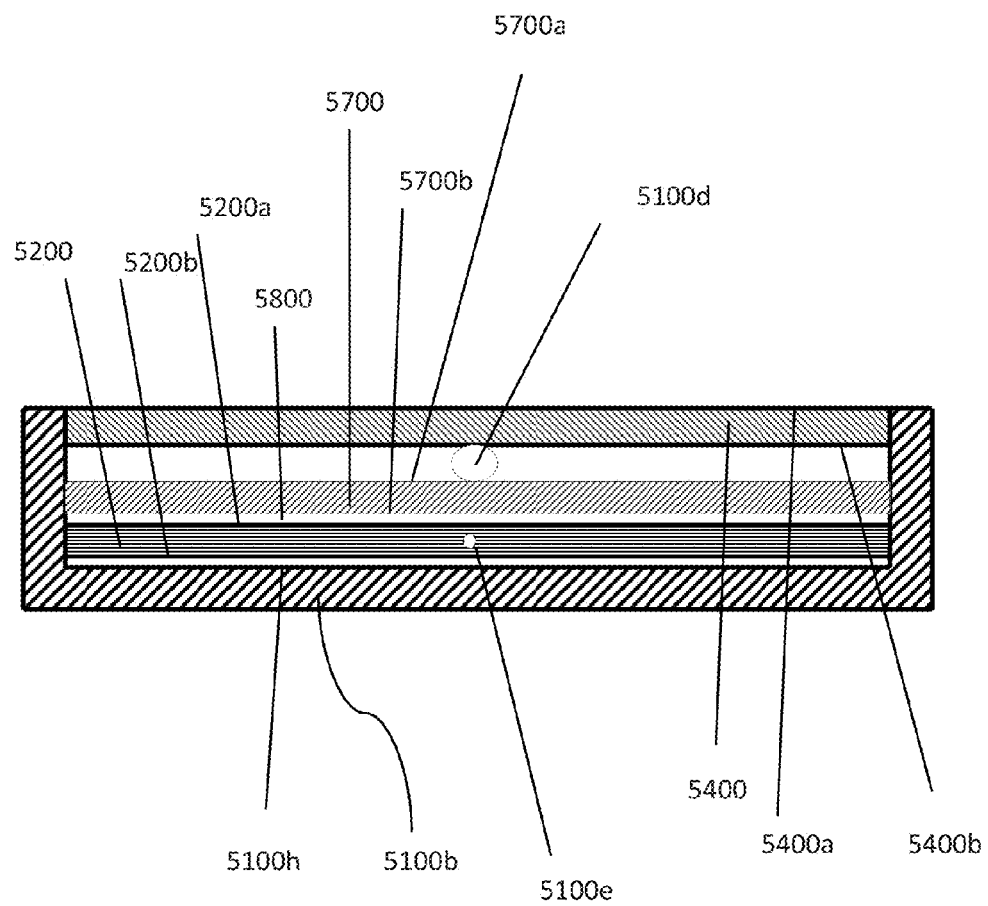

FIG. 21B is a cross sectional diagram of the optical assembly and housing of the device of this example. In near proximity to base interior surface (5100h) of the back of the housing (5100b) is the proximal surface (5200b) of a 1 mm-thick light guide plate (5200). The proximal surface (5700b) of a 1 mm-thick window plate (5700) is separated from the distal surface (5200a) of the light guide plate (5200) by an airspace (5800) of at least 2 microns thickness. The window plate (5700) has a distal surface (700a). A 1 mm-thick tissue contacting surface optic (5400) has a tissue contacting distal surface (5400a) and a coolant contacting proximal surface (5400b). The light guide plate (5200) and window plate (5700) are made of quartz, and the tissue contacting surface optic (5400) is a sapphire window. The proximal surface (5400b) of the sapphire window is separated from the distal surface (5700a) of the window plate by a 1 mm space that serves as a coolant flow chamber (5300). The quartz light guide plate (5200), quartz window (5700), and sapphire window (5400) are plane parallel windows. In the device of this example, the quartz light guide plate (5200) and quartz window (5700) are identical. The quartz light guide plate, quartz window and sapphire window are held fixed in contact with the housing lateral wall so that they are parallel to each other.

The entrance in the lateral wall for the optical fiber (5100e), projected in FIG. 21B, is positioned so that light exiting the fiber is centered on the quartz light guide plate lateral edge. The coolant entrance and exit hole in the housing lateral walls are aligned with the coolant flow chamber. The coolant exit hole (5100d) is projected on the coolant flow chamber in FIG. 21B. When coolant fluid enters the chamber (5300) at the entrance hole it fills the chamber and flows out at exit hole. In the device of this example, the fluid is water.

Figure 21C:
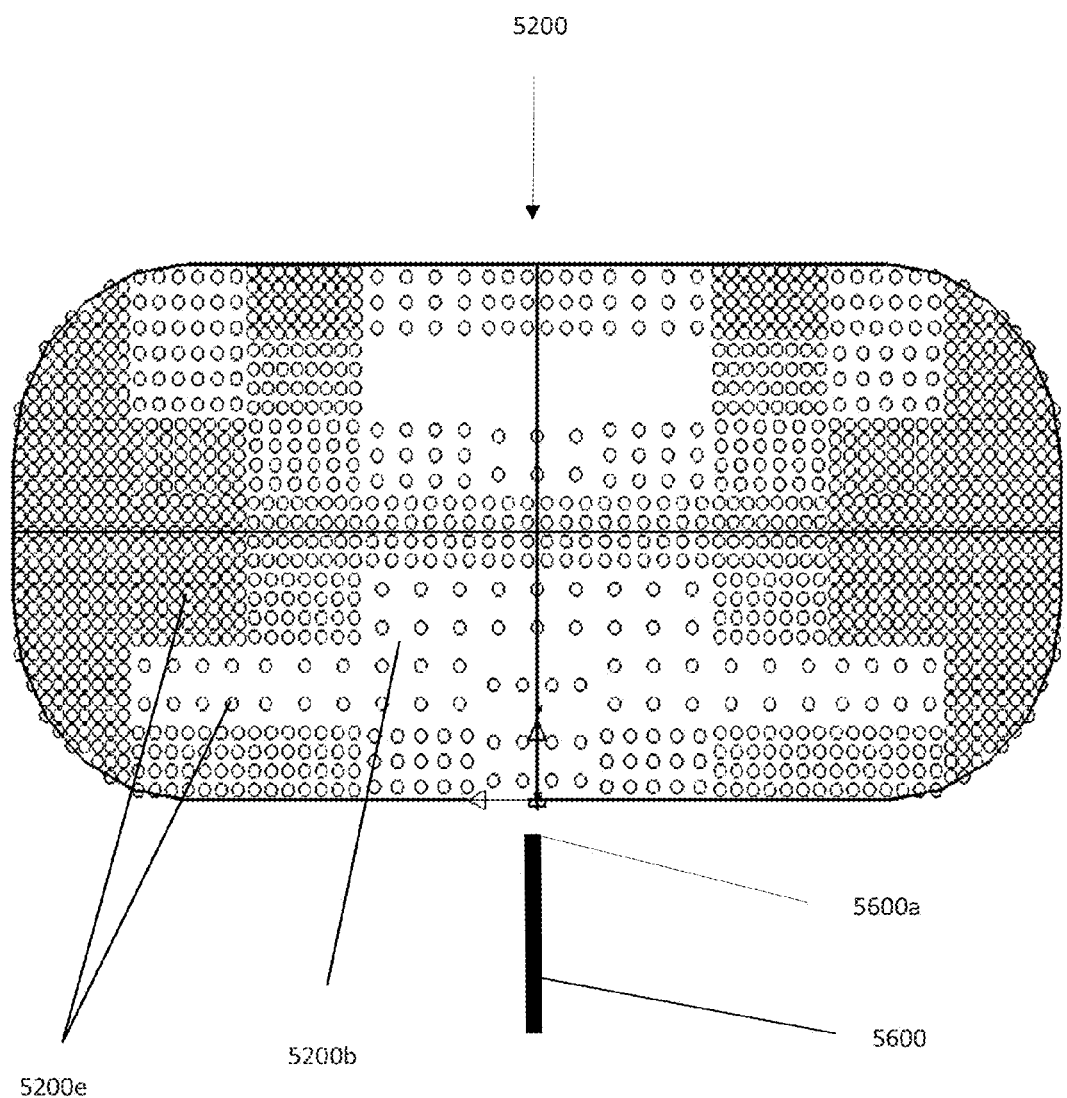

FIG. 21C is a schematic depiction of the extraction features (5200e) on the proximal surface (5200b) of the quartz light guide plate (5200). The exit face (5600a) of the optical fiber (5600) is adjacent to the lateral edge of the light guide plate. The extraction features are paint dots applied by screen printing using Labsphere 6080 paint. Each paint dot is 200 microns in diameter and is expanded in size in the figure for visibility. The arrangement of the paint dots was selected on the basis of Monte Carlo ray tracing (Optical Research Associates, Pasadena, Calif.), and can be seen to differ from the arrangement of dots in the device of example 1.

Figure 21D:
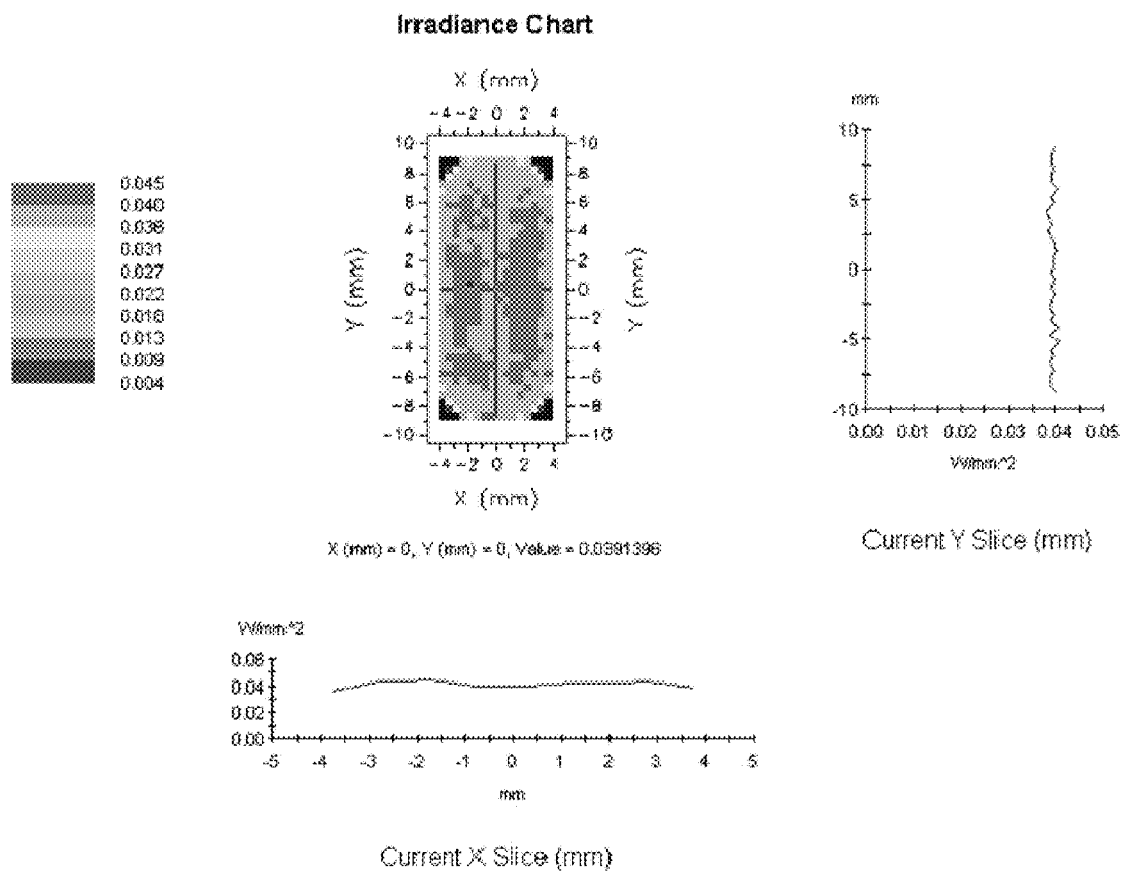

The optical characteristics of the probe of this example (FIG. 21D) are improved in both efficiency and uniformity of irradiance, compared to the device of example 1. The efficiency of the device of this example is 54%. With a 10 W input at 1120 nm, the maximum and minimum irradiance is 0.045 and 0.031 W/mm$^2$, respectively. The average irradiance is 40 mW/mm$^2$. Uniformity is +12%, −22%. The intensity profile is substantially Lambertian.

Example 3

This example of the second embodiment uses as light source the 1120 nm quantum dot diode laser of Examples 1 and 2, but with a 200 micron core diameter, 0.53 NA optical fiber (Ceramoptic WF 200/220 HT 53) instead of the 0.22 NA fiber of the earlier examples. Also, the cooling fluid in the present example is perfluorocarbon (Fluorinert, 3M, Minneapolis, Minn.), which has negligible absorption at 1120 nm. Further changes have been made to the coatings and surfaces of the housing and optics.

Figure 22A:
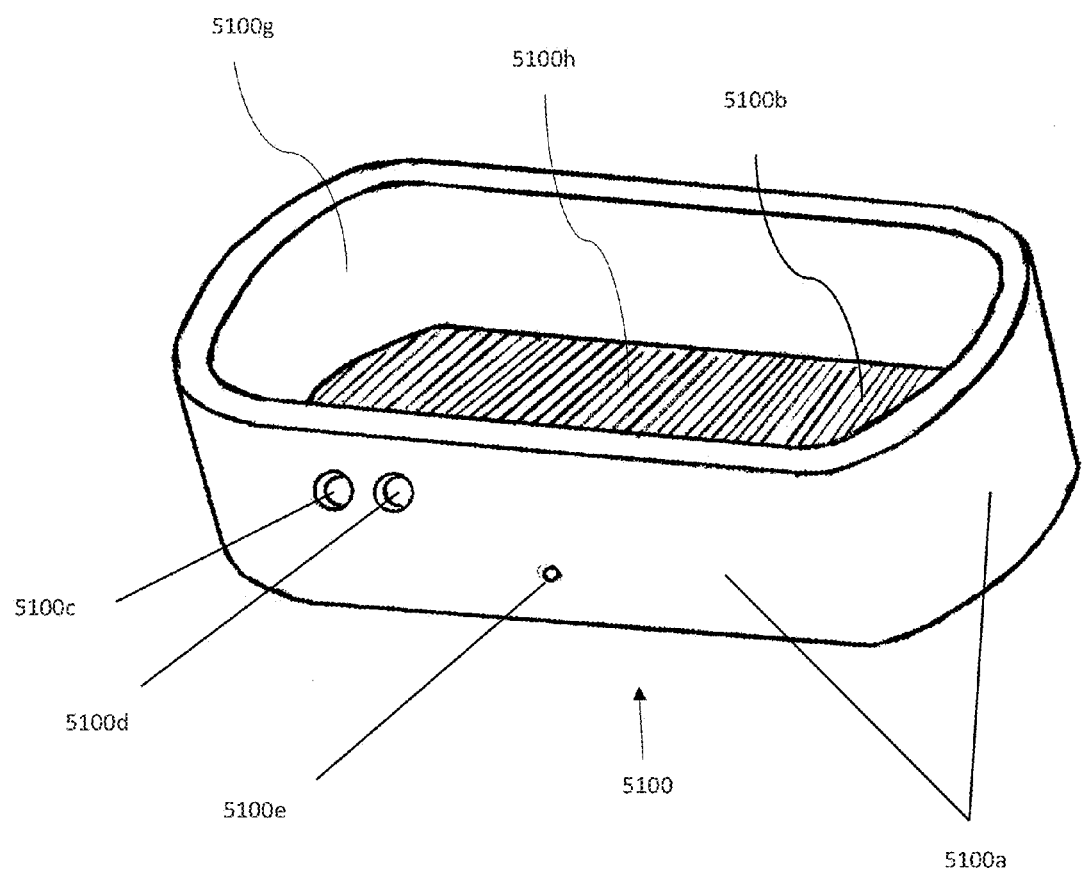
FIG. 22A-22G are semi-schematic drawings of an optical assembly of the third example.

FIG. 22A depicts the housing of the device of this example. The housing (5100) has lateral walls (5100a) and base (5100b) that are approximately 1 mm in thickness. The housing has interior dimensions of 18 mm length and 8 mm width, with a 3 mm radius fillet on the corners, and a height of approximately 5 mm. On the lateral wall of the housing are adjacent openings (5100c, 5100d) for entrance and exit of coolant fluid. These openings are 1 mm in diameter, and are positioned near the end of a flat segment of the lateral wall. Near the center of the same flat segment of the lateral wall is a 0.55 mm diameter opening (5100e) for entrance of light from the optical fiber of the laser. The base interior surface (5100h) of the housing is completely coated with Labsphere 6080 barium sulfate paint (Labsphere, North Sutton, N.H.), and the lateral wall interior surface (5100g) has an optically specular polish with protective gold coating.

Figure 22B:
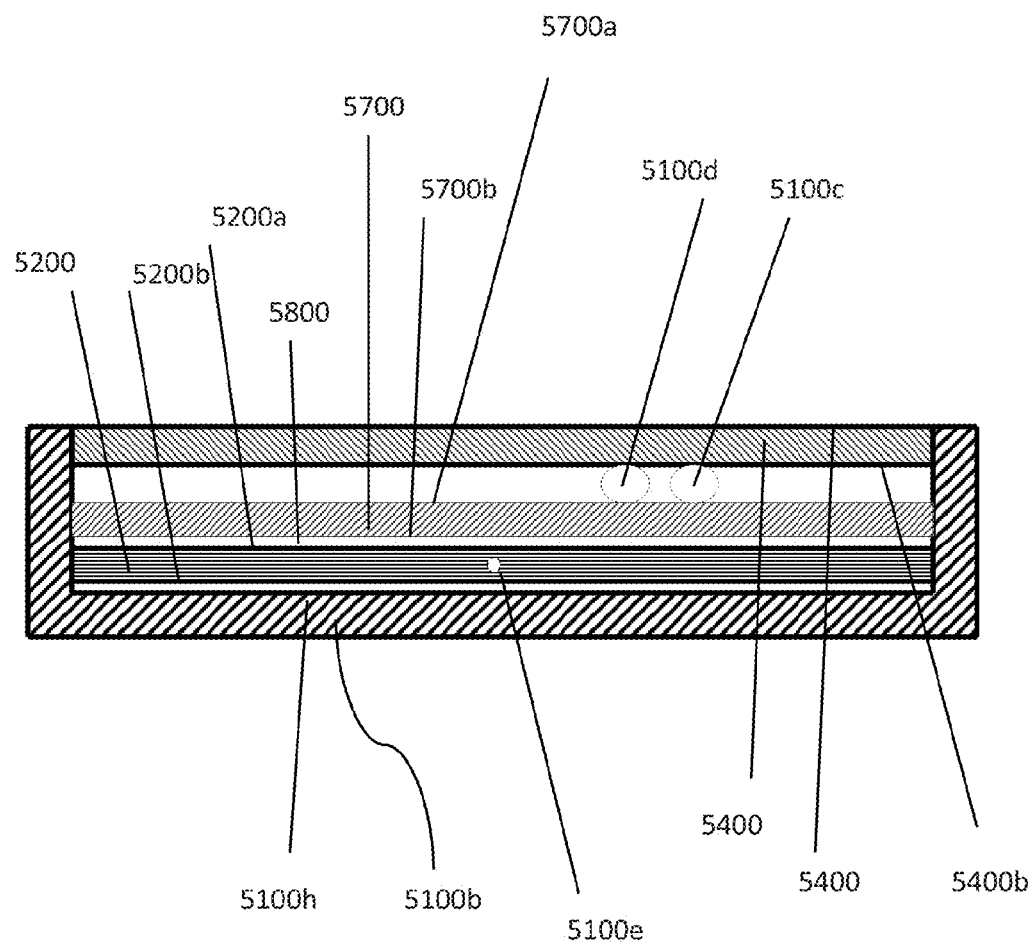

FIG. 22B is a cross sectional diagram of the optical assembly and housing of the device of this example. The arrangement of optical components in the device of this example is similar to that of example 2 with the exception of the placement of the coolant flow openings (5100c, 5100d), which are indicated as projections in this diagram. In near proximity to base interior surface (5100h) of the back of the housing (5100b) is the proximal surface (5200b) of a 1 mm-thick light guide plate (5200). The proximal surface (5700b) of a 1 mm-thick window plate (5700) is separated from the distal surface (5200a) of the light guide plate (5200) by an airspace (5800) of at least 2 microns thickness. A 1 mm-thick tissue contacting surface optic (5400) has a tissue contacting distal surface (5400a) and a coolant contacting proximal surface (5400b). The light guide plate (5200) and window plate (5700) are made of quartz, and the tissue contacting surface optic (5400) is a sapphire window. The proximal surface (5400b) of the sapphire window is separated from the distal surface (5700a) of the window plate by a 1 mm space that serves as a coolant flow chamber (5300). The quartz light guide plate (5200), quartz window (5700), and sapphire window (5400) are plane parallel windows. In the device of this example, the quartz light guide plate (5200) and quartz window (5700) are identical. The quartz light guide plate, quartz window and sapphire window are held fixed in contact with the housing lateral wall so that they are parallel to each other.

The entrance in the lateral wall for the optical fiber (5100*e*), projected in FIG. 22B, is positioned so that light exiting the fiber is centered on the quartz light guide plate lateral edge. The coolant entrance and exit holes in the housing lateral walls are aligned with the coolant flow chamber (5300). When coolant fluid enters the chamber (5300) at hole (5100*c*) it fills the chamber and flows out at exit hole (5100*d*). In the device of this example, the fluid is perfluorocarbon, for example FC-43 (Fluorinert, 3M, Minneapolis, Minn.).

Figure 22C:
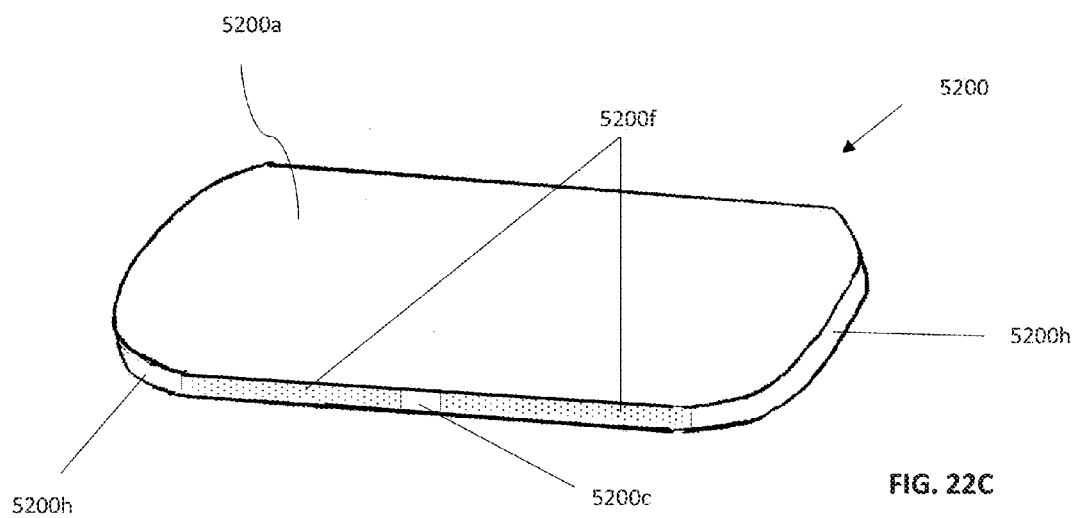
Figure 22D:
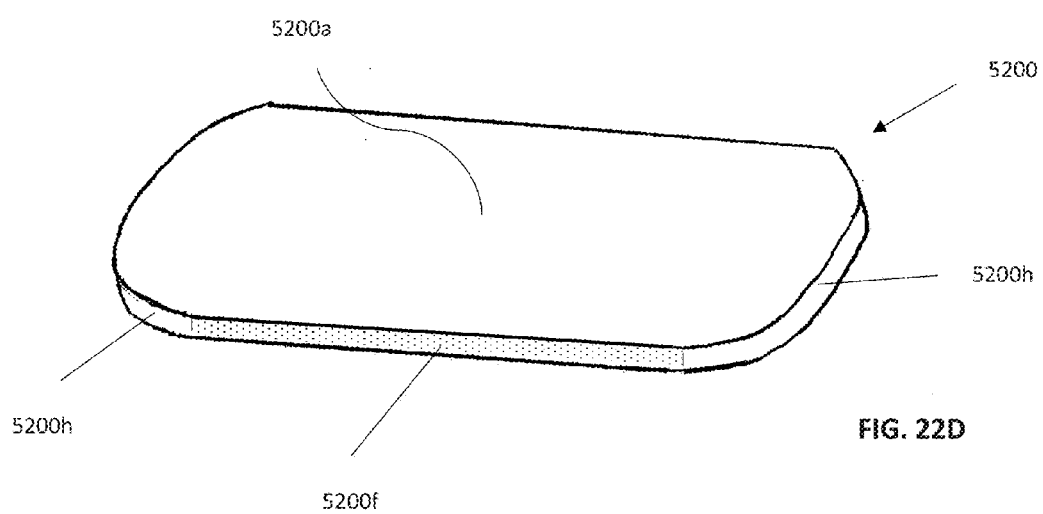

The lateral edges of the sapphire window and quartz coolant window are optically smooth polished. The lateral walls of the light guide plate (5200) have protected gold coating on flat segments parallel to the long axis (5200*f*), with the exception of a small (1 mm by 1 mm) uncoated area (5200*c*) where light from the fiber enters the light guide plate (FIG. 22C, rotated view FIG. 22D). The surfaces of the lateral walls at the ends of the light guide plate (200*h*) are coated with Labsphere 6080 paint. The gold coated edges of the light guide plate are optically smooth and the paint coated end edges are unpolished.

Figure 22E:
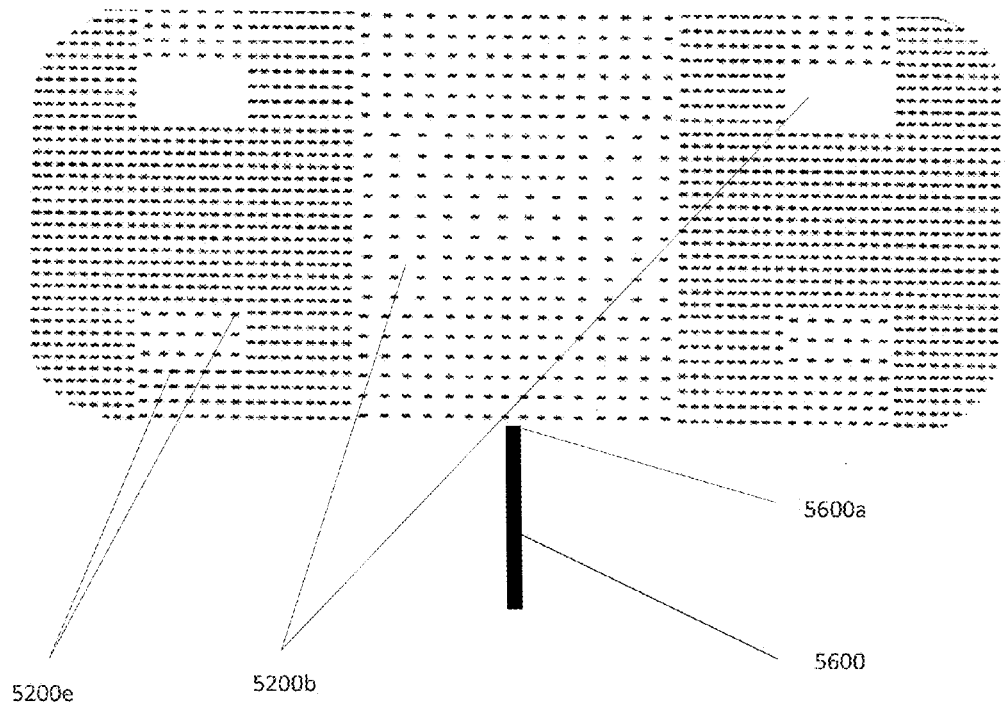

The proximal surface (5200*b*) of the light guide plate has extraction features in the form of Labsphere 6080 paint dots (200 micron dot diameter). The pattern of paint dots is schematically indicated in FIG. 22E, with the size of the dots enlarged for visibility. The pattern was selected on the basis of Monte Carlo ray trace calculations (Optical Research Associates, Pasadena, Calif.), for efficiency and uniformity of output.

Figure 22F:
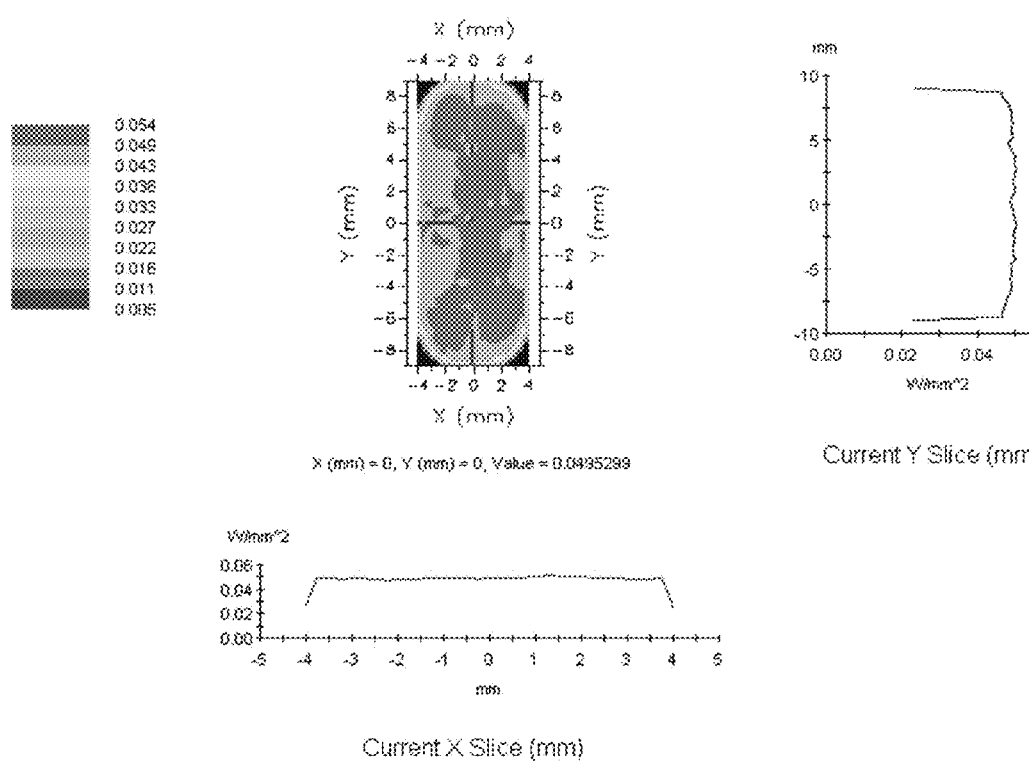

The results of the model calculations for the device of this example are shown in FIG. 22F. The optical characteristics are improved in both efficiency and uniformity of irradiance, compared to the devices of example 1 and 2. The efficiency of the device of this example is 67%. With a 10 W input, the maximum and minimum irradiance is 0.054 and 0.044 W/mm$^2$, respectively. The average irradiance is 40 mW/mm$^2$. Uniformity is +10.5%, −9.5%. The intensity profile is substantially Lambertian.

An advantage of this example is that diffuse coating white paint (Labsphere 6080) is limited to the interior base surface of the housing and a portion of the quartz light guide plate lateral edges. A subsequent reduction in scattering losses results in improved efficiency. The diffuse coated surfaces are well isolated from the coolant fluid.

Figure 22G:
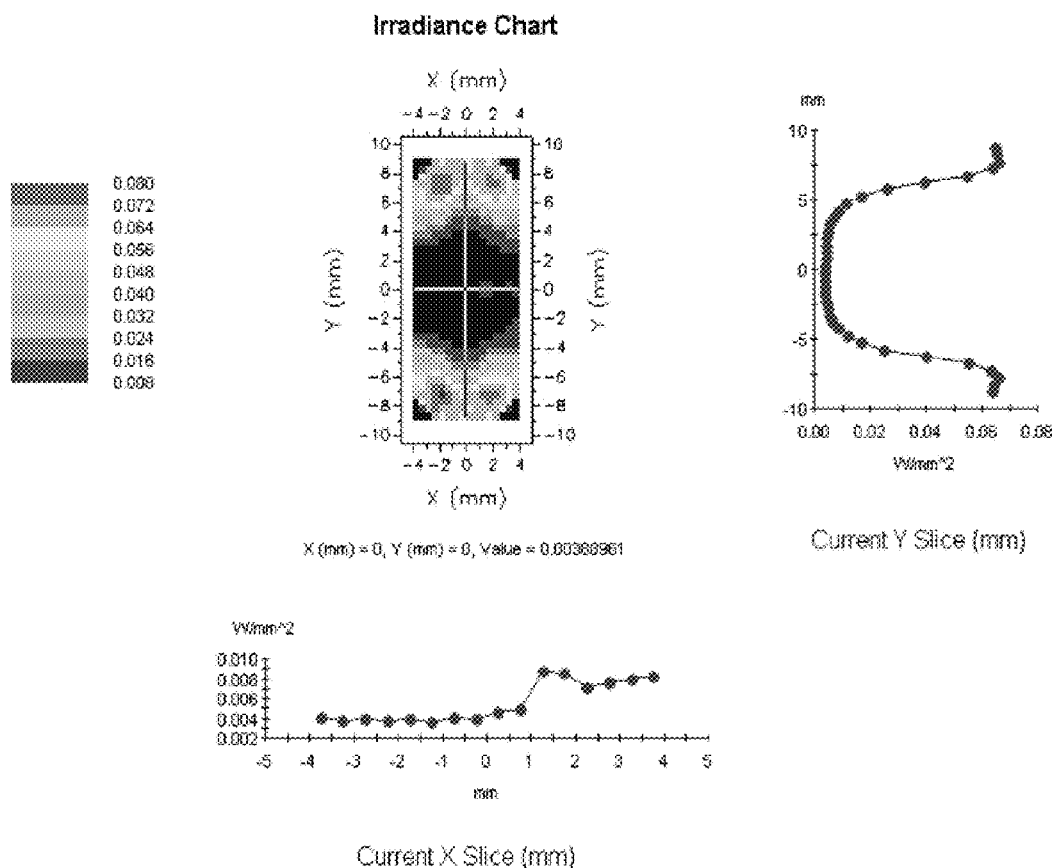

The importance of the extraction features on the light guide plate as a component of the device can be demonstrated by performing the Monte Carlo calculation on a device that is identical to that of this example with the exception that the paint dots are eliminated. Results are shown in FIG. 22G; the irradiance at the distal surface (5400*a*) of the tissue contacting sapphire window (5400) is highly asymmetrically distributed, with a substantially lower irradiance in the central region of the surface.

Example 4

In this example of the second embodiment, a device with circular shape is described. The light-emitting surface has a diameter of 13.5 mm, making that surface area approximately equal to the light-emitting surface of the 18 mm×8 mm device of the previous examples. The laser is an 1120 nm dot laser (Innolume, Dortmund, Germany) coupled to a 200 micron core diameter, 0.53 NA optical fiber (Ceramoptic WF 200/220 HT 53).

Figure 23A:
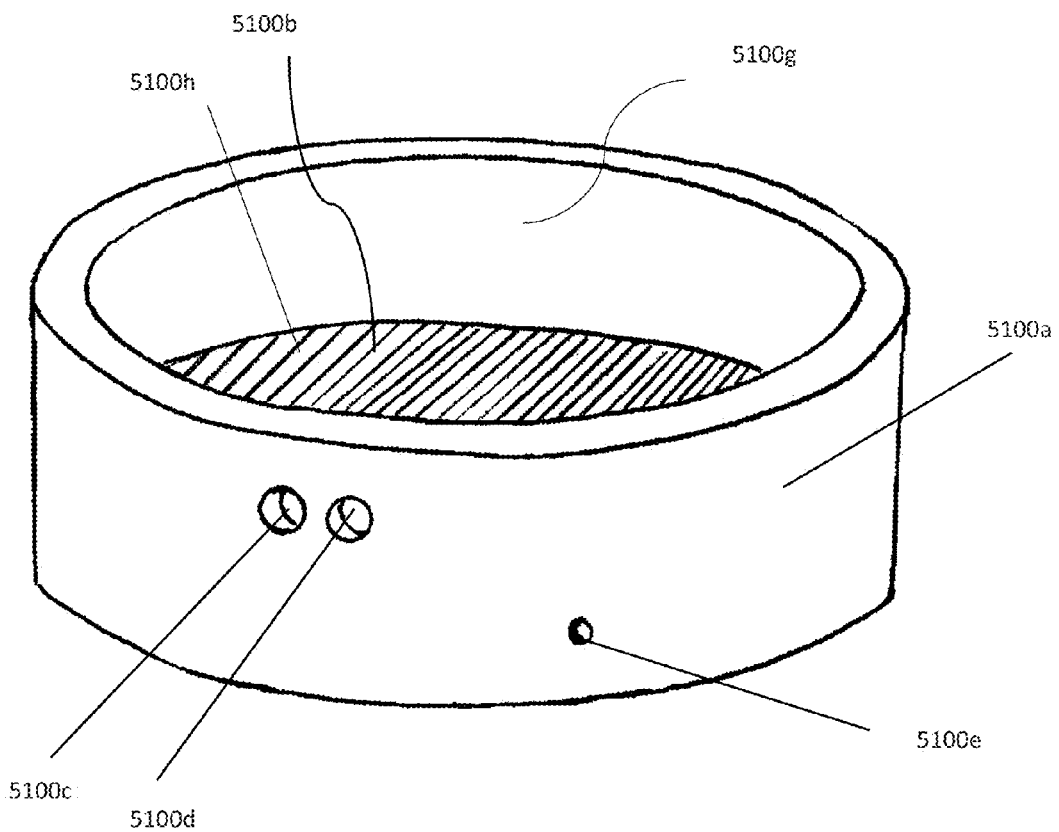
FIG. 23A-23D are semi-schematic drawings of an optical assembly of the fourth example.

FIG. 23A depicts the housing of the device of this example. The housing (100) has lateral walls (5100*a*) and base (5100*b*) that are approximately 1 mm in thickness. The housing has interior diameter of 13.5 mm, and a height of approximately 5 mm. On the lateral wall of the housing are adjacent openings (5100*c*, 5100*d*) for entrance and exit of coolant fluid. These openings are 1 mm in diameter. Also on the lateral wall is a 0.55 mm diameter opening (5100*e*) for entrance of light from the optical fiber of the laser. The base interior surface (5100*h*) of the housing is completely coated with Labsphere 6080 barium sulfate paint (Labsphere, North Sutton, N.H.), and the lateral wall interior surface (100*g*) has an optically specular polish with protective gold coating.

Figure 23B:
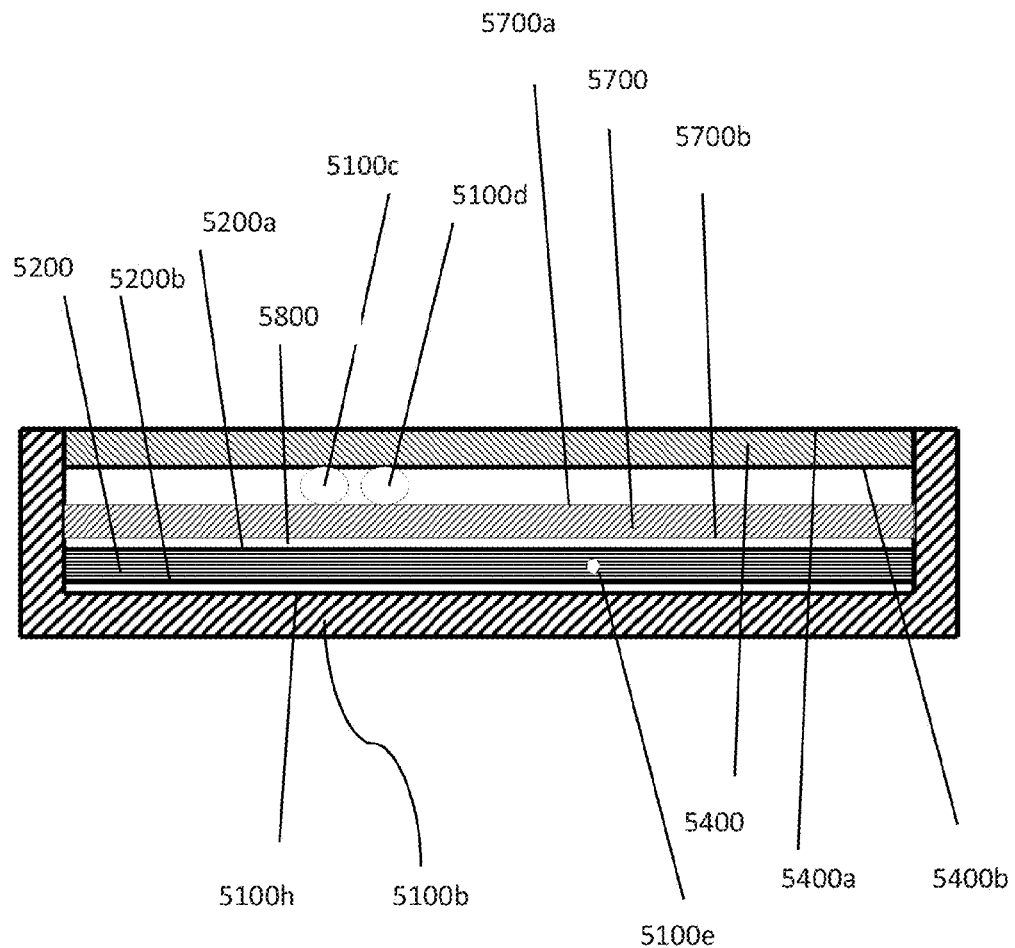

FIG. 23B is a cross sectional diagram of the optical assembly and housing of the device of this example. In near proximity to base interior surface (5100*h*) of the back of the housing (5100*b*) is the proximal surface (5200*b*) of a 1 mm-thick light guide plate (5200). The proximal surface (5700*b*) of a 1 mm-thick window plate (5700) is separated from the distal surface (5200*a*) of the light guide plate (5200) by an airspace (5800) of at least 2 microns thickness. A 1 mm-thick tissue contacting surface optic (5400) has a tissue contacting distal surface (5400*a*) and a coolant contacting proximal surface (5400*b*). The light guide plate (5200) and window plate (5700) are made of quartz, and the tissue contacting surface optic (5400) is a sapphire window. The proximal surface (5400*b*) of the sapphire window is separated from the distal surface (5700*a*) of the window plate by a 1 mm space that serves as a coolant layer (5300). The quartz light guide plate (5200), quartz window (5700), and sapphire window (5400) are plane parallel windows. The quartz light guide plate (5200) and quartz window (5700) are identical. The quartz light guide plate, quartz window and sapphire window are held fixed in contact with the housing lateral wall so that they are parallel to each other. The coolant input (5100*c*) and output (5100*d*) holes in the housing are indicated as projections on the coolant layer (5300). The entrance in the lateral wall for the optical fiber (5100*e*) is positioned so that light exiting the fiber is centered on the quartz light guide plate lateral edge.

In the device of this example, the fluid is perfluorocarbon (Fluorinert, 3M, Minneapolis, Minn.). The lateral edges of the sapphire window and quartz coolant window are optically smooth polished. The lateral walls of the light guide plate have optically smooth polished, with protected gold coating with the exception of a small (1 mm by 1 mm) uncoated area where light from the fiber enters the light guide plate.

Figure 23C:
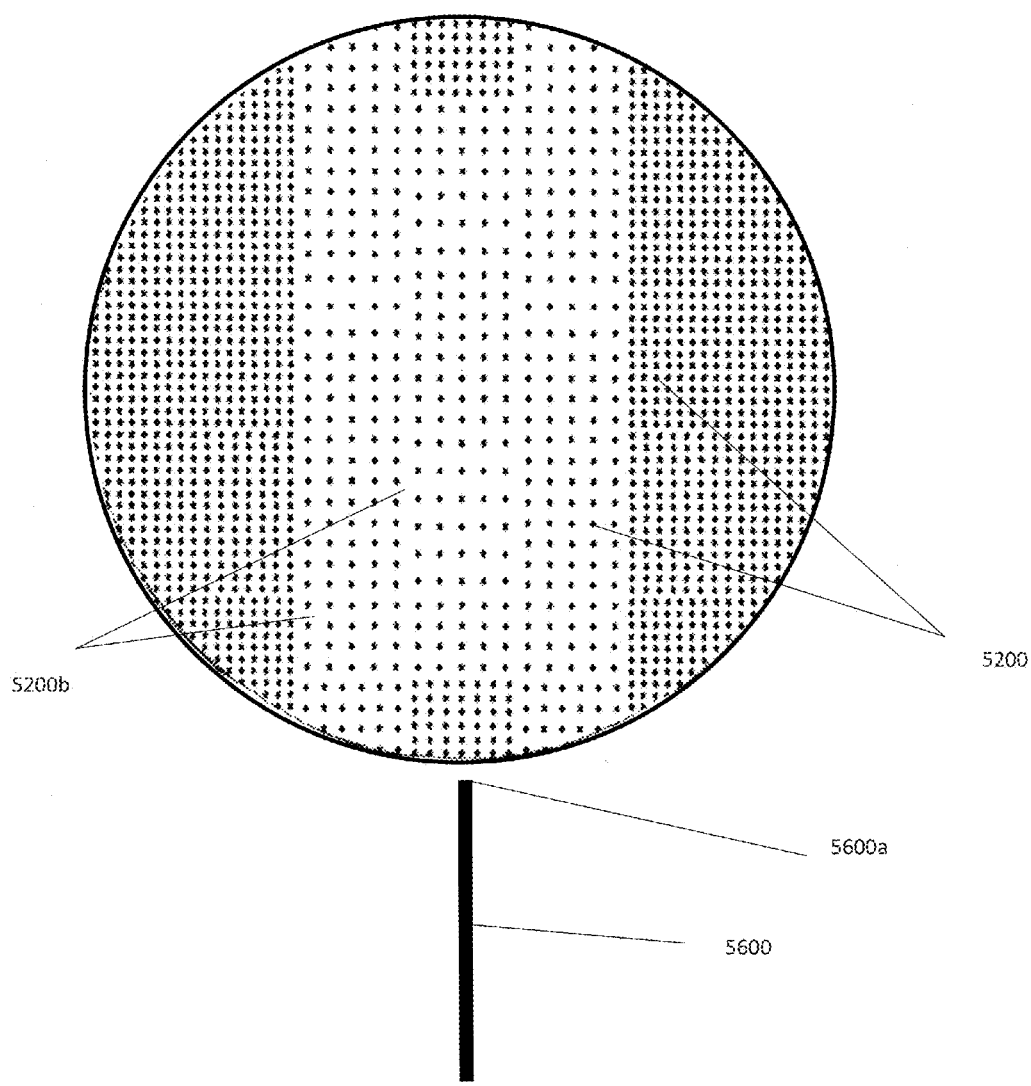

FIG. 23C is a schematic depiction of the extraction features (5200*e*) on the proximal surface (5200*b*) of the quartz light guide plate (5200). The exit face (5600*a*) of the optical fiber (5600) is adjacent to the lateral edge of the light guide plate. The extraction features are paint dots applied by screen printing using Labsphere 6080 paint. Each paint dot is 200 microns in diameter and is expanded in size in the for visibility. The arrangement of the paint dots was selected on the basis of Monte Carlo ray tracing (Optical Research Associates, Pasadena, Calif.).

Figure 23D:
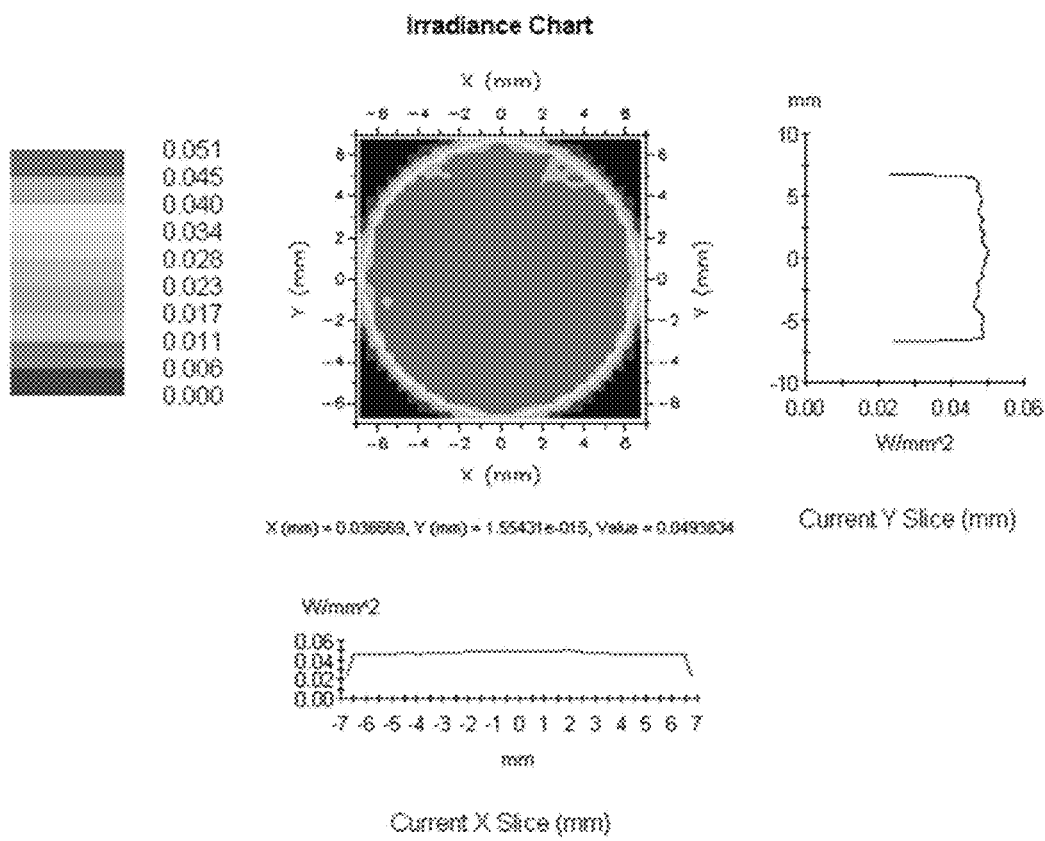

The results of the model calculations for the device of this example are shown in FIG. 23D. The optical characteristics are similar to those of the device of Example 3, which has similar design and approximately the same surface area. The efficiency of the device of this example is 68%. With a 10 W input, the maximum and minimum irradiance is 0.051 and 0.043 W/mm², respectively. The average irradiance is 47 mW/mm². Uniformity is +7%, −9%. The intensity profile is substantially Lambertian.

Example 5

Previous examples employed an 1120 nm diode laser. In this example, the same 18 mm×8 mm probe of Example 3 was used in model calculations with an 808 nm diode laser from JENOPTIC Laserdiode GmbH (Jena, Germany). The 808 nm laser was coupled to a 200 micron core diameter, 0.53 NA optical fiber (Ceramoptic WF 200/220 HT 53). As in Example 3, the fluid is perfluorocarbon FC-43 (Fluorinert, 3M, Minneapolis, Minn.). Thus, the device, including the pattern of paint dot extraction features, is completely unchanged from Example 3 and the only difference is that the source wavelength is changed from 1120 nm to 808 nm.

Figure 24:
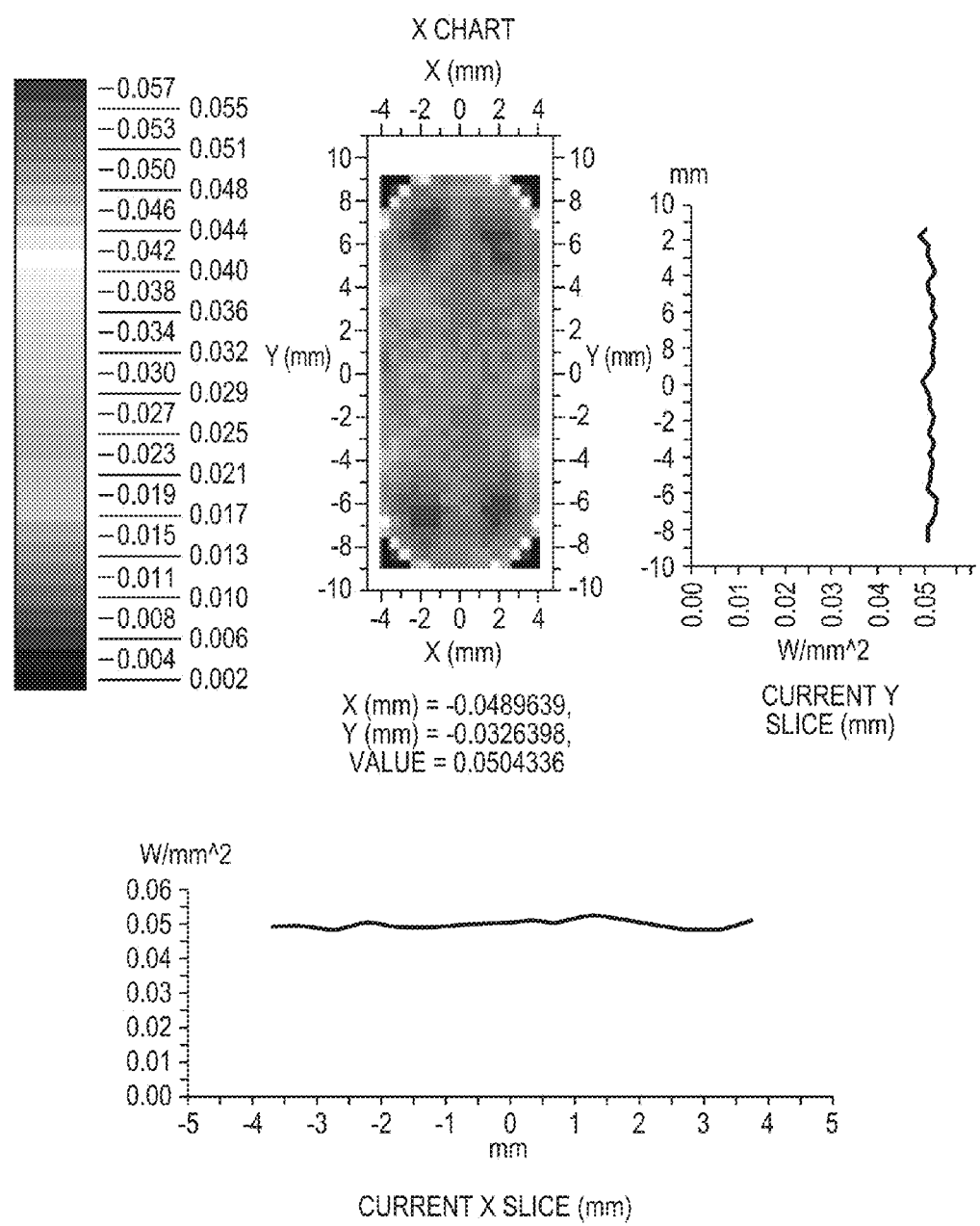
FIG. 24 shows the irradiance diagram for the optical assembly of the fifth example.

Results of the Monte Carlo ray trace calculation of irradiance at the sapphire contact window distal surface is shown in FIG. 24. It is found in the calculation of this example that despite the wavelength change of 300 nm, the irradiance distribution remains highly uniform. This example demonstrates the finding that a device may be used with different wavelengths without further modification being necessary.

Example 6

In this example, an apparatus of the thirteenth embodiment is used to treat the esophagus.

The optical assemblies of the apparatus shown schematically in FIG. 18A each have light-transmitting surface area of 18 mm length and 8 mm width, and made of sapphire. Each optical assembly is gently curved, as shown in FIGS. 18A and 18B, to conform to the lumen. The light source is a frequency doubled Nd:YAG laser (KTP laser) operating at 532 nm. The 532 nm wavelength is advantageous for treatment of Barrett's esophagus, for example, because it is strongly absorbed by blood, and BE tissue is more vascular than normal esophageal tissue. In this example, the use of an optical assembly to ablate the superficial mucosa of the esophagus is demonstrated using Monte Carlo calculations of the propagation of light in tissue, followed by heat transfer calculations.

Figure 25A:
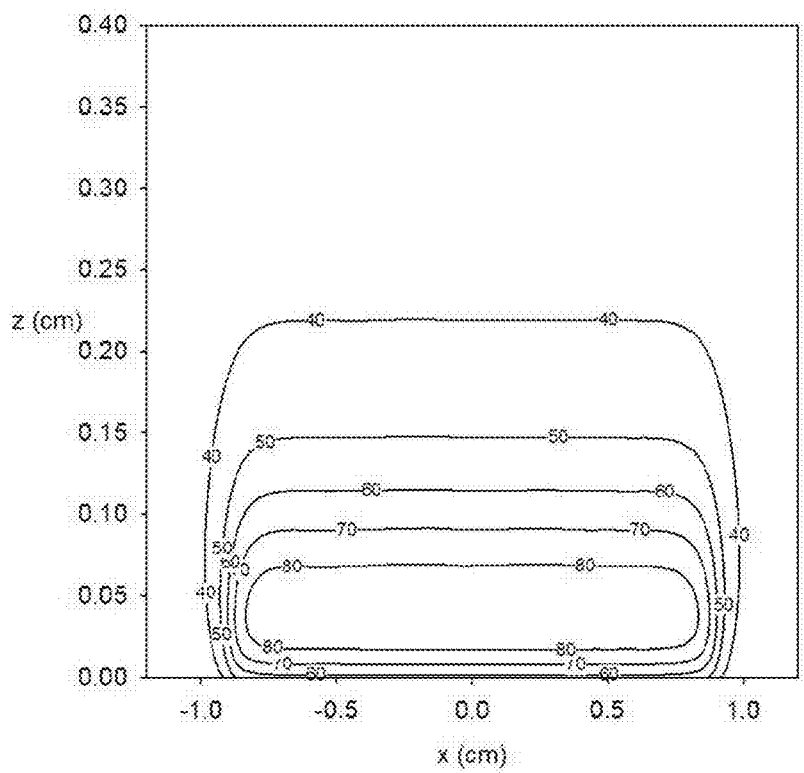
FIGS. 25A and 25B show the results of model calculations for irradiating the esophagus with a KTP laser and optical assembly with sapphire contact surface.
Figure 25B:
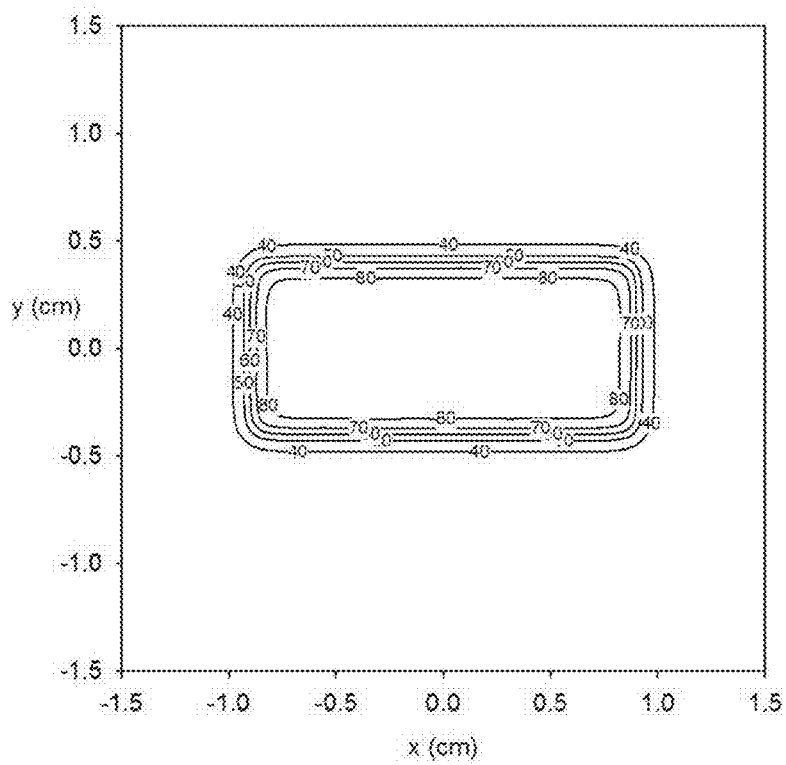

FIGS. 25A and 25B show calculations representing the effects of irradiating esophageal tissue with 20 W power at 532 nm, for a period of 3 seconds, using an 18 mm×8 mm optical assembly. x and y are the surface dimensions, and z is the depth in the tissue. In this calculation, the absorption coefficient was taken to be 0.719 cm⁻¹, the scattering coefficient was taken to be 13.9 cm⁻¹, and the anisotropy was taken to be 0.8. The sapphire light-emitting element was assumed to be uncooled, at 30 deg C. Based on the resultant temperature profile in FIG. 25A, significant thermal injury may be expected to a depth of about 700 to 1000 microns. This depth may be expected to damage, or ablate, most of the esophageal mucosa, and therefore may be an advantageous treatment for Barrett's esophagus. Because sapphire has a very high heat transfer coefficient, the surface of the mucosa in contact with the optical assembly is heated less than the underlying tissue. FIG. 25B shows the zone of heating 0.5 mm below the surface. It can be seen that the mucosal layer at this level is heated to 80 deg C. over an area approximately corresponding to the dimensions of the optical assembly, and is heated sufficiently that the mucosa will be irreversibly thermally injured.

Example 7

Figure 26:
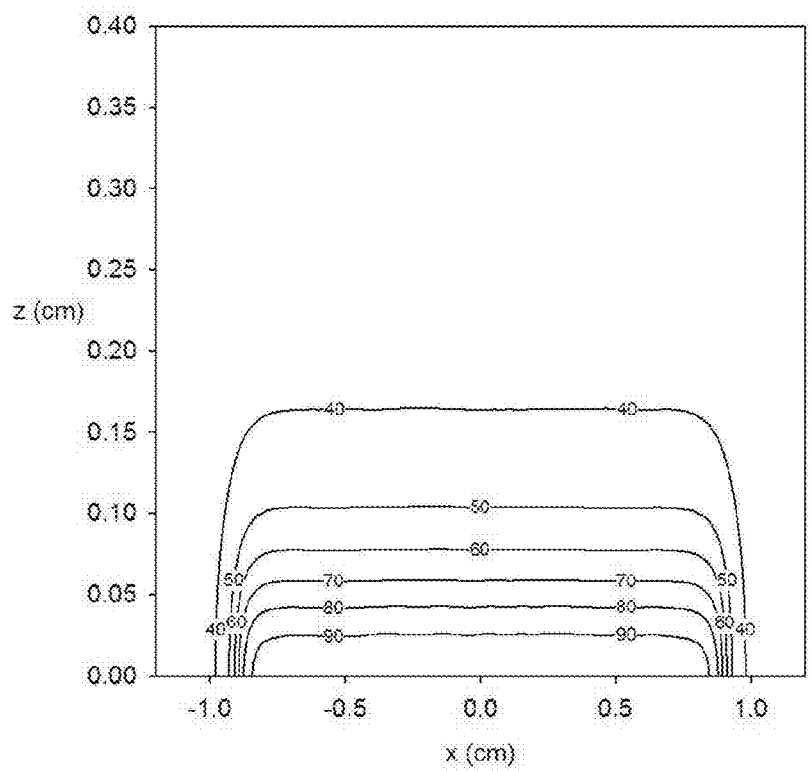
FIG. 26 shows the results of model calculations for irradiating the esophagus with a KTP laser and optical assembly with quartz contact surface.
Figure 27:
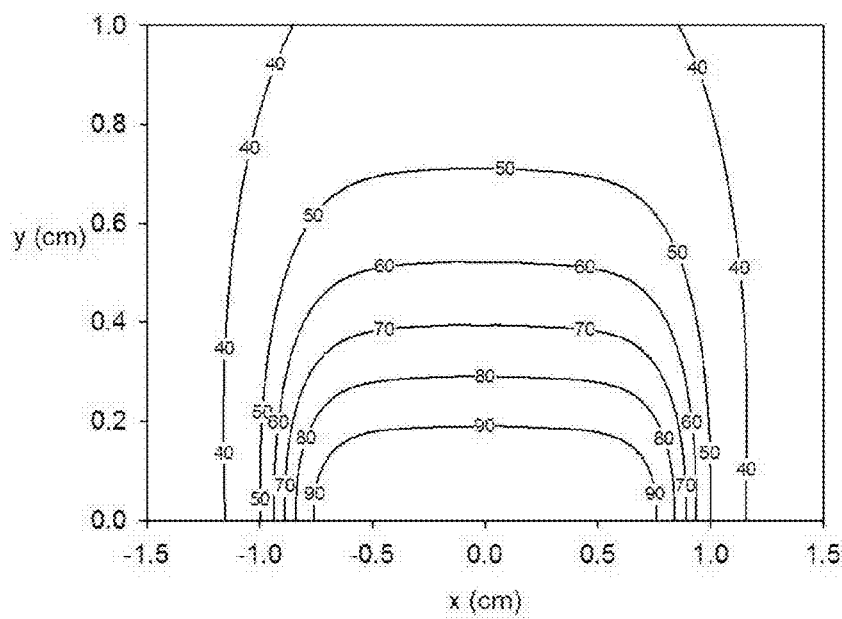
FIG. 27 shows the results of model calculations for irradating the esophagus with an 1125 nm laser and optical assembly with quartz contact surface.

The apparatus of Example 7 is the same as in Example 6, with the exception that the 18 mm×8 mm rectangular light-emitting contact surface is made of fused silica instead of sapphire. Fused silica has a much smaller heat transfer coefficient, and therefore surface heating is more efficient. In this example, the Monte Carlo and heat transfer calculation is performed as before for a 20 W, 532 nm light source. It is found that a 1.2 second irradiation time (fluence of 16.7 J/cm²) is sufficient to produce temperatures consistent with ablation or coagulation of the esophageal surface, as shown in FIG. 26. Because the exposure time is shorter, the heating is more localized at and near the tissue surface. Hence, it is found to be advantageous to use quartz as the optical element in optical assemblies of the invention for some applications involving surface tissue ablation.

Example 8

The apparatus of example 8 is the same as in example 7, with the exception that the light source is an 1125 nm quantum dot diode laser instead of a 532 nm KTP laser. In this example, the Monte Carlo and heat transfer calculation is performed before with a 20 W laser source and an 18 mm×8 mm rectangular light-emitting contact surface made of fused silica. It is found that a 7 second irradiation time (fluence of 97 J/cm²) produces temperatures consistent with ablation or coagulation of tissue to a depth of about 4 mm. The use of a deeply penetrating wavelength such as 1125 nm can be used with the apparatus of the invention to deeply heat or coagulate tissue. This capability may be useful, for example, in treating tumors located in a lumen or hollow organ.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for irradiating a tissue surface, said apparatus comprising an optical assembly, said assembly configured to be coupled by an optical transmission device to a light source, wherein the optical assembly comprises:
   a) a light-transmitting contact surface configured to transmit light to the tissue surface;
   b) a sapphire light guide plate having a light input surface at a lateral surface, said light guide plate adapted to receive light from the optical transmission device, the light propagating through the light guide plate;
   c) a reflecting plate separated from the proximal surface of the light guide plate;
   d) an extraction space defined by the proximal surface of the light guide plate and the reflecting plate;
   e) extraction features within the extraction space, the extraction features formed such that light reflected from the extraction features is transmitted to the tissue surface through the light-transmitting contact surface in a uniform distribution, the extraction features being in direct physical contact with the reflecting plate, the extraction features comprising a mixture of a binding material and inorganic crystalline microparticles, said microparticles having an index of refraction substantially greater than that of sapphire and a diameter of approximately 1 micron or larger, and where the binding material comprises a polymer and inorganic crystalline nanoparticles, said nanoparticles having an index of refraction substantially than that of sapphire and a diameter of approximately 25 to 50 nm or smaller, such that the binding material has an index of refraction approximately equal to the index of refraction of sapphire; and f) a housing enclosing at least a portion of the light guide plate and the reflecting plate and having an opening at the lateral input surface of the light guide plate.

2. The apparatus of claim 1, further including:
a cooling layer configured to remove heat from the light transmitting contact surface via a cooling fluid.

3. The apparatus of claim 1, wherein the extraction space comprises a heat transfer fluid having a refractive index lower than that of the light guide plate.

4. The apparatus of claim 1, wherein the housing has a thickness of about 6 mm or less.

5. The apparatus of claim 1, wherein the light-transmitting contact surface includes focusing features.

6. The apparatus of claim 1, further including:
a light source operably coupled to the light guide plate.

7. The apparatus of claim 1, wherein the inorganic crystalline microparticles and the inorganic crystalline nanoparticles are zirconium oxide, and the polymer is polyvinyl alcohol.

8. The apparatus of claim 1, wherein the extraction features are formed by application of material to the proximal surface of the light guide plate.

9. The apparatus of claim 1, wherein the uniform distribution is uniform to within ±50% of an average over the light-transmitting contact surface.

10. The apparatus of claim 1, wherein the uniform distribution is uniform to within ±25% of an average over the light-transmitting contact surface.

11. The apparatus of claim 1, wherein the uniform distribution is uniform to within ±10% of an average over the light-transmitting contact surface.

12. A method of irradiating a tissue surface comprising:
a) guiding light via an optical assembly, said assembly configured to produce a uniform distribution of light and configured to be coupled by an optical transmission device to a light source, wherein the optical assembly comprises:
   i) a light-transmitting contact surface configured to transmit light to the tissue surface;
   ii) a sapphire light guide plate having a light input surface at a lateral surface, said light guide plate adapted to receive light from the optical transmission device, the light propagating through the light guide plate;
   iii) a reflecting plate separated from the proximal surface of the light guide plate;
   iv) an extraction space defined by the proximal surface of the light guide plate and the reflecting plate; and
   v) extraction features within the extraction space, the extraction features formed such that light reflected from the extraction features is transmitted to the tissue surface through the light-transmitting contact surface in a uniform distribution, the extraction features being in direct physical contact with the reflecting plate, the extraction features comprising a mixture of a binding material and inorganic crystalline microparticles, said microparticles having an index of refraction substantially greater than that of sapphire and a diameter of approximately 1 micron or larger, and where the binding material comprises a polymer and inorganic crystalline nanoparticles, said nanoparticles having an index of refraction substantially than that of sapphire and a diameter of approximately 25 to 50 nm or smaller, such that the binding material has an index of refraction approximately equal to the index of refraction of sapphire; and
   vi) a housing enclosing at least a portion of the light guide plate and the reflecting plate and having an opening at the lateral input surface of the light guide plate; and
b) irradiating the tissue surface with light guided by the optical assembly.

13. The method of claim 12, further including:
generating the light with a light source operably coupled to the lateral input surface of the light guide plate.

14. The method of claim 12, further including:
removing heat from the light-transmitting contact surface via a cooling fluid.

15. The method of claim 14, wherein the cooling fluid has an index of refraction higher than that of the light guide plate.

16. The method of claim 12, wherein the light-transmitting contact surface has a contact surface area of at least about 30 mm2.

17. The method of claim 12, wherein the light-transmitting contact surface includes focusing features.

18. The method of claim 12, wherein the housing has a thickness of about 6 mm or less.

19. The method of claim 12, wherein the extraction features are formed by application of material to the proximal surface of the light guide plate.

20. The method of claim 12, wherein the uniform distribution is uniform to within ±50% of an average over the light-transmitting contact surface.

21. The method of claim 12, wherein the uniform distribution is uniform to within ±25% of an average over the light-transmitting contact surface.

22. The method of claim 12, wherein the uniform distribution is uniform to within ±10% of an average over the light-transmitting contact surface.

* * * * *

UNITED STATES PATENT AND TRADEMARK OFFICE
CERTIFICATE OF CORRECTION

PATENT NO. : 9,554,856 B2  
APPLICATION NO. : 13/965715  
DATED : January 31, 2017  
INVENTOR(S) : Kathleen McMillan, Anurag Gupta and James Patrick McGuire, Jr.

Page 1 of 1

It is certified that error appears in the above-identified patent and that said Letters Patent is hereby corrected as shown below:

In the Claims

In Claim 1, Column 43, Line 5, delete "substantially than" and insert -- substantially greater than --.

In Claim 12, Column 44, Line 17, delete "substantially than" and insert -- substantially greater than --.

In Claim 12, Column 44, Line 18, delete "25to" and insert -- 25 to --.

Signed and Sealed this
Fourth Day of April, 2017

Michelle K. Lee
*Director of the United States Patent and Trademark Office*